US008498698B2

(12) United States Patent
Donofrio et al.

(10) Patent No.: US 8,498,698 B2
(45) Date of Patent: *Jul. 30, 2013

(54) ISOLATION OF SENSING AND STIMULATION CIRCUITRY

(75) Inventors: William T. Donofrio, Andover, MN (US); Paul G. Krause, Shoreview, MN (US); James D. Reinke, Maple Grove, MN (US); David J. Peichel, Minneapolis, MN (US); Gerald P. Arne, Long Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 623 days.

This patent is subject to a terminal disclaimer.

(21) Appl. No.: 12/551,409

(22) Filed: Aug. 31, 2009

(65) Prior Publication Data
US 2010/0114248 A1 May 6, 2010

Related U.S. Application Data

(60) Provisional application No. 61/110,428, filed on Oct. 31, 2008, provisional application No. 61/148,852, filed on Jan. 30, 2009.

(51) Int. Cl.
*A61N 1/00* (2006.01)
(52) U.S. Cl.
USPC .......................................................... 607/2
(58) Field of Classification Search
USPC ................................................ 607/2, 60, 63
See application file for complete search history.

(56) References Cited

U.S. PATENT DOCUMENTS

| | | | |
|---|---|---|---|
| 3,421,511 A | 1/1969 | Schwartz et al. |
| 3,522,811 A | 8/1970 | Seymour et al. |
| 3,593,718 A | 7/1971 | Krasner et al. |
| 3,645,267 A | 2/1972 | Hagfors |
| 3,650,277 A | 3/1972 | Sjostrand et al. |
| 3,796,221 A | 3/1974 | Hagfors |
| 3,878,564 A | 4/1975 | Yao et al. |
| 3,888,260 A | 6/1975 | Fischell |
| 4,044,774 A | 8/1977 | Corbin et al. |

(Continued)

FOREIGN PATENT DOCUMENTS

| | | |
|---|---|---|
| EP | 0228539 B1 | 11/1990 |
| EP | 0688577 A1 | 12/1995 |

(Continued)

OTHER PUBLICATIONS

"Common-mode interference" Wikipedia reference retrieved on Aug. 25, 2008, (1 page).

(Continued)

*Primary Examiner* — George Manuel
(74) *Attorney, Agent, or Firm* — Carol F. Barry

(57) ABSTRACT

The disclosure describes techniques of reducing or eliminating a commonality between two modules within the same implantable medical device. Each module within the implantable medical device provides therapy to a patient. The commonality between the two modules exists due to at least one common component shared by the two modules. The commonality between the two modules may create common-mode interference and a shunt current. In accordance with this disclosure, various isolation circuits located at various locations are disclosed to reduce or eliminate the commonality between the two modules. The reduction or elimination of the commonality between the two modules may reduce or eliminate common-mode interference and the shunt current.

36 Claims, 38 Drawing Sheets

U.S. PATENT DOCUMENTS

| | | |
|---|---|---|
| 4,146,029 A | 3/1979 | Ellinwood, Jr. |
| 4,340,063 A | 7/1982 | Maurer |
| 4,374,382 A | 2/1983 | Markowitz |
| 4,428,378 A | 1/1984 | Anderson et al. |
| 4,458,696 A | 7/1984 | Larimore |
| 4,485,813 A | 12/1984 | Anderson et al. |
| 4,535,774 A | 8/1985 | Olson |
| 4,549,556 A | 10/1985 | Tarjan et al. |
| 4,686,988 A | 8/1987 | Sholder |
| 4,694,835 A | 9/1987 | Strand |
| 4,745,923 A | 5/1988 | Winstrom |
| 4,750,495 A | 6/1988 | Moore et al. |
| 4,787,389 A | 11/1988 | Tarjan |
| 4,827,936 A | 5/1989 | Pless et al. |
| 4,830,006 A | 5/1989 | Haluska et al. |
| 4,880,005 A | 11/1989 | Pless et al. |
| 4,903,701 A | 2/1990 | Moore et al. |
| 4,998,974 A | 3/1991 | Aker |
| 5,031,618 A | 7/1991 | Mullett |
| 5,058,584 A | 10/1991 | Bourgeois |
| 5,111,816 A | 5/1992 | Pless et al. |
| 5,117,824 A | 6/1992 | Keimel et al. |
| 5,135,004 A | 8/1992 | Adams et al. |
| 5,149,713 A | 9/1992 | Bousquet |
| 5,199,428 A | 4/1993 | Obel et al. |
| 5,203,326 A | 4/1993 | Collins |
| 5,213,098 A | 5/1993 | Bennett et al. |
| 5,220,917 A | 6/1993 | Cammilli et al. |
| 5,220,929 A | 6/1993 | Marquit |
| 5,243,980 A | 9/1993 | Mehra |
| 5,251,621 A | 10/1993 | Collins |
| 5,255,691 A | 10/1993 | Otten |
| 5,261,400 A | 11/1993 | Bardy |
| 5,292,336 A | 3/1994 | Spence, Jr. et al. |
| 5,292,338 A | 3/1994 | Bardy |
| 5,330,505 A | 7/1994 | Cohen |
| 5,330,507 A | 7/1994 | Schwartz |
| 5,330,515 A | 7/1994 | Rutecki et al. |
| 5,331,966 A | 7/1994 | Bennett et al. |
| 5,334,221 A | 8/1994 | Bardy |
| 5,342,409 A | 8/1994 | Mullett |
| 5,345,376 A | 9/1994 | Nourbakhsh |
| 5,360,441 A | 11/1994 | Otten |
| 5,464,434 A | 11/1995 | Alt |
| 5,496,363 A | 3/1996 | Burgio et al. |
| 5,545,186 A | 8/1996 | Olson et al. |
| 5,564,434 A | 10/1996 | Halperin et al. |
| 5,607,418 A | 3/1997 | Arzbaecher |
| 5,638,832 A | 6/1997 | Singer et al. |
| 5,651,378 A | 7/1997 | Matheny et al. |
| 5,690,681 A | 11/1997 | Geddes et al. |
| 5,700,282 A | 12/1997 | Zabara |
| 5,702,429 A | 12/1997 | King |
| 5,755,736 A | 5/1998 | Gillberg et al. |
| 5,776,170 A | 7/1998 | MacDonald et al. |
| 5,792,187 A | 8/1998 | Adams |
| 5,807,234 A | 9/1998 | Bui et al. |
| 5,817,131 A | 10/1998 | Elsberry et al. |
| 5,824,021 A | 10/1998 | Rise |
| 5,859,578 A | 1/1999 | Arnold |
| 5,913,876 A | 6/1999 | Taylor et al. |
| 6,006,134 A | 12/1999 | Hill et al. |
| 6,058,331 A | 5/2000 | King |
| 6,073,048 A | 6/2000 | Kieval et al. |
| 6,134,470 A | 10/2000 | Hartlaub |
| 6,141,586 A | 10/2000 | Mower |
| 6,178,349 B1 | 1/2001 | Kieval |
| 6,198,972 B1 | 3/2001 | Hartlaub et al. |
| 6,272,377 B1 | 8/2001 | Sweeney et al. |
| 6,308,101 B1 | 10/2001 | Faltys et al. |
| 6,358,281 B1 | 3/2002 | Berrang et al. |
| 6,438,420 B1 | 8/2002 | Thompson |
| 6,473,644 B1 | 10/2002 | Terry, Jr. et al. |
| 6,587,726 B2 | 7/2003 | Lurie et al. |
| 6,713,671 B1 | 3/2004 | Wang et al. |
| 6,788,974 B2 | 9/2004 | Bardy et al. |
| 6,885,888 B2 | 4/2005 | Rezai |
| 6,901,292 B2 | 5/2005 | Hrdlicka et al. |
| 6,944,489 B2 | 9/2005 | Zeijlemaker et al. |
| 7,010,345 B2 | 3/2006 | Hill et al. |
| 7,212,864 B2 | 5/2007 | Wahlstrand et al. |
| 7,218,964 B2 | 5/2007 | Hill et al. |
| 7,242,982 B2 | 7/2007 | Singhal et al. |
| 7,305,266 B1 | 12/2007 | Kroll |
| 7,369,898 B1 | 5/2008 | Kroll et al. |
| 2001/0001126 A1 | 5/2001 | Cammilli et al. |
| 2002/0042634 A1 | 4/2002 | Bardy et al. |
| 2002/0068958 A1 | 6/2002 | Bardy et al. |
| 2002/0107546 A1 | 8/2002 | Ostroff et al. |
| 2002/0107553 A1 | 8/2002 | Hill et al. |
| 2002/0161402 A1 | 10/2002 | Vogel et al. |
| 2003/0120320 A1 | 6/2003 | Solom |
| 2005/0017054 A1 | 1/2005 | Iverson et al. |
| 2005/0267543 A1 | 12/2005 | Heruth et al. |
| 2005/0288743 A1* | 12/2005 | Ahn et al. ............... 607/61 |
| 2006/0217792 A1 | 9/2006 | Hussein et al. |
| 2007/0055308 A1 | 3/2007 | Haller et al. |
| 2007/0255332 A1 | 11/2007 | Cabelka et al. |
| 2008/0015659 A1 | 1/2008 | Zhang et al. |
| 2009/0281623 A1 | 11/2009 | Kast et al. |

FOREIGN PATENT DOCUMENTS

| | | |
|---|---|---|
| WO | 02083236 A2 | 10/2002 |
| WO | 03063946 A2 | 8/2003 |
| WO | 2004047295 A1 | 6/2004 |
| WO | 2007/127705 A1 | 11/2007 |
| WO | 2007/149757 A2 | 12/2007 |
| WO | 2008/111986 A1 | 9/2008 |

OTHER PUBLICATIONS

U.S. Appl. No. 12/609,901, filed Oct. 30, 2009.
U.S. Appl. No. 12/551,331, filed Aug. 31, 2009.
U.S. Appl. No. 12/551,377, filed Aug. 31, 2009.
Invitation to Pay Additional Fees and, Where Applicable, Protest Fee from international application No. PCT/US2009/062399, mailed Feb. 3, 2010, 5 pp.
Bilgutay et al, "Vagal Tuning—A New Concept in the Treatment of Supraventricular Arrhythmias, Angina Pectoris, and Heart Failure," *Journal of Thoracic Cardiovascular Surgery* 56(1): 71-82, Jul. 1968.
Braunwald et al., "Carotid Sinus Nerve Stimulation in the Treatment of Angina Pectoris and Supraventricular Tachycardia," *California Medicine* 112(3): 41-50, Mar. 1970.
Armour, "Instant to Instant Reflex Cardiac Regulation," Cardiology 61: 309-328, 1976.
Schwartz et al., "Effect of dorsal root section on the arrhythmias associated with coronary occlusion," *American Journal of Physiology* 231(3): 923-928, Sep. 1976.
Blair et al., "Responses of Thoracic Spinothalamic Neurons to Intracardiac Injection of Bradykinin in the Monkey," *Circulation Research* 51(1): 83-94, Jul. 1982.
Ammons et al., "Vagal Afferent Inhibition of Spinothalamic Cell Responses to Sympathetic Afferents and Bradykinin in the Monkey," *Circulation Research* 53(5): 603-612, Nov. 1983.
Blair et al., "Responses of Thoracic Spinothalamic and Spinoreticular Cells to Coronary Artery Occlusion," *Journal of Neurophysiology* 51(4): 636-648, Apr. 1984.
Ammons et al., "Effects of intracardiac bradykinin on $T_2$-$T_5$ medial spinothalamic cells," *American Journal of Physiology* 249: R147-R152, 1985.
Blair et al., "Activation of Feline Spinal Neurones by Potentiated Ventricular Contractions and Other Mechanical Cardiac Stimuli," *Journal of Physiology* 404: 649-667, 1988.
Schwartz et al., "Autonomic Mechanisms and Sudden Death—New Insights From Analysis of Baroreceptor Reflexes in Conscious Dogs With and Without a Myocardial Infarction," *Circulation* 78(4): 969-979, Oct. 1988.
Hobbs et al., "Cardiac and Abdominal Vagal Afferent Inhibition of Primate $T_9$-$S_1$ Spinothalamic Cells," *The American Physiological Society* 257: R889-R895, 1989.
Butler et al., "Cardiac Responses to Electrical Stimulation of Discrete Loci in Canine Atrial and Ventricular Ganglionated Plexi," *The American Physiological Society* 259: H1365-H1373, 1990.

Hull et al., "Heart Rate Variability Before and After Myocardial Infarction in Conscious Dogs At High and Low Risk of Sudden Death," *The American College of Cardiology* 16(4): 978-985, Oct. 1990.
Armour, "Intrinsic Cardiac Neurons," *Journal of Cardiovascular Electrophysiology* 2(4): 331-341, Aug. 1991.
Chandler et al., "Effects of Vagal Afferent Stimulation on Cervical Spinothalamic Tract Neurons in Monkeys," *Pain* 44: 81-87, 1991.
Linderoth et al., "Effects of Sympathectomy on Skin and Muscle Microcirculation During Dorsal Column Stimulation: Animal Studies," *Neurosurgery* 29(6): 874-879, 1991.
Vanoli et al., "Vagal Stimulation and Prevention of Sudden Death in Conscious Dogs With a Healed Myocardial Infarction," *Circulation Research* 68(5): 1471-1481, May 1991.
Cardinal et al., "Distinct Activation Patterns of Idioventricular Rhythms and Sympathetically-Induced Ventricular Tachycardias in Dogs With Atrioventricular Block," *PACE* 15: 1300-1316, Sep. 1992.
Fu et al., "Vagal Afferent Fibers Excite Upper Cervical Neurons and Inhibit Activity of Lumbar Spinal Cord Neurons in the Rat," *Pain* 51: 91-100, 1992.
Hobbs et al., "Evidence That $C_1$ and $C_2$ Propriospinal Neurons Meditate the Inhibitory Effects of Viscerosomatic Spinal Afferent Input on Primate Spinothalamic Tract Neurons," *Journal of Neurophysiology* 67(4): 852-860, Apr. 1992.
Hobbs et al., "Segmental Organization of Visceral and Somatic Input Onto $C_3$-$T_6$ Spinothalamic Tract Cells of the Monkey," *Journal of Neurophysiology* 68(5): 1575-1588, Nov. 1992.
Chandler et al., "A Mechanism of Cardiac Pain Suppression by Spinal Cord Stimulation: Implications for Patients With Angina Pectoris," *European Heart Journal* 14: 96-105, 1993.
Huang et al., "Effects of Transient Coronary Artery Occlusion on Canine Intrinsic Cardiac Neuronal Activity," *Integrative Physiological and Behavioral Science* 28(1): 5-21, Jan.-Mar. 1993.
Adamson et al., "Unexpected Interaction Between β-Adrenergic Blockade and Heart Rate Variability Before and After Myocardial Infarction—A Longitudinal Study in Dogs At High and Low Risk for Sudden Death," *Circulation* 90(2): 976-982, Aug. 1994.
Ardell, "Structure and Function of Mammalian Intrinsic Cardiac Neurons," *Neurocardiology*: 95-114, 1994.
Armour, "Peripheral Autonomic Neuronal Interactions in Cardiac Regulation," *Neurocardiology*: 219-244, 1994.
Foreman, "Spinal Cord Neuronal Regulation of the Cardiovascular System," *Neurocardiology*: 245-276, 1994.
Hull et al., "Exercise Training Confers Anticipatory Protection From Sudden Death During Acute Myocardial Ischemia," *Circulation* 89(2): 548-552, Feb. 1994.
Linderoth et al., "Sympathetic Mediation of Peripheral Vasodilation Induced by Spinal Cord Stimulation: Animal Studies of the Role of Cholinergic and Adrenergic Receptor Subtypes," *Neurosurgery* 35(4): 711-719, Oct. 1994.
Yuan et al., "Gross and Microscopic Anatomy of the Canine Intrinsic Cardiac Nervous System," *The Anatomical Record* 239: 75-87, 1994.
Armour, "Intrinsic Cardiac Neurons Involved in Cardiac Regulation Possess alpha$_1$, alpha$_2$, beta$_1$ and beta$_2$-Adrenoreceptors," *Can. J. Cardiol.* 13(3): 277-284, Mar. 1997.
Cardinal et al., "Reduced Capacity of Cardiac Efferent Sympathetic Neurons to Release Noradrenaline and Modify Cardiac Function in Tachycardia-Induced Canine Heart Failure," *Can. J. Physiol. Pharmacol.* 74: 1070-1078, 1996.
Chandler et al., "Vagal, Sympathetic and Somatic Sensory Inputs to Upper Cervical ($C_1$-$C_3$) Spinothalamic Tract Neurons in Monkeys," *Journal of Neurophysiology* 76(4): 2555-2567, 1996.
Zhang et al., "Thoracic Visceral Inputs Use Upper Cervical Segments to Inhibit Lumbar Spinal Neurons in Rats" *Brain Research* 709: 337-342, 1996.
Armour et al., "Gross and Microscopic Anatomy of the Human Intrinsic Cardiac Nervous System," *The Anatomical Record* 247: 289-298, 1997.
Croom et al., "Cutaneous Vasodilation During Dorsal Column Stimulation Is Mediated By Dorsal Roots and CGRP," *Am. J. Physiol.* 272 (*Heart Circ. Physiol.* 41): H950-H957, 1997.

Hautvast et al., "Spinal Cord Stimulation in Chronic Intractable Angina Pectoris: A Randomized, Controlled Efficacy Study," *American Heart Journal*, 136(6): 1114-1120, 1998.
Barron et al., "Spinal Integration of Antidromic Mediated Cutaneous Vasodilation During Dorsal Spinal Cord Stimulation in the Rat," *Neuroscience Letters* 260: 173-176, 1999.
Foreman, "Mechanisms of Cardiac Pain," Annu. Rev. Physiol. 61: 143-167, 1999.
Linderoth et al., "Physiology of Spinal Cord Stimulation: Review and Update," *Neuromodulation* 2(3):150-164, 1999.
Qin et al., "Chemical Activation of Cervical Cell Bodies: Effects on Responses to Colorectal Distension in Lumbosacral Spinal Cord of Rats," *J Neurophysiol* 82: 3423-3433, 1999.
Chandler et al., "Intrapericardiac Injections of Algogenic Chemicals Excite Primate $C_1$-$C_2$ Spinothalamic Tract Neurons," *Am J. Physiol. Regulatory Integrative Comp. Physiol.* 279: R560-568, 2000.
Foreman et al., "Modulation of Intrinsic Cardiac Neurons by Spinal Cord Stimulation: Implications for Its Therapeutic Use in Angina Pectoris," *Cardiovascular Research* 47: 367-375, 2000.
Hopkins et al., "Pathology of Intrinsic Cardiac Neurons From Ischemic Human Hearts," *The Anatomical Record* 259: 424-436, 2000.
Kember et al., "Aperiodic Stochastic Resonance in a Hysteretic Population of Cardiac Neurons," *The American Physical Society* Physical Review E 61(2): 1816-1824, Feb. 2000.
Meyerson et al., "Spinal Cord Stimulation," *Bonica's Management of Pain*: 1857-1876, 2001.
Ardell, "Neurohumoral Control of Cardiac Function," *Heart Physiology and Pathophysiology, Fourth Edition*: 45-49, 2001.
Farrell et al., "Angiotensin II Modulates Catecholamine Release Into Interstitial Fluid of Canine Myocardium In Vivo," *Am J. Physiol. Heart Cir. Physiol.* 281: H813-H822, 2001.
Kingma, Jr. et al., "Neuromodulation Therapy Does Not Influence Blood Flow Distribution or Left-Ventricular Dynamics During Acute Myocardial Ischemia," *Autonomic Neuroscience: Basic & Clinical* 91: 47-54, 2001.
Tanaka et al., "Low Intensity Spinal Cord Stimulation May Induce Cutaneous Vasodilation Via CGRP Release," *Brain Research* 896: 183-187, 2001.
Qin et al., "Responses and Afferent Pathways of Superficial and Deeper $C_1$-$C_2$ Spinal Cells to Intrapericardial Algogenic Chemicals in Rats," *J. Neurophysiol* 85:1522-1532, 2001.
Armour et al., "Long-Term Modulation of the Intrinsic Cardiac Nervous System by Spinal Cord Neurons in Normal and Ischaemic Hearts," *Autonomic Neuroscience: Basic & Clinical* 95: 71-79, 2002.
Chandler et al., "Spinal Inhibitory Effects of Cardiopulmonary Afferent Inputs in Monkeys: Neuronal Processing in High Cervical Segments," *J. Neurophysiol* 87: 1290-1302, 2002.
Cardinal et al., "Spinal Cord Activation Differentially Modulates Ischaemic Electrical Responses to Different Stressors in Canine Ventricles," *Autonomic Neuroscience: Basic & Clinical* 111: 37-47, 2004.
Ardell, "Intrathoracic Neuronal Regulation of Cardiac Function," *Basic and Clinical Neurocardiology* 118-152, 2004.
Siddons et al., "Special Considerations: Pacing in Acute Myocardial Infarction," *Cardiac Pacemakers* Chapter 11: 200-217, 1967.
Bluemel et al., "Parasympathetic Postganglionic Pathways to the Sinoatrial Node," *American Journal of Physiology* 259 (*Heart Circ. Physiol.* 28): H1504-HI510, 1990.
Cooper et al, "Neural Effects on Sinus Rate and Atrioventricular Conduction Produced by Electrical Stimulation from a Transvenous Electrode Catheter in the Canine Right Pulmonary Artery," *Circulation Research* 46(1): 48-57, Jan. 1980.
Randall et al, "Functional Anatomy of the Cardiac Efferent Innervation," *Neurocardiology* Chapter 1: 3-24, 1988.
International Search Report and Written Opinion of international application No. PCT/US2009/062399, mailed May 18, 2010, 17 pp.
International Preliminary Report on Patentability from international application No. PCT/US2009/062399, mailed May 12, 2011, 10 pp.
Office Action for U.S. Appl. No. 12/551,331, dated Mar. 16, 2012, 12 pp.
Final Office Action from U.S. Appl. No. 12/609,901, dated Nov. 7, 2012, 7 pp.

Response to Final Office Action dated Aug. 22, 2012 and Advisory Action dated Nov. 2, 2012, from U.S. Appl. No. 12/551,331, filed Nov. 19, 2012, 13 pp.
Office Action from U.S. Appl. No. 12/551,377, dated Apr. 23, 2012, 8 pp.
Response to Office Action dated Mar. 16, 2012, from U.S. Appl. No. 12/551,331, filed Jun. 18, 2012, 9 pp.
Office Action from U.S. Appl. No. 12/609,901, dated Jul. 13, 2012, 11 pp.
Office Action from U.S. Appl. No. 12/551,331, dated Aug. 22, 2012, 15 pp.
Response to Office Action dated Aug. 22, 2012, from U.S. Appl. No. 12/551,331, filed Oct. 22, 2012, 14 pp.
Response to Office Action dated Jul. 13, 2012, from U.S. Appl. No. 12/609,901, filed Oct. 15, 2012, 13 pp.
Response to Office Action dated Apr. 23, 2012, from U.S. Appl. No. 12/551,377, filed Sep. 21, 2012, 13 pp.
Office Action from U.S. Appl. No. 12/551,377, dated Oct. 11, 2012, 5 pp.
Response to Office Action dated Nov. 7, 2012, from U.S. Appl. No. 12/609,901, filed Jan. 9, 2013, 11 pp.
Response to Office Action dated Oct. 11, 2012, from U.S. Appl. No. 12/551,377, and Terminal Disclaimer filed Jan. 11, 2013, 3 pp.

* cited by examiner

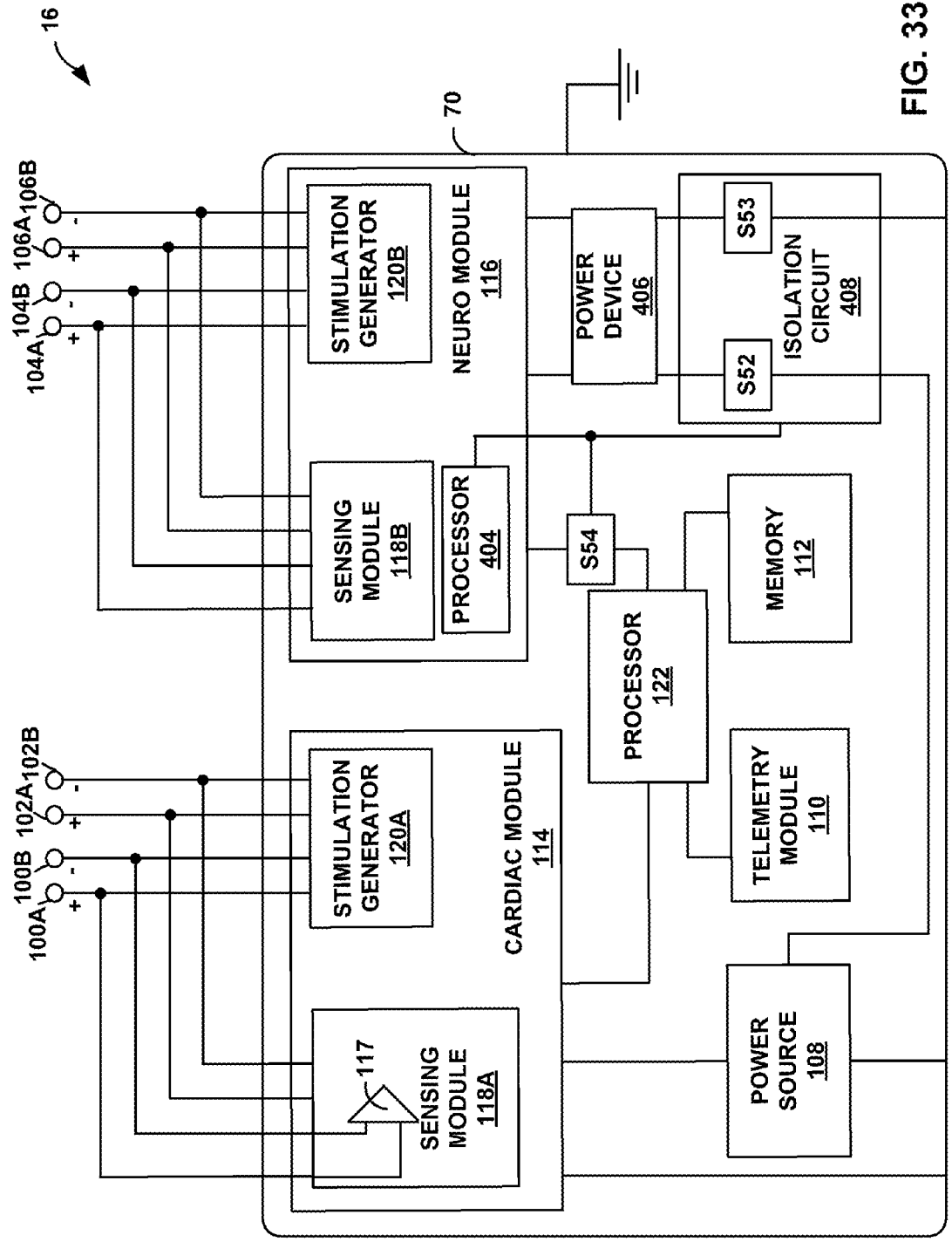

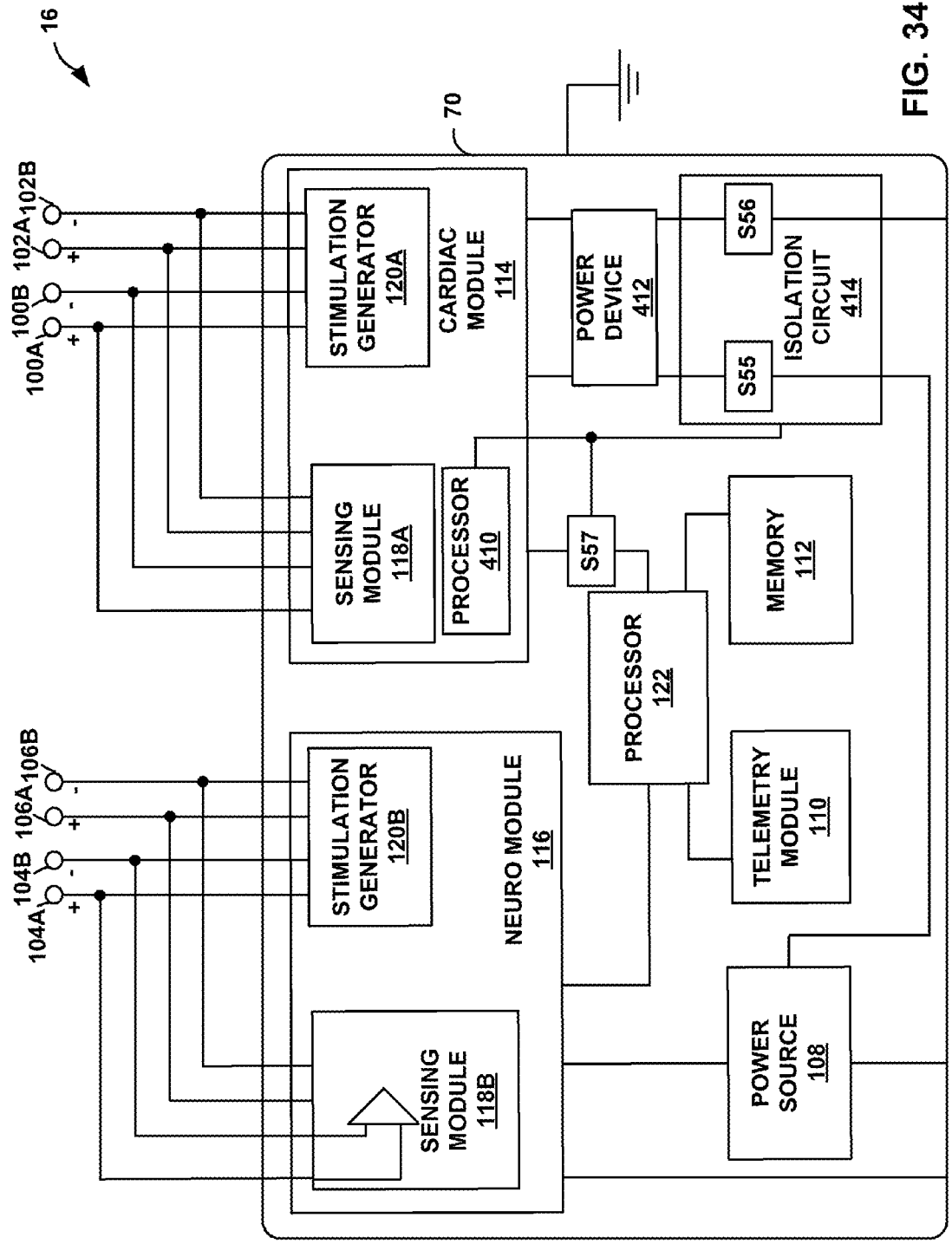

ISOLATION OF SENSING AND STIMULATION CIRCUITRY

This application claims the benefit of U.S. Provisional Application No. 61/110,428, entitled, "ISOLATION OF SENSING AND STIMULATION CIRCUITRY," and filed on Oct. 31, 2008, and U.S. Provisional Application No. 61/148,852, entitled, "ISOLATION OF SENSING AND STIMULATION CIRCUITRY," and filed on Jan. 30, 2009, the entire contents of each incorporated herein by reference.

TECHNICAL FIELD

The disclosure relates to implantable medical devices, and, more particularly, implantable medical devices providing multiple therapy and/or sensing functions.

BACKGROUND

A wide variety of implantable medical devices (IMDs) for delivering a therapy and/or sensing a physiologic condition of a patient have been clinically implanted or proposed for clinical implantation in patients. Such IMDs may deliver therapy and/or monitor the heart, muscle, nerves, brain, stomach or other organs. In some cases, the IMDs deliver electrical stimulation therapy to the patient and/or monitor physiological signals of the patient via one or more electrodes or sensor elements, at least some of which may be included as part of one or more elongated implantable medical leads coupled to the IMD. Implantable medical leads may be configured to allow electrodes or sensors to be positioned at desired locations for delivery of stimulation or sensing physiological signals. In some cases, electrodes or sensors may be positioned on an IMD housing as an alternative or in addition to electrodes or sensors deployed on one or more leads.

For example, implantable cardiac devices, such as cardiac pacemakers or implantable cardioverter defibrillators, provide therapeutic electrical stimulation to the heart by delivering electrical therapy signals such as pulses or shocks for pacing, cardioversion or defibrillation via electrodes of one or more implantable leads. In some cases, such an IMD may sense intrinsic depolarizations of the heart, and control the delivery of the electrical therapy signals to the heart based on the sensing. When an abnormal rhythm is detected, such as bradycardia, tachycardia or fibrillation, an appropriate electrical therapy (e.g., in the form of pulses or shocks) may be delivered to restore the normal rhythm. For example, in some cases, the IMD may deliver pacing, cardioversion or defibrillation therapy to the heart of the patient upon detecting ventricular tachycardia, and deliver cardioversion or defibrillation therapy to a patient's heart upon detecting ventricular fibrillation.

SUMMARY

This disclosure describes techniques for isolating two or more therapy and/or sensing modules of an implantable medical device (IMD). In particular, this disclosure describes a number of techniques for isolating the first module from the second module to reduce or eliminate crosstalk between the therapy and/or sensing modules of the IMD. The isolation techniques of this disclosure may break a direct electrical path or an indirect electrical path between the first module and the second module, e.g., through a common component. An isolation circuit may, for example, be placed somewhere in the electrical path between the modules. As such, the crosstalk, or at least a portion of the crosstalk, generated by electrical stimulation does not have a direct electrical path or has a relatively weak path of inconsequential impact via which to reach the other one of the modules.

In one aspect, the disclosure is directed to an implantable medical device (IMD) comprising a housing, a cardiac module, in the housing, configured to deliver electrical stimulation therapy to a patient, a power source that couples to the cardiac module and is configured to provide power to the cardiac module, at least one isolation circuit that couples to the power source, and a neurostimulation module, in the housing, that couples to the power source via the at least one isolation circuit and is configured to deliver electrical stimulation therapy to the patient or sense a physiological condition of the patient. The at least one isolation circuit is configured to electrically isolate the power source from the neurostimulation module to reduce common-mode interference on the neurostimulation module. The common-mode interference is caused by the cardiac module delivering electrical stimulation therapy to the patient.

In another aspect, the disclosure is directed to an implantable medical device (IMD) comprising a housing, a first module, in the housing, configured to deliver electrical stimulation therapy to a patient, a power source that couples to the first module and is configured to provide power to the first module, at least one isolation circuit that couples to the power source, and a second module, in the housing, that couples to the power source via the at least one isolation circuit and is configured to deliver electrical stimulation therapy to the patient or sense a physiological condition of the patient. The at least one isolation circuit is configured to electrically isolate the power source from the second module to reduce at least one of common-mode interference and shunt current on the second module. The at least one of common-mode interference and shunt current is caused by the first module delivering electrical stimulation therapy to the patient.

In another aspect, the disclosure is directed to a method comprising delivering, via a first module within a housing of an implantable medical device (IMD), electrical stimulation therapy to a patient, wherein the first module is powered via a power source, delivering, via a second module within the housing of the IMD, electrical stimulation therapy to the patient or sensing, via the second module within the housing of the IMD, a physiological condition of the patient, wherein the second module is powered via at least one isolation circuit that couples to the power source, and isolating the power source from the second module via the at least one isolation circuit to reduce at least one of common-mode interference and shut current on the second module. Delivering electrical stimulation via the first module causes the at least one of common-mode interference and shunt current.

In another aspect, the disclosure is directed to an implantable medical device (IMD) comprising a housing, a first means, in the housing, for delivering electrical stimulation therapy to a patient, wherein the first means is powered via a power source, and a second means, in the housing, for delivering a electrical stimulation therapy to the patient or sensing a physiological condition of the patient, wherein the second means is powered via at least one means for isolating that couples to the power source. The means for isolating isolates the power source from the second means to reduce at least one of common-mode interference and shunt current on the second means. Delivering electrical stimulation via the first means causes the at least one of common-mode interference and shunt current.

In another aspect, the disclosure is directed to an implantable medical device (IMD) comprising a housing, a cardiac module, in the housing, configured to deliver electrical stimulation therapy to a patient, a power source that couples to the cardiac module and is configured to provide power to the cardiac module, at least one isolation circuit that couples to the power source, wherein the at least one isolation circuit comprises a first and a second switch coupled to a first and a second input line, respectively, wherein the first input line and the second input line are coupled to the power source and a ground of the power source, respectively, a capacitor circuit that is coupled to the first and second switch, a third and fourth switch, wherein the capacitor circuit is coupled to the third and fourth switch, and wherein the third switch is further coupled to the first switch and the fourth switch is further coupled to the second switch, a capacitor, wherein the capacitor is coupled to the third and fourth switch, and a fifth and sixth switch coupled to a first and second output line, respectively, wherein the capacitor is coupled to the fifth and sixth switch, wherein, in a first state, the first and second switches are closed and the third, fourth, fifth, and sixth switches are opened to charge the capacitor circuit, in a second state, the first, second, fifth and sixth switches are opened and the third and fourth switches are closed to discharge the capacitor circuit and charge the capacitor, and, in a third state, the third and fourth switches are opened and the first, second, fifth, and sixth switches are closed to provide isolated power to the neurostimulation module coupled to the isolation circuit, wherein after the capacitor discharges, the first and second switches are opened and the third and fourth switches are closed to charge the capacitor and provide isolated power, and wherein after the capacitor charges, the third and fourth switches are opened and the first and second switches are closed to provide power on the first and second output line, and a neurostimulation module, in the housing, that couples to the first output line and the second output line of the at least one isolation circuit to receive power and is configured to deliver electrical stimulation therapy to the patient or sense a physiological condition of the patient, wherein the at least one isolation circuit is configured to electrically isolate the power source from the neurostimulation module to reduce at least one of common-mode interference and shunt current on the neurostimulation module, and wherein the at least one of common-mode interference and shunt current is caused by the cardiac module delivering electrical stimulation therapy to the patient.

In another aspect, the disclosure is directed to an implantable medical device (IMD) comprising a housing, a processor, a cardiac module, in the housing, configured to deliver electrical stimulation therapy to a patient, a power source that couples to the cardiac module and is configured to provide power to the cardiac module, at least one isolation circuit that couples to the power source, wherein the at least one isolation circuit comprises an oscillator coupled to a first and a second input line and further coupled to the processor, and configured to generate a first oscillating pulse that comprises data provided by the processor, wherein the first and the second input line are coupled to the power source and a ground of the power source, a transformer coupled to the oscillator and configured to transform the first oscillating pulse to a second oscillating pulse, a data demodulator coupled to the transformer and configured to provide data between the cardiac and neurostimulation modules, a rectifier coupled to the transformer and configured to rectify the second oscillating pulse, and a capacitor coupled to the rectifier and configured to generate an isolated direct current (DC) voltage across a first and second output line, a neurostimulation module, in the housing, that couples to the first and second output line of the at least one isolation circuit and is configured to deliver electrical stimulation therapy to the patient or sense a physiological condition of the patient, wherein the at least one isolation circuit is configured to electrically isolate the power source from the neurostimulation module to reduce at least one of common-mode interference and shunt current on the neurostimulation module, and wherein the at least one of common-mode interference and shunt current is caused by the cardiac module delivering electrical stimulation therapy to the patient.

In another aspect, the disclosure is directed to an implantable medical device (IMD) comprising a first module configured to deliver electrical stimulation therapy to a patient, a second module configured to deliver electrical stimulation therapy to the patient or senses a physiological condition of the patient via at least one electrode, wherein the first module and second module share at least one common component, and at least one isolation circuit that couples the second module to the at least one electrode and is configured to reduce at least one of common-mode interference and shunt current on the second module caused by the delivery of electrical stimulation by the first module, wherein the at least one isolation circuit is configured to isolate the electrical stimulation delivered by the first module from the second module.

In another aspect, the disclosure is directed to a method comprising delivering, via a first module within an implantable medical device (IMD), electrical stimulation therapy to a patient, delivering, via a second module within an IMD, electrical stimulation therapy to the patient or sensing a physiological condition of the patient, wherein the first module and second module share at least one common component, and wherein the second module is configured to deliver electrical stimulation therapy to the patient or sense the physiological condition of the patient via at least one electrode, and isolating the electrical stimulation delivered by the first module from the second module via at least one isolation circuit, wherein the isolation circuit couples the second module to the at least one electrode and is configured to reduce at least one of common-mode interference and shunt current on the second module caused by the delivery of electrical stimulation by the first module.

In another aspect, the disclosure is directed to a An implantable medical device (IMD) comprising a first means for delivering electrical stimulation therapy to a patient, a second means for delivering electrical stimulation therapy to the patient or sensing a physiological condition of the patient via at least one electrode, wherein the first means and second means share at least one common component, and means for isolating the electrical stimulation delivered by the first means from the second means, wherein the means for isolating couples the second means to the at least one electrode and is configured to reduce at least one of common-mode interference and shunt current on the second means caused by the delivery of electrical stimulation by the first means.

The details of one or more examples are set forth in the accompanying drawings and the description below. Other features, objects, and advantages of the techniques of this disclosure will be apparent from the description and drawings, and from the claims.

BRIEF DESCRIPTION OF DRAWINGS

FIG. 33 is a functional block diagram of another example configuration of an IMD comprising isolation circuits to reduce or eliminate commonality.

FIG. 34 is a functional block diagram of another example configuration of an IMD comprising isolation circuits to reduce or eliminate commonality.

DETAILED DESCRIPTION

Figure 1:
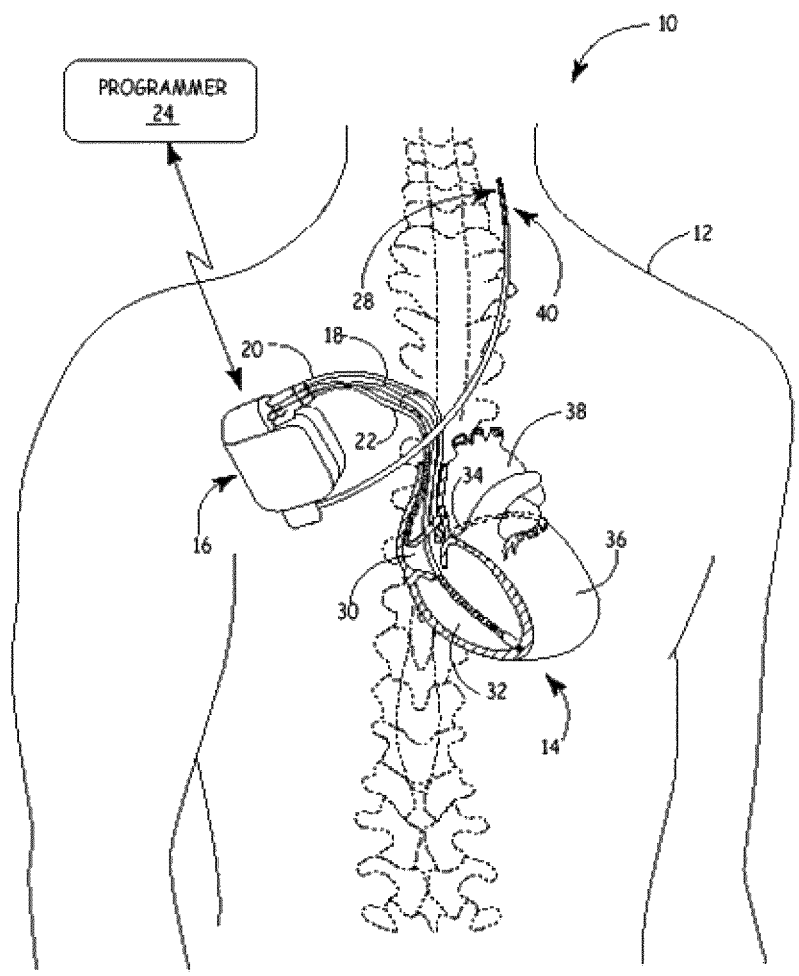
FIG. 1 is a conceptual diagram illustrating an IMD forming an example therapy system that may be used to provide therapy to patient.

Some IMDs may include a neurostimulation device in addition to the cardiac stimulation device. As one example, a medical device system may include a spinal cord stimulator and an implantable atrial defibrillator, whereby the spinal cord stimulator may deliver stimulation to reduce pain associated with delivery of defibrillation shocks. As another example, a medical device system may include a neurostimulation device to provide parasympathetic nerve stimulation in an attempt to either slow intrinsic heart rate or decrease susceptibility to arrhythmias or premature ventricular contractions (PVC) to facilitate anti-tachyarrhythmia treatments, such as antitachycardia pacing, cardioversion or defibrillation. In some cases, a neurostimulation device and a cardiac stimulation device may be provided may be provided, at least in part, within the same IMD housing.

This disclosure describes techniques for isolating two or more therapy and/or sensing modules of an implantable medical device (IMD). For example, the IMD may include a first module for delivering therapy to a patient and/or sensing a physiological condition of the patient and a second module for delivering therapy to a patient and/or sensing a physiological condition of the patient. In one instance, the first module may be a cardiac stimulation module for delivering therapy to and/or monitoring a heart of a patient and the second module may be a neurostimulation module for delivering therapy to and/or monitoring a tissue site of the patient. The techniques described in this disclosure should not be limited to such therapy and sensing modules of the IMD. The techniques may be utilized for isolating any energy (or therapy) delivery and/or sensing modules within the IMD.

The first and second modules of the IMD may interconnect via at least one common component of the IMD, e.g., a power source, a ground, a processor or other circuitry of the IMD such as wiring between the first and second modules. The interconnection between the first and second modules and the at least one other component of the IMD may be referred to as "commonality." The commonality results in an electrical path between the first and second modules, e.g., through one or more the common components. The electrical path may be a direct electrical path or an indirect electrical path, e.g., the direct electrical path or indirect electrical path may comprise an electrical path with relatively low impedance. When the first module delivers electrical therapy or stimulation (e.g., in the form of pulses or other electrical signals), the commonality between the first and second modules of the IMD may result in crosstalk on the second module, e.g., in the form of common-mode interference or shunt current. In other words, the crosstalk may interfere with the second module due to the electrical path through the one or more common components. The opposite is also true, e.g., the commonality between the first and second modules of the IMD may result in crosstalk on the first module when the second module delivers electrical therapy or stimulation. The crosstalk may result in incorrect detection of a physiological condition, undesirable delivery of therapy to the patient, damage to the first or second module, or the like. Excessive crosstalk may be the result of the excessive common mode signal, which may not be sufficiently cancelled due to limitations of the common mode rejection of the input circuits. Techniques of this disclosure may reduce or eliminate commonality in order to reduce the intensity of the common mode signal, thereby allowing the common mode rejection to sufficiently minimize the crosstalk.

To prevent or reduce these inadvertent and undesirable effects, this disclosure describes a number of techniques for isolating the first module from the second module. The isolation techniques of this disclosure may reduce and, in some instances, eliminate the commonality between the first and second modules and the at least one other component of the IMD. By eliminating the commonality between the first and second modules, the isolation circuit in effect reduces or eliminates crosstalk, e.g., in the form of common-mode interference or shunt current. In other words, the isolation circuits described in this disclosure may break the electrical path between the first module, the common component and the second module. As such, the crosstalk or at least a portion of the crosstalk does not have an electrical path via which to reach the other one of the modules. For example, the isolation circuit may break the direct electrical path or provide enough resistance or impedance to generate a weak electrical path with a relatively weak path of inconsequential impact.

As one non-limiting example of common-mode interference, to sense a signal via a pair of electrodes coupled to the cardiac module, an amplifier within the cardiac module measures the voltage at a first electrode of the electrode pair with respect to ground which may be provided by a reference electrode, and measures the voltage at a second electrode of the electrode pair with respect to ground which may be provided by the reference electrode. The amplifier then subtracts the two voltages to generate a sense signal.

If the cardiac module and neuro module share a common component, e.g. share the same ground, a stimulation signal generated by the neuro module via electrodes coupled to the neuro module imposes a relatively high common voltage on the first and second electrodes of the electrode pair. The amplifier within the cardiac module may be unable to process signals from the electrode pair that include a relatively high common voltage, causing the amplifier to perform less desirably. As described in this disclosure, the term common-mode interference refers to the relatively high common voltage that is imposed on each electrode of an electrode pair.

Stated another way, if the neuro module and cardiac module did not share a common component, e.g. share the same ground, a stimulation generated by the neuro module may not spread far from the electrodes coupled to the neuro module, and may only generate a differential signal on the electrodes coupled to the cardiac module. The cardiac module may be capable of withstanding the differential signal caused by the stimulation generated by the neuro module.

It should be noted that the cardiac module's ability to attenuate common mode signals is limited. Hence, a large common mode signal may be attenuated, but not attenuated sufficiently to reduce its intensity to a tolerable level. Sufficiently reducing or eliminating the commonality between the cardiac module and neuro module may reduce the intensity of the common mode signal such that the cardiac module is able to sufficiently attenuate the common mode signal.

However, if the cardiac module and neuro module share a common component, e.g. share the same ground, then a stimulation signal generated by the neuro module may spread from the electrodes coupled to the neuro module to the electrodes coupled to the cardiac module because the stimulation signal generated by the neuro module is referenced to the same ground as the cardiac module. Since the stimulation signal spreads to the electrodes coupled to the cardiac module, the stimulation signal generates a common voltage on each electrode of the electrode pair, which is referred to as common-mode interference. The amplifier within the cardiac module used to sense signals via the electrode pair coupled to the cardiac module may not be able to withstand the common voltage, resulting in less than desirable sense signals.

Accordingly, various isolation circuits are presented throughout this disclosure that reduce or eliminate the commonality between the neuro and cardiac modules. By reducing or eliminating the commonality, a stimulation signal generated by either the cardiac module or neuro module, a common voltage may not be imposed on the other module, allowing the other module to properly sense physiological conditions.

In some examples, the isolation circuits may sufficiently reduce or eliminate commonality between components shared by both the neuro and cardiac modules, e.g., power source, ground, one or more processors, or shared wiring. In this manner, stimulation signals generated by one module may not impose a common voltage on the other module. In some examples, the isolation circuits may be coupled to stimulation and/or sensing electrodes of the neuro module and/or cardiac module. In these examples, the stimulation generated by one of the modules is electrically isolated from the other module. In these examples, though there may be some commonality between components shared by both the neuro and cardiac modules, the commonality between the output of one of the modules and the input of the other module may be sufficiently reduced or eliminated such that the stimulation signal generated by one module may not impose a common voltage on the other module.

Accordingly, as used in this disclosure, the term commonality should be interpreted to mean a relatively low impedance path between the two modules. The relatively low impedance path may include paths within the medical device that includes the two modules. Or, the relatively low impedance path may include a path from the output of one of the modules into the input of the other module where the two modules share common components. To sufficiently reduce or eliminate the commonality between the two modules, various aspects of this disclosure cause a break in the commonality between the two modules. Accordingly, there may no longer be a low impedance path between the two modules. Instead, an electrical path between the two modules may be high impedance. The electrical path may include an electrical path between shared components of the two modules. The electrical path may also include an electrical path between the output of one module and the input of the other module.

As noted above, the various isolation circuits described throughout this disclosure sufficiently reduce or eliminate the commonality between the two modules. Accordingly, the various isolation circuits may generate a relatively high impedance path between the two modules. In some examples, the isolation circuits may generate the relatively high impedance path between shared components of the two modules. In some examples, the isolation circuits may generate a relatively high impedance path between the output of one module and the input of the other module even when the two modules share common components. In some examples, the various isolation circuits may generate the relatively high impedance path between shared components of the two modules and generate the relatively high impedance path between the output of one module and the input of the other module.

FIG. 1 is a conceptual diagram illustrating an example therapy system 10 that may be used to provide therapy to patient 12. Patient 12 ordinarily, but not necessarily, will be a human. Therapy system 10 includes implantable medical device (IMD) 16, which is coupled to leads 18, 20, 22, and 28 and programmer 24. IMD 16 may comprise a first therapy and/or sensing module and a second therapy and/or sensing module. In the example illustrated in FIG. 1, the first therapy and/or sensing module may be a neuro module and the second therapy and/or sensing module may be a cardiac module (neither of which are shown in FIG. 1). In other words, the implantable medical device may include the neuro module and the cardiac module, at least in part, within a common housing of IMD 16. Although described in the context of a cardiac module and a neuro module, the techniques of this disclosure should not be limited to such therapy/sensing modules within IMD 16. The cardiac module may provide cardiac stimulation and/or therapy, while the neuro module may provide neurostimulation and/or therapy. The techniques may be utilized for isolating any two or more therapy delivery and/or sensing modules within IMD 16.

The cardiac module may include, for example, an implantable pacemaker, cardioverter-defibrillator, combined pacemaker-cardioverter-defibrillator, implantable hemodynamic monitor, implantable cardiac monitor, implantable loop recorder that provides electrical stimulation therapy to heart 14 of patient 12 via electrodes coupled to one or more of leads 18, 20, and 22 and/or senses cardiac signals via one or more of leads 18, 20, and 22. Thus, the cardiac module of IMD 16 is coupled to leads 18, 20 and 22. In some cases, stimulation or sensing may also be performed via a combination of one or more electrodes on leads 18, 20, 22 and one or more electrodes on a housing, or case, of IMD 16. In some examples, the cardiac module may deliver pacing pulses, but not cardioversion or defibrillation shocks, while in other examples, the cardiac module may deliver cardioversion or defibrillation shocks, but not pacing pulses. In addition, in further examples, the cardiac module may deliver pacing pulses, cardioversion shocks, and defibrillation shocks. In other examples, the cardiac module may provide cardiac resynchronization therapy (CRT) in addition to or instead of the other therapies described above. Alternatively, or additionally, the cardiac module may also include circuitry for sensing cardiac signals from heart 14 of patient 12.

Leads 18, 20, 22 extend into heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. As shown in FIG. 1, the cardiac module is coupled to three leads, e.g. leads 18, 20, and 22. However, in some aspects, the cardiac module may be coupled to more or fewer leads. In other examples, the cardiac module of IMD 16 may deliver electrical stimulation therapy to heart 14 by delivering stimulation to an extravascular tissue site in addition to or instead of delivering stimulation via electrodes of intravascular leads 18, 20, 22.

The cardiac module of IMD 16 may sense electrical signals attendant to the depolarization and repolarization of heart 14 via electrodes (not shown in FIG. 1) coupled to at least one of the leads 18, 20, 22. In some examples, the cardiac module provides pacing pulses to heart 14 based on the electrical signals sensed within heart 14. These electrical signals sensed within heart 14 may also be referred to as cardiac signals. The configurations of electrodes used by the cardiac module for sensing and therapy delivery may be unipolar or bipolar. The cardiac module may also provide defibrillation therapy and/or cardioversion therapy via electrodes located on at least one of the leads 18, 20, 22. In addition, a portion of the housing may be used as an electrode for providing defibrillation therapy and/or cardioversion therapy. For example, the cardiac module may detect arrhythmia of heart 14, such as fibrillation of ventricles 32 and 36, and deliver defibrillation therapy to heart 14 in the form of electrical shocks. In some examples, the cardiac module may be programmed to deliver a progression of therapies, e.g., pulses with increasing energy levels, until a fibrillation of heart 14 is stopped. The cardiac module may detect fibrillation employing one or more fibrillation detection techniques known in the art. In some instances, the cardiac module of IMD 16 may not provide any stimulation. In further instances, the neuro module of IMD 16 may include both sensing and therapy delivery functionality.

The neuro module may be any suitable circuitry for generating electrical stimulation that may be delivered to a tissue site of patient 12 via electrodes of lead 28. As such, the neuro module of IMD 16 is coupled to lead 28, which carries one or more electrodes. In some cases, neuro module also may sense physiological signals. The tissue site of patient 12 may be a nerve, e.g., vagal stimulation via the jugular vein, or other extravascular tissue site of patient 12, e.g., proximate a vagus nerve, or proximate a spinal cord or heart 14 of patient 12. In some examples, the neuro module may deliver electrical stimulation that is delivered to peripheral nerves that innervate heart 14, or fat pads on heart 14 that may contain nerve bundles. The neuro stimulator may deliver stimulation to an extravascular tissue site and/or tissue proximate a nerve via lead 28, which may or may not be extravascular. That is, in some cases, the tissue proximate the nerve may be an extravascular tissue site. In other cases, lead 28 may be positioned within vasculature and provide stimulation to a tissue site proximate a nerve through the wall of the vein, artery, or other vasculature (not shown). In addition, the extravascular tissue site may or may not be proximate a nerve. In the example shown in FIG. 1, electrodes of lead 28 are positioned at a distal end of the lead to deliver electrical stimulation to a vagus nerve (not shown in FIG. 1) of patient 12. The stimulation delivered by the neuro module or cardiac module may take the form of stimulation pulses or continuous waveforms, and may be characterized by controlled voltage levels or controlled current levels, as well as selected pulse widths and pulse rates in the case of stimulation pulses.

In some examples, delivery of electrical stimulation to a tissue site proximate a nerve or a nonmyocardial tissue site that may not be proximate a nerve may help modulate an autonomic nervous system of patient 12. In some examples, the neuro module may deliver electrical stimulation therapy to a nerve of patient 12 via a lead implanted within vasculature (e.g., a blood vessel) of patient 12. In some examples, the neuro module may deliver electrical stimulation that is delivered to peripheral nerves that innervate heart 14, or fat pads on heart 14 that may contain nerve bundles, as discussed above. Stimulation may be delivered to extravascular tissue sites, for example, when lead 28 is not implanted within vasculature, such as within a vein, artery or heart 14. In other examples, stimulation may be delivered to a nonmyocardial tissue site via electrodes of an intravascular lead that is implanted within vasculature. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. The nonmyocardial tissue site may include extravascular tissue sites or intravascular tissue sites.

Figure 2:
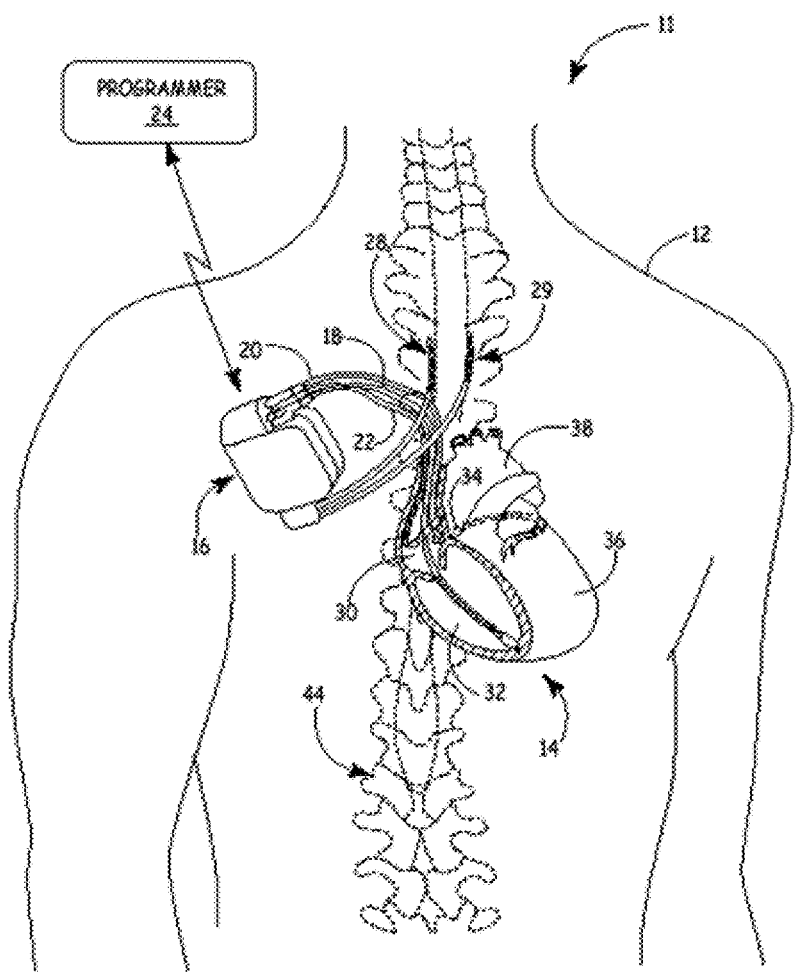
FIG. 2 is a conceptual diagram illustrating an IMD forming another example therapy system.

In the example of FIG. 1, the neuro module of IMD 16 provides a programmable stimulation signal (e.g., in the form of electrical pulses or a continuous signal) that is delivered to target stimulation site 40 by implantable medical lead 28, and more particularly, via one or more stimulation electrodes (not shown in FIG. 1) carried by lead 28. The neuro module may also be referred to as a signal generator, stimulation generator or an electrical stimulator. Furthermore, in some examples, the neuro module may be coupled to two or more leads, e.g., for bilateral or multi-lateral stimulation, e.g., as illustrated in FIG. 2.

Although the neuro module of IMD 16 is sometimes referred to as a "neurostimulator" and as delivering neurostimulation pulses in this disclosure, in other examples, the neuro module may deliver other types of electrical stimulation to any suitable tissue site within patient 12, which may or may not be proximate a nerve. In some examples, lead 28 may also carry one or more sense electrodes to permit the neuro module to sense electrical signals, e.g., neurological signals, from target stimulation site 40. In this case, the neuro module of IMD 16 may not provide any stimulation. In further instances, the neuro module of IMD 16 may include both sensing and therapy delivery functionality.

In some examples, the neuro module and cardiac module of IMD 16 may provide therapy to patient 12 in conjunction with one another. For example, delivery of electrical stimulation by the neuro module within IMD 16 to one or more extravascular target tissue sites proximate to a nerve, nerve site, cardiac fat pad, or another extravascular target tissue site (e.g., tissue site that is not implanted within heart 14 or within an artery or other vasculature of patient 12) may provide cardiac benefits to patient 12. For example, delivery of electrical stimulation to the extravascular tissue site may help reduce or eliminate cardiovascular conditions such as tachycardia, unhealthy cardiac contractions, brachycardia, ischemia, inefficient heart pumping, inefficient collateral circulation of heart 14 or cardiac muscle trauma. In addition, delivery of electrical stimulation by the neuro module may augment antitachycardia pacing by the cardiac module, provide back-up therapy to the cardiac module, or facilitate post-shock recovery of heart 14. In other examples, the neuro module may deliver electrical stimulation to patient 12 independently of the electrical stimulation delivered by the cardiac module.

In the example shown in FIG. 1, target stimulation site 40 may be a parasympathetic nerve, such as a vagus nerve, of patient 12. Stimulation of a parasympathetic nerve of patient 12 may help slow intrinsic rhythms of heart 14 or decrease susceptibility to arrhythmias or PVC of heart 14 which may both facilitate antitachyarrhythmia therapy (e.g., antitachycardia pacing, cardioversion or defibrillation) delivered by the cardiac module. For example, stimulation of a sympathetic nerve of patient 12 may help reduce the incidence of tachyarrhythmia of heart 14.

In other examples, electrodes of lead 28 may be positioned to deliver electrical stimulation to any other suitable nerve, organ, muscle or muscle group in patient 12, which may be selected based on, for example, a therapy regimen selected or prescribed for a particular patient. In some examples, the neuro module may deliver electrical stimulation to other parasympathetic nerves, baroreceptors, the carotid sinus or a cardiac branch of the vagal trunk of patient 12 in order to facilitate the delivery of therapy by the cardiac module.

As another example, as shown in FIG. 2, lead 28 to which the neuro module of IMD 16 is connected may be positioned to deliver electrical stimulation to spinal cord 44 of patient 12. Stimulation of spinal cord 44, nerves branching therefrom, or tissue site adjacent the nerves by the neuro module may help prevent or mitigate occurrences of tachyarrhythmias and may reduce the level of need of the cardiac therapy, such as pacing, cardioversion or defibrillation, delivered by the cardiac module. In this way, the cardiac module and neuro module may operate in conjunction with each other to help prevent arrhythmias of heart 14 of patient 12, as well as to terminate detected arrhythmias.

In the example shown in FIG. 2, a therapy system 11 includes a neuro module within IMD 16 is coupled to two leads 28, 29 to provide bilateral stimulation of spinal cord 44. In other examples, the neuro module of IMD 16 may be coupled to more than two leads. Leads 28, 29 may be introduced into spinal cord 44 via the thoracic column or near the lumbar region. Electrodes of leads 28, 29 may be positioned at distal ends of the leads within an intrathecal space or epidural space of spinal cord 44, or, in some examples, adjacent nerves that branch off of spinal cord 44. In some examples, leads 28, 29 are implanted within patient 12 and positioned such that electrodes of leads 28, 29 deliver electrical stimulation to locations proximate to the T1 to T6 thoracic vertebrae of the patient's vertebral column. For example, electrodes of at least one of the leads 28, 29 may span the T3 to T6 thoracic vertebrae or deliver electrical stimulation to a tissue site proximate at least one of the T3 to T6 thoracic vertebrae. In other examples, leads 28, 29 may be implanted to deliver electrical stimulation to other regions proximate or within spinal cord 44, such as over or near other vertebrae.

In other examples, the neuro module may deliver electrical stimulation to patient 12 independently of the electrical stimulation delivered by the cardiac module. For example, as shown in FIG. 2, leads 28, 29 carry electrodes that are placed adjacent to the target tissue of spinal cord 44. In particular, leads 28, 29 may be implanted in the epidural space adjacent spinal cord 44, and coupled to the neuro module within IMD 16. In the example of FIG. 2, stimulation energy may be delivered to spinal cord 44 to eliminate or reduce pain perceived by patient 12. However, the neuro module may be used with a variety of different therapies, such as peripheral nerve stimulation (PNS), peripheral nerve field stimulation (PNFS), deep brain stimulation (DBS), cortical stimulation (CS) and the like. The stimulation may be configured to alleviate a variety of symptoms or conditions such as chronic pain, tremor, Parkinson's disease, or epilepsy.

Accordingly, in some aspects, the cardiac module and the neuro module within IMD 16 may function in conjunction with one another to provide effective cardiac therapy to patient 12. In some other aspects, the cardiac module and neuro module may function independently of one another to provide therapy to patient 12. For example, if patient 12 suffers from a cardiac condition and neurological condition, the cardiac module and neuro module may function independently to alleviate the cardiac and neurological conditions. Moreover, though IMD 16 is described as providing therapy for cardiac and neurological conditions, aspects of this disclosure are not so limited. In some aspects, IMD 16 may provide electrical stimulation to provide relief from urinary or fecal incontinence, sexual dysfunction, obesity, or gastroparesis, as well as provide relief for cardiac or neurological conditions or both. Additionally, aspects of this disclosure may be used to provide isolation between a therapy delivery module of IMD 16 and other component of IMD 16, such as a telemetry module. However, for purposes of illustration, reference will be made to the neuro module and cardiac module within IMD 16.

The cardiac module and the neuro module of IMD 16 may interconnect with at least one common component of the IMD. The interconnection between the cardiac module, the neuro module and the at least one other component of IMD 16 may be referred to as "commonality" between the cardiac module and the neuro module. The commonality results in an electrical path (direct or indirect) between the cardiac and neuro modules, e.g., through the common component to which the neuro and cardiac module interconnect. For example, the cardiac module and the neuro module may reference a common ground (e.g., both be coupled to a housing or case of IMD 16), couple to a common power supply, couple to a common processor, or the like. When the cardiac module or the neuro module delivers electrical therapy or stimulation (e.g., in the form of pulses or other electrical signals) to patient 12, the commonality between the cardiac module and the neuro module of IMD 16 may cause inadvertent effects on the module not delivering the therapy. In other words, the delivery of the electrical stimulation or therapy may result in crosstalk via the electrical path through the common component, which may interfere with the second module due to the electrical path through the common component.

As described in more detail below, the commonality may result from the neuro module and cardiac module sharing common components. In some other aspects, the commonality may result from the neuro module and cardiac module sharing another common component or the common power source as well as the other component or processing circuitry. In the case of a common power source, for example, the power source may be a voltage source such as a battery. In one aspect, a positive end of the battery may couple to the power input of the neuro module and cardiac module (or components of the neuro and cardiac module), and a negative end of the battery may couple to the case or housing of IMD 16. The case or housing of IMD 16 may, in this case, function as a ground, a common or a reference. The case of IMD 16 may comprise a conductive material, such as titanium. In other instances, the case may not be ground but is indirectly tied to ground (or common) through one or more components of IMD 16. In some aspects, the cardiac module and neuro module of IMD 16 may share a common ground that is not the case or housing of IMD 16. In other words, the common ground may not directly be the case or housing of IMD 16. To allow proper current flow, e.g., a complete circuit, the neuro module and cardiac module are also referenced to the ground. In the example described above, the neuro module and the cardiac module may be referenced to the case or housing of IMD 16. For example, various circuitry within the neuro module and cardiac module receive power from the common power source and reference to the same ground as the power source. In other examples, the neuro module and cardiac module of IMD 16 may receive power from different power sources, but reference the same ground (e.g., the case or housing of IMD 16). In some examples, the cardiac module and neuro module may be coupled to different power sources, but each of the power sources may be coupled to same ground, e.g., the case of IMD 16.

The commonality between the cardiac module and the neuro module may result in crosstalk between the modules in response to delivery of electrical stimulation. In one example, delivery of electrical stimulation or therapy may result in common-mode interference due to the commonality. Due to the shared or common ground, a stimulation signal generated by either the neuro module or cardiac module may impose a common voltage, e.g., common-mode signal or interference, on each electrode of a pair of electrodes coupled to the other module not delivering the therapy. The common-mode interference may affect the ability of the other module to sense a signal. This may be particularly true when the electrode pair is coupled to a differential amplifier and the common-mode signal is larger than the amplifier can accurately reject. For example, upon a stimulation generated by the neuro module of IMD 16 (e.g., via leads 28 or 29), common-mode interference may be imposed on to the cardiac module of IMD 16, e.g., sensing electrodes of the cardiac module, causing the cardiac module to sense arrhythmia when no arrhythmia actually exists. In response, the cardiac module may unnecessarily provide stimulation to heart 14 of patient 12 to correct the arrhythmia. This causes heart 14 to be stimulated even when heart 14 is functioning correctly. Alternatively, in response, the cardiac module may withhold stimulation when stimulation to heart 14 of patient 12 is necessary. The common-mode interference may cause incorrect sensing of heart 14, e.g., not sensing an R-wave. Not sensing the R-wave of heart 14 may cause the cardiac module to miss a ventricular tachycardia and/or ventricular fibrillation (VT/VF) episode, as one example.

As another example, delivery of electrical stimulation or therapy may result in shunt current due to the commonality. For example, an electrical therapy (e.g., defibrillation and/or cardioversion shock) generated by the cardiac module of IMD 16 may be sensed by electrodes of lead 28 or 29 coupled to the neuro module of IMD 16. The high voltage electrical therapy may be imposed upon the neuro module and induce shunt current through the case or housing of IMD 16, and/or electrodes of leads 28 or 29, coupled to the neuro device. The tissue through which the shunt current travels, e.g., the tissue between the electrodes of leads 28 or 29, may result in unnecessary and possible undesirable stimulation of the tissue. The shunt current may also cause a current to flow through leads 28 or 29 to the neuro module, creating stress on circuitry within the neuro module. Shunt current may also be generated in the cardiac module in response to stimulation from the neuro module.

Stated another way, as one example, the stimulation signal (e.g., defibrillation pulse) generated by the cardiac module generates a voltage that may be sensed by at least one electrode coupled to the neuro module. The cardiac module and the neuro module may be coupled to the same ground, e.g., the housing of the IMD that encloses the cardiac and neuro module. Because the cardiac and neuro module are coupled to the same ground, the defibrillation pulse may generate a relatively large voltage with respect to ground on the electrodes coupled to the neuro module. The large voltage may create a shunt current that flows through leads 28 or 29 to the neuro module. The shunt current is provided with a complete current path because the neuro module and cardiac module share a common component, e.g., share a common ground. In accordance with this disclosure, the various isolation circuits described herein reduce or eliminate the commonality between the neuro and cardiac modules creating a high impedance path for the shunt current.

As another example, the shunt current may also flow between electrodes. In some examples, leads 28 and 29 may comprise clamping structures between the electrodes coupled to leads 28 and 29. Examples of a clamping structure include a Zener diode, a silicone controlled rectifier (SCR), and the like. The clamping structures activate when the electrodes sense a high voltage to limit the voltage sensed by circuitry within the neuro module. Particularly, the clamping structures activate in response to a sensed high voltage and generate a voltage short across the electrodes. However, the activation of the clamping structures may have a potentially negative effect of providing a low impedance path for the shunt current to flow between the electrodes. Notably, clamping structures are provided as a non-limiting example. In some examples, leads 28 and 29 may not comprise clamping structures. Furthermore, examples of this disclosure may reduce or eliminate electrode-to-electrode shunt current. However, the shunt current that may flow from the leads into the neuro module may potentially place more stress on the neuro module and proximate tissue than the electrode-to-electrode shunt current. Accordingly, as described above, examples of this disclosure reduce or eliminate the shunt current that may flow into the neuro module caused by a stimulation generated by the cardiac module. Similarly, examples of this disclosure may reduce or eliminate the shunt current that may flow into the cardiac module caused by the stimulation generated by the neuro module.

In accordance with this disclosure, an isolation circuit is provided to reduce or eliminate the commonality between the neuro module and cardiac module. In some aspects, the isolation circuit may reduce and possibly remove the commonality between the neuro module and cardiac module at the stimulation output of either the neuro module, cardiac module or both. In other aspects, the isolation circuit may remove the commonality between the neuro module and cardiac module at the power input of either the neuro module, cardiac module or both. The isolation circuit may, for example, cause either the output of the neuro module or cardiac module or the power input of the neuro module or cardiac module such that the outputs of the neuro module and cardiac module or the power inputs of the neuro module or cardiac module no longer share a common ground or other common component of IMD 16. Because the neuro module and the cardiac module of IMD 16 no longer share a common ground or other common component of IMD 16, crosstalk, e.g., in the form of common-mode interference or shunt current, may be reduced and, possibly, eliminated. In other words, the isolation circuits described in this disclosure may break the electrical path between the first module, the common component and the second module. As such, the crosstalk or at least a portion of the crosstalk does not have an electrical path via which to reach the other one of the modules. In other words, the crosstalk does not have an appreciable electrical path via which to reach the other one of the modules. Thus, the electrical path is relatively weak, such that the crosstalk is appreciably reduced.

The values for the therapy parameters that define the electrical stimulation delivered by IMD 16 may be organized into a group of parameter values referred to as a "therapy program" or "therapy parameter set." "Therapy program" and "therapy parameter set" are used interchangeably throughout this disclosure. In the case of electrical stimulation, the therapy parameters may include an electrode combination, an amplitude, which may be a current or voltage amplitude, and, if IMD 16 delivers electrical pulses, a pulse width, and a pulse rate for stimulation signals to be delivered to the patient. An electrode combination may include a selected subset of one or more electrodes of leads 18, 20, 22, 28, and 29. The electrode combination may also refer to the polarities of the electrodes in the selected subset. By selecting particular electrode combinations, a clinician may target particular anatomic structures within patient 12. Electrode combinations may be configured as bipolar, multi-polar or unipolar arrangements. A unipolar arrangement may include, for example, an electrode on a lead and an electrode on a housing or "can" of IMD 16. In some cases, IMD 16 may deliver stimulation to patient 12 according to a program group that includes more than one therapy program.

A user, such as a patient, physician, technician, or other clinician, may interact with programmer 24 to communicate with the cardiac module and neuro module within IMD 16. For example, the user may interact with programmer 24 to retrieve physiological or diagnostic information from IMD 16. A user may also interact with programmer 24 to program IMD 16, e.g., select values for operational parameters of the cardiac module and neuro module, respectively.

For example, the user may use programmer 24 to retrieve information from the cardiac module regarding the rhythm of heart 14, trends therein over time, or tachyarrhythmia episodes. As another example, the user may use programmer 24 to retrieve information from the cardiac module regarding other sensed physiological parameters of patient 12, such as intracardiac or intravascular pressure, activity, posture, respiration, or thoracic impedance. As another example, the user may use programmer 24 to retrieve information from the cardiac module regarding the performance or integrity of the cardiac module or other components of system 10, such as leads 18, 20, and 22, or a power source of the cardiac module.

The user may use programmer 24 to program a therapy progression, select electrodes used to deliver defibrillation pulses, or select waveforms for the defibrillation pulse for the cardiac module within IMD 16. The user may also use programmer 24 to program aspects of other therapies provided by the cardiac module within IMD 16, such as cardioversion or pacing therapies. In some examples, the user may activate certain features of the cardiac module by entering a single command via programmer 24, such as depression of a single key or combination of keys of a keypad or a single point-and-select action with a pointing device.

As another example, the user may use programmer 24 to retrieve information from the neuro module regarding the performance or integrity of the neuro module or leads 28, 29, or a power source of the neuro module. With the aid of programmer 24 or another computing device, a user may select values for therapy parameters for controlling therapy delivery by the neuro module within IMD 16.

Programmer 24 may communicate with IMD 16 via wireless communication using any techniques known in the art. Examples of communication techniques may include, for example, low frequency inductive or radiofrequency (RF) telemetry, but other techniques are also contemplated. In some examples, programmer 24 may include a programming head that may be placed proximate to the patient's body near IMD 16 implant sites in order to improve the quality or security of communication between IMD 16 and programmer 24.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

Figure 3:
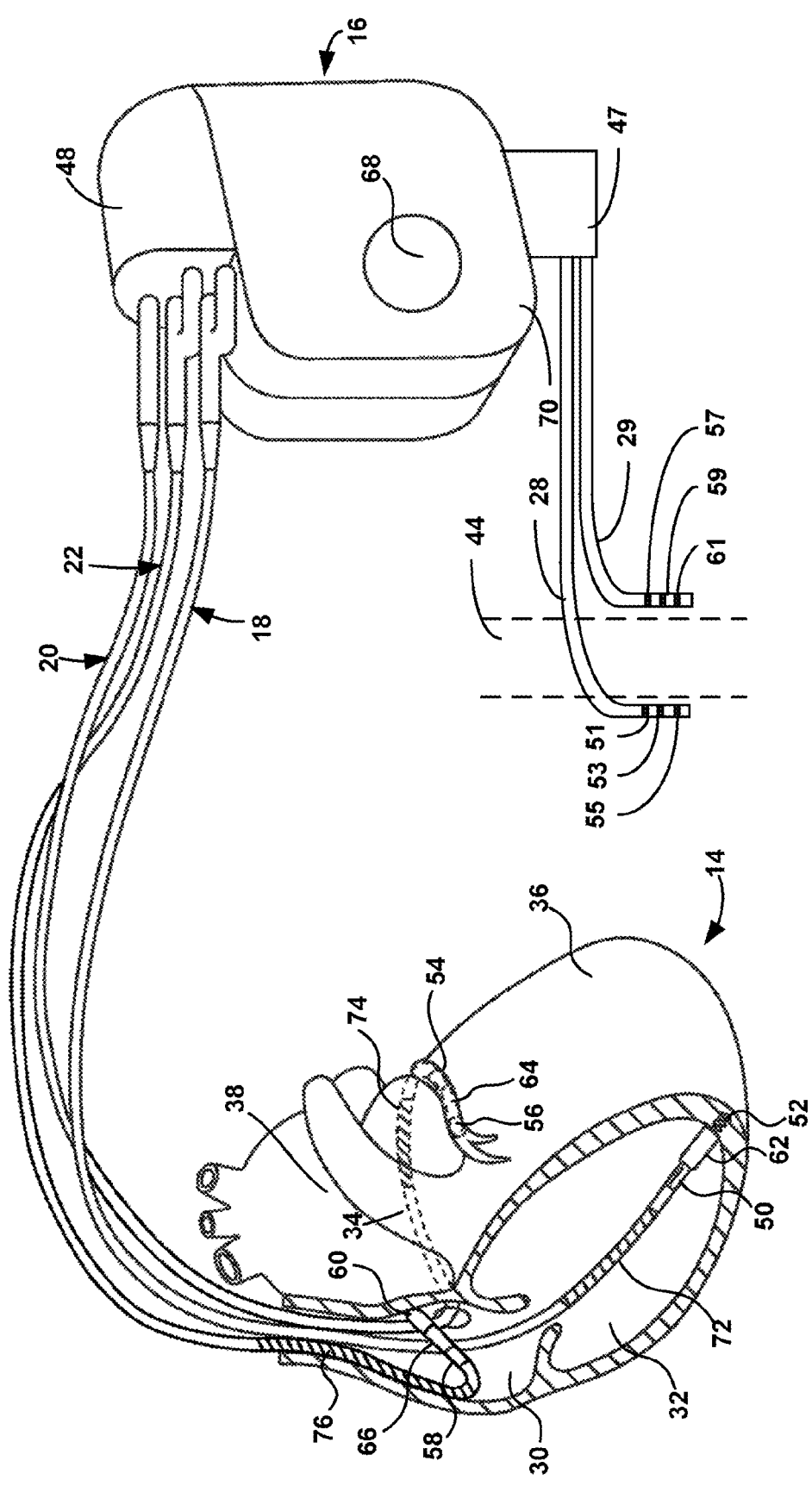
FIG. 3 is a conceptual diagram illustrating the IMD of FIGS. 1 and 2 and the respective leads in greater detail.

FIG. 3 is a conceptual diagram illustrating cardiac module within IMD 16 and leads 18, 20, 22, 28, and 29 of therapy system 11 in greater detail. Leads 18, 20, 22 may be electrically coupled to a stimulation generator, a sensing module, or other modules of a cardiac module within IMD 16 via connector block 48. Leads 28 and 29 may be coupled to a stimulation generator, a sensing module, or other modules of a neuro module within IMD 16 via connector block 47. As shown in FIG. 3, leads 18, 20, and 22 couple heart 14 of patient 12, and leads 28 and 29 couple to spinal cord 44 of patient 12. In some examples, proximal ends of leads 18, 20, 22, 28, and 29 may include electrical contacts that electrically couple to respective electrical contacts within respective connector blocks 47, 48. In addition, in some examples, leads 18, 20, 22, 28, and 29 may be mechanically coupled to respective connector blocks 47, 48 with the aid of set screws, connection pins or another suitable mechanical coupling mechanism.

Each of the leads 18, 20, 22, 28, and 29 includes an elongated insulative lead body, which may carry a number of concentric coiled conductors separated from one another by tubular insulative sheaths. In the illustrated example, bipolar electrodes 50 and 52 are located proximate to a distal end of lead 18. In addition, bipolar electrodes 54 and 56 are located proximate to a distal end of lead 20 and bipolar electrodes 58 and 60 are located proximate to a distal end of lead 22. Similarly, electrodes 51, 53, and 55 are located proximate to a distal end of lead 28, and electrodes 57, 59, and 61 are located proximate to a distal end of lead 29.

Electrodes 50, 54 and 58 may take the form of ring electrodes, and electrodes 52, 56 and 60 may take the form of extendable helix tip electrodes mounted retractably within insulative electrode heads 62, 64, and 66, respectively. Each of the electrodes 50, 52, 54, 56, 58, and 60 may be electrically coupled to a respective one of the coiled conductors within the lead body of its associated lead 18, 20, 22, and thereby coupled to respective ones of the electrical contacts on the proximal end of leads 18, 20 and 22. Similarly, electrodes 51, 53, 55, 57, 59, and 61 may comprise ring electrodes or other types of electrodes and electrically couple to a respective one of the coiled conductors within the lead body of its associated lead 28, 29.

Electrodes 50, 52, 54, 56, 58, and 60 may sense electrical signals attendant to the depolarization and repolarization of heart 14. The electrical signals are conducted to the cardiac module within IMD 16 via the respective leads 18, 20, 22. In some examples, the cardiac module also delivers pacing pulses via electrodes 50, 52, 54, 56, 58, and 60 to cause depolarization of cardiac tissue of heart 14. In some examples, as illustrated in FIG. 2, the cardiac module includes one or more housing electrodes, such as housing electrode 68, which may be formed integrally with an outer surface of hermetically-sealed housing 70 of IMD 16 or otherwise coupled to housing 70. As described above, housing 70 may provide the ground for the power source and the various components within the cardiac module and neuro module within IMD 16. In such cases, housing electrode 68 may couple shunt current or common mode interference to the neuro module in response to therapy delivered by the cardiac module. In some examples, housing electrode 68 is defined by an uninsulated portion of an outward facing portion of housing 70 of IMD 16. Other division between insulated and uninsulated portions of housing 70 may be employed to define two or more housing electrodes. In some examples, housing electrode 68 comprises substantially all of housing 70. Any of the electrodes 50, 52, 54, 56, 58, and 60 may be used for unipolar sensing or pacing in combination with housing electrode 68. As described in further detail with reference to FIG. 4, housing 70 may enclose a stimulation generator that generates cardiac pacing pulses and defibrillation or cardioversion shocks, as well as a sensing module for monitoring the patient's heart rhythm.

Electrodes 51, 53, 55, 57, 59, and 61 may provide stimulation to spinal cord 44 or alternatively sense signals proximate to spinal cord 44. The electrical signals are conducted to the cardiac module within IMD 16 via the respective leads 28 and 29. In some examples, the neuro module delivers stimulation pulses via electrodes 51, 53, 55, 57, 59, and 61 to cause stimulation on spinal cord 44. Electrodes 51, 53, 55, 57, 59, and 61 may be fabricated from any suitable electrically conductive material, such as, but not limited to, platinum, platinum alloy or other materials known to be usable in implantable neuro electrodes.

Leads 18, 20, 22 also include elongated electrodes 72, 74, 76, respectively, which may take the form of a coil. The cardiac module within IMD 16 may deliver defibrillation pulses to heart 14 via any combination of elongated electrodes 72, 74, 76, and housing electrode 68. Electrodes 68, 72, 74, 76 may also be used to deliver cardioversion pulses to heart 14. Electrodes 72, 74, 76 may be fabricated from any suitable electrically conductive material, such as, but not limited to, platinum, platinum alloy or other materials known to be usable in implantable defibrillation electrodes.

The configuration of the therapy systems 10, 11 illustrated in FIGS. 1-3 are merely examples. In other examples, a therapy system may include epicardial leads and/or patch electrodes instead of or in addition to the transvenous leads 18, 20, 22, 28, and 29 illustrated in FIG. 3. Further, IMD 16 need not be implanted within patient 12. In examples in which IMD 16 is not implanted in patient 12, the cardiac module within IMD 16 may deliver defibrillation pulses and other therapies to heart 14 via percutaneous leads that extend through the skin of patient 12 to a variety of positions within or outside of heart 14. In examples in which IMD 16 is not implanted in patient 12, the neuro module within IMD 16 may deliver electrical stimulation to target tissue sites within patient 12 via external electrodes or via percutaneous leads that extend through the skin of patient 12.

In other examples of therapy systems that provide electrical stimulation therapy to heart 14, a therapy system may include any suitable number of leads coupled to the cardiac module within IMD 16, and each of the leads may extend to any location within or proximate to heart 14. For example, other examples of therapy systems may include three transvenous leads located as illustrated in FIGS. 1 and 3, and an additional lead located within or proximate to left atrium 38. As another example, other examples of therapy systems may include a single lead that extends from the cardiac module within IMD 16 into right atrium 30 or right ventricle 32, or two leads that extend into a respective one of the right ventricle 26 and right atrium 28. In another example, one or more of the leads may not be located within the heart, but instead outside and proximate to heart 14.

Similarly, in examples of therapy systems that provide electrical stimulation therapy to spinal cord 44, a therapy system may include any suitable number of leads coupled to the neuro module within IMD 16, and each of the leads may extent to any location within or proximate to spinal cord 44. Furthermore, in some examples, the neuro module may provide stimulation to extravascular tissue. In such examples, each of the leads may extend to any location within or proximate to the extravascular tissue. The neuro stimulator may deliver stimulation to an extravascular tissue site and/or tissue proximate a nerve, which may or may not be extravascular. That is, in some cases, the tissue proximate the nerve may be an extravascular tissue site. In other cases, the lead may be positioned within vasculature and provide stimulation to a tissue site proximate a nerve through the wall of the vein, artery, or other vasculature. In addition, the extravascular tissue site may or may not be proximate a nerve.

Figure 4:
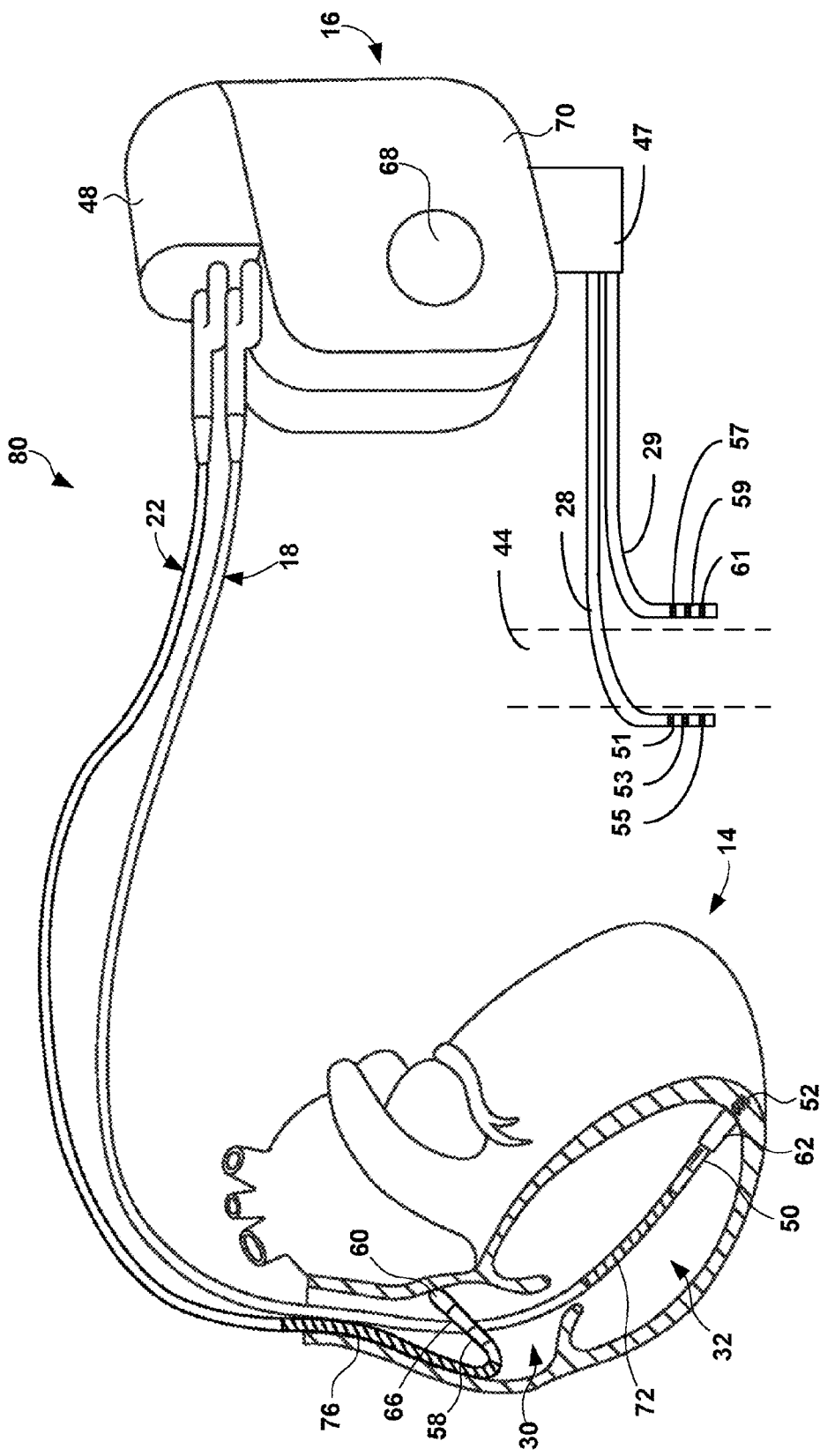
FIG. 4 is a conceptual diagram illustrating another example of the IMD of FIGS. 1 and 2 and the respective leads in greater detail.

FIG. 4 is a conceptual diagram illustrating another example of therapy system 80, which is similar to therapy system 10 of FIGS. 1-2, but includes two cardiac leads 18, 22, rather than three leads. Leads 18, 22 are implanted within right ventricle 32 and right atrium 30, respectively. Therapy system 80 shown in FIG. 4 may be useful for providing defibrillation and pacing pulses to heart 14. Therapy system 80 may further include the neuro module within IMD 16 which is configured to deliver electrical stimulation therapy to one or more nerves or spinal cord 44 (FIG. 2) of patient 14 in order to help prevent or mitigate an arrhythmia of patient 12. Similar to FIG. 3, neuro leads 28 and 29 are coupled to neuro module within IMD 16 via connector block 47.

Figure 5:
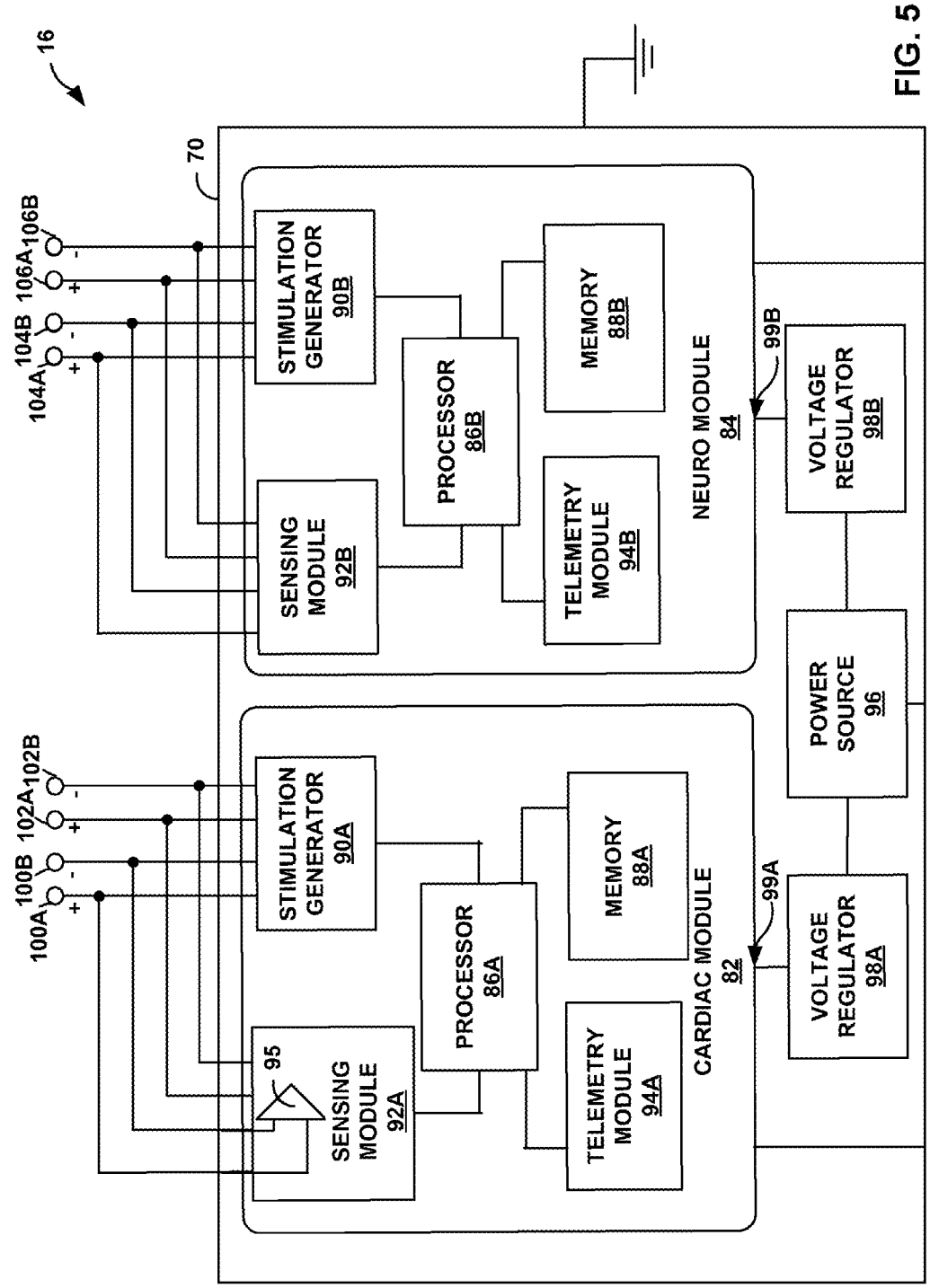
FIG. 5 is a functional block diagram of an example configuration of an IMD.

FIG. 5 is a functional block diagram of a first example configuration of IMD 16. As shown in FIG. 5, IMD 16 includes a cardiac module 82, neuro module 84, voltage regulator 98A, voltage regulator 98B, and power source 96. It should be noted that in some configurations, IMD 16 may not include voltage regulators 98A and 98B. In the example illustrated in FIG. 5, cardiac module 82 and neuro module 84 share a common power source, e.g., power source 96, and ground. Cardiac module 82 and neuro module 84 receive power at power input 99A and 99B, respectively, from power source 96 via voltage regulator 98A and 98B, respectively. In other examples, cardiac module 82 and neuro module 84 may receive power from a common voltage regulator. Voltage regulator 98A and 98B regulate the voltage generated by power source 96. For example, in some aspects, cardiac module 82 and neuro module 84 may need a voltage that is greater than or less than the voltage generated by power source 96. In such examples, voltage regulator 98A and 98B regulate the voltage generated by power source 96 to the appropriate level desired by cardiac module 82 and neuro module 84. In some aspects, voltage regulator 98A and 98B may not be necessary.

As seen in FIG. 5, cardiac module 82 and neuro module 84 share a common power source 96 and ground (e.g., housing 70 in this example). Power source 96 is referenced to the ground provided by housing 70, e.g., the voltage provided by power source 96 is with respect to the ground provided by housing 70. Cardiac module 82 and neuro module 84 are also coupled to housing 70 and thus share a common ground, e.g., the ground provided by housing 70. Accordingly, because cardiac module 82 and neuro module 84 share a common power source and a common ground there is commonality between cardiac module 82 and neuro module 84. In other words, there is an electrical path from cardiac module 82 through power source 96 to neuro module 84 and back to cardiac module 82 via housing 70.

Cardiac module 82 and neuro module 84 include processor 86A and processor 86B, memory 88A and memory 88B, stimulation generator 90A and stimulation generator 90B, sensing module 92A and sensing module 92B, and telemetry module 94A and telemetry module 94B, respectively. Processors 86A, 86B may store values in control registers that control the operation of stimulation generators 90A, 90B, respectively, or transmit such values to a processor associated with the stimulation generators. The processor may include any of a variety of control or processing circuitry. The values may control activation, timing, pulse width, pulse rate, amplitude, electrode combination, electrode polarity and/or other aspects of the stimulation delivered by the stimulation generators. Where appropriate, in some examples, analog-to-digital and/or digital-to-analog conversion circuitry may be provided to convert signals communicated between components of neuro module or cardiac module. Sensing module 92B may be optional in the case of neuro module 84. Memory 88A, 88B may include computer-readable instructions that, when executed by processor 86A, 86B, cause cardiac module 82, neuro module 84 and processor 86A, 86B to perform various functions attributed to cardiac module 82, neuro module 84, and processor 86A, 86B. Memory 88A, 88B may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. In some cases, memory 86A, 86B may share common memory devices have separate memory devices.

Processor 86A, 86B may include any one or more of a microprocessor, a controller, a digital signal processor (DSP), an application specific integrated circuit (ASIC), a field-programmable gate array (FPGA), or equivalent discrete or integrated logic circuitry. In some examples, processor 86A, 86B may include multiple components, such as any combination of one or more microprocessors, one or more controllers, one or more DSPs, one or more ASICs, or one or more FPGAs, as well as other discrete or integrated logic circuitry. The functions attributed to processor 86A, 86B herein may be embodied as software, firmware, hardware or any combination thereof. In some cases, processors 86A, 86B may share common processor components or have separate processor components.

Processor 86A controls stimulation generator 90A to deliver stimulation therapy to heart 14 according to a selected one or more of therapy programs, which may be stored in memory 88A. Specifically, processor 86A may control stimulation generator 90A to deliver electrical pulses with the amplitudes, pulse widths, frequency, or electrode polarities specified by the selected one or more therapy programs. For example, in some implementations, processor 86A may store values in control registers that control the operation of stimulation generator 90A. The values may control activation, timing, pulse width, pulse rate, amplitude, electrode combination, electrode polarity and/or other aspects of the stimulation delivered by stimulation generator 90A. Similarly, processor 86B controls stimulation generator 90B to deliver stimulation therapy to a tissue site, such as target tissue site 40, according to a selected one or more therapy programs, which may be stored in memory 88B. Specifically, processor 86B may control stimulation generator 90B to deliver electrical pulses with the amplitudes, pulse widths, frequency, or electrode polarities specified by the selected one or more therapy programs.

Again, such parameters may be controlled by storing values in control registers that control operation of stimulation generator 90B.

Stimulation generator 90A is electrically coupled to electrodes 100A, 100B, 102A, and 102B. Electrodes 100A, 100B, 102A, and 102B may be electrodes of one or more leads 18, 20, and 22 (FIG. 1). Electrodes 100A and 100B may form an electrode pair where electrode 100A is the anode and 100B is the cathode. Similarly, electrodes 102A and 102B may form an electrode pair where electrode 102A is the anode and 102B is the cathode. Electrodes 100A, 100B, 102A, and 102B may comprise ring electrodes. In other examples, electrodes 100A, 100B, 102A, and 102B may be segmented electrodes arranged in a complex electrode array that includes multiple non-contiguous electrodes at different angular positions about the outer circumference of one or more leads 18, 20, and 22, as well as different levels of electrodes spaced along a longitudinal axis of one or more leads 18, 20, and 22. The configuration, type, and number of electrodes illustrated in FIG. 5 are merely exemplary. In other examples, cardiac module 82 may be coupled to any suitable number of leads with any suitable number and configuration of electrodes. Moreover, one or more of leads 18, 20, and 22 may comprise a shape other than a cylindrical shape. As an example, one or more of leads 18, 20, and 22 may comprise a paddle-shaped portion that carries electrodes 100A, 100B, 102A, and 102B.

Stimulation generator 90A is configured to generate and deliver electrical stimulation therapy to heart 14. For example, stimulation generator 94 may deliver defibrillation shocks to heart 14 via at least two electrodes 100A and 100B, and/or an insulated electrode on the case or housing of IMD 16. Stimulation generator 90A may deliver pacing pulses via electrodes 100A and 100B. In some examples, stimulation generator 90A delivers pacing, cardioversion, or defibrillation stimulation in the form of electrical pulses or shocks.

Stimulation generator 90B is electrically coupled to electrodes 104A, 104B, 106A, and 106B. Electrodes 104A, 104B, 106A, and 106B may be electrodes of one or more leads 28 and 29 (FIG. 2). Electrodes 104A and 104B may form an electrode pair where electrode 104A is the anode and 104B is the cathode. Similarly, electrodes 106A and 106B may form an electrode pair where electrode 106A is the anode and 106B is the cathode. Electrodes 104A, 104B, 106A, and 106B may comprise ring electrodes. In other examples, electrodes 104A, 104B, 106A, and 106B may be segmented electrodes arranged in a complex electrode array that includes multiple non-contiguous electrodes at different angular positions about the outer circumference of lead 28, as well as different levels of electrodes spaced along a longitudinal axis of lead 28. The configuration, type, and number of electrodes illustrated in FIG. 5 are merely exemplary. In other examples, neuro module 84 may be coupled to any suitable number of leads with any suitable number and configuration of electrodes. Moreover, lead 28 may comprise a shape other than a cylindrical shape. As an example, lead 28 may comprise a paddle-shaped portion that carries electrodes 104A, 104B, 106A, and 106B. Stimulation generator 90B may deliver electrical pulses to spinal cord 44 or target stimulation site 40.

Stimulation generator 90A, 90B may be a single- or multi-channel stimulation generator. In particular, stimulation generator 90A, 90B may be capable of delivering, a single stimulation pulse, multiple stimulation pulses, or a continuous signal at a given time via a single electrode combination or multiple stimulation pulses at a given time via multiple electrode combinations.

In some aspects, processor 86A may also control a switching module (not shown) to apply the stimulation signals generated by stimulation generator 90A to selected combinations of electrodes 100A, 100B, 102A, and 102B. In particular, the switching module couples stimulation signals to selected conductors within leads 18, 20, and 22 which, in turn, deliver the stimulation signals across selected electrodes 100A, 100B, 102A, and 102B. The switching module may be a switch array, switch matrix, multiplexer, or any other type of switching device suitable to selectively couple stimulation energy to selected electrodes. Hence, in some aspects stimulation generator 90A is coupled to electrodes 100A, 100B, 102A, and 102B via the switching module. In some aspects, cardiac module 82 does not include the switching module.

Similar to processor 86A, in some aspects, processor 86B may also control a switching module (not shown) to apply the stimulation signals generated by stimulation generator 90B to selected combinations of electrodes 104A, 104B, 106A, and 106B. In particular, the switching module couples stimulation signals to selected conductors within lead 28 which, in turn, deliver the stimulation signals across selected electrodes 104A, 104B, 106A, and 106B. The switching module may be a switch array, switch matrix, multiplexer, or any other type of switching device suitable to selectively couple stimulation energy to selected electrodes. Hence, in some aspects, stimulation generator 90B is coupled to electrodes 104A, 104B, 106A, and 106B via the switching module. In some aspects, neuro module 84 does not include the switching module.

Sensing module 92A monitors signals from at least one of electrodes 100A, 100B, 102A, and 102B in order to monitor electrical activity of heart 14, e.g., via an electrogram (EGM) signal, such as an electrocardiogram (ECG) signal. Sensing module 92A may also include a switch module to select a particular subset of available electrodes to sense the heart activity. In some examples, processor 86A may select the electrodes that function as sense electrodes via the switch module within sensing module 92A, e.g., by providing signals via a data/address bus. In some examples, sensing module 92A includes one or more sensing channels, each of which may comprise an amplifier. In response to the signals from processor 86A, the switch module within sensing module 92A may couple the outputs from the selected electrodes to one of the sensing channels. Sensing module 92A may also measure lead impedance or other tissue measurements that aid a clinician to generate effective therapy programs. For example, the stored operating instructions stored in memory 88A may include instructions for measuring the impedance of electrodes 100A, 100B, 102A, and 102B.

Sensing module 92A includes one or more amplifiers, such as amplifier 95. In some cases, the amplifiers may be configured to sense or detect particular cardiac signals, such as R waves, P waves, or the like. Amplifier 95 may be a differential amplifier that is coupled to electrodes 100A and 100B. Though only one amplifier is shown in FIG. 5, there may be an amplifier coupled to each electrode pair or an amplifier coupled to each individual electrode. For example, there may be another amplifier coupled to electrodes 102A and 102B. Amplifier 95, in the case of a differential amplifier, measures the voltage at electrode 100A with respect to a reference electrode that may be coupled the ground provided by housing 70, and measures the voltage at electrode 100B with respect to the reference electrode that may be coupled to ground provided by housing 70. Amplifier 95 then subtracts the two voltages to generate a sensed signal.

Sensing module 92B monitors signals from at least one of electrodes 104A, 104B, 106A, and 106B in order to monitor electrical activity of target stimulation site 44 (FIG. 1) or spinal cord 44 (FIG. 2). Sensing module 92B may also include a switch module to select a particular subset of available electrodes to sense the activity. In some examples, processor 86B may select the electrodes that function as sense electrodes via the switch module within sensing module 92B, e.g., by providing signals via a data/address bus. In some examples, sensing module 92B includes one or more sensing channels, each of which may comprise an amplifier. In response to the signals from processor 86B, the switch module within sensing module 92B may couple the outputs from the selected electrodes to one of the sensing channels. Similar to sensing module 92A, sensing module 92B may also measure lead impedance or other tissue measurements that aid a clinician to generate effective therapy programs. For example, the stored operating instructions stored in memory 88B may include instructions for measuring the impedance at electrodes 104A, 104B, 106A, and 106B.

Though no amplifier is shown in sensing module 92B for ease of illustration, in some examples, sensing module 92B may comprise one or more sense amplifiers. The one or more amplifiers may be substantially similar to amplifier 95 and perform in a substantially similar manner as amplifier 95. For example, a differential amplifier may be coupled to electrodes 104A and 104B, and another differential amplifier may be coupled to electrodes 106A and 106B used to measure the respective voltages with respect to a reference electrode that may be coupled to the ground provided by housing 70. The amplifiers may then subtract the measured voltages to generate a sense signal.

Though FIG. 5 shows cardiac module 82 and neuro module 84 comprising a stimulation generator and a sensing module, in some examples, cardiac module 82 and/or neuro module 84 may comprise only a stimulation generator or a sensing module. In other words, cardiac module 82 or neuro module 84 may, in some instances, only provide sensing functionality or only provide therapy delivery functionality. For example, cardiac module 82 comprises stimulation generator 90A and sensing module 92A, and neuro module 84 comprises only stimulation generator 90B, and does not comprise sensing module 92B. As another example, cardiac module 82 comprises only sensing module 92A, and neuro module 84 comprises only stimulation generator 90B. Other permutations and combinations are possible, and all are contemplated by this disclosure.

In accordance with this disclosure, since neuro module 84 and cardiac module 82 interconnect via a common power source 96 and are referenced to the same common (e.g., housing 70 in this example), the stimulation generated by neuro module 84 via stimulation generator 90B and electrodes 104A, 104B, 106A, and 106B may interfere with the measurements of sensing module 92A. A stimulation signal generate by stimulation generator 90B may impose a common voltage, e.g., common-mode signal or interference, onto electrode pair 100A, 100B and electrode pair 102A, 102B. The stimulation signal generated by stimulation generator 90B of neuro module 84 is referenced to the ground provided by housing 70. For example, electrodes 104A and 104B may be located near a spine of patient 12. When referenced to the common ground (e.g., housing 70 of IMD 16), the stimulation generated by electrodes 104A and 104B generates an electrical field that extends from the electrodes 104A, 104B to housing 70. Since cardiac module 82 and neuro module 84 share the same ground, e.g., there is commonality between cardiac module 82 and neuro module 84, the common-mode interference may impose a larger common mode signal on the electrodes coupled to sensing module 92A and/or stimulation generator 90A of cardiac module 82 than would be the case if the cardiac module 82 and neuro module 84 coupled to different grounds or references. For example, if cardiac module 82 and neuro module 84 coupled to different grounds or references, the electrical field generated by electrodes 104A, 104B would not extend to the housing 70, but instead only radiate with a smaller spread, e.g., the distance between the electrodes in turn causing a smaller differential-mode signal.

However, because cardiac module 82 and neuro module 84 share a common ground, the common-mode signal is large. This in turn may cause sensing module 92A and/or stimulation generator 90A to function improperly. For example, amplifier 95 may be unable to filter out the larger common-mode signal, e.g., the signal level may be too large for amplifier 95, or amplifier 95 may be unable to adequately attenuate the large signal, thus resulting in improper operation. Sensing module 92A may, for instance, sense an arrhythmia on heart 14 when no such arrhythmia exists. In response to the incorrectly sensed arrhythmia, stimulation generator 90A may stimulate heart 14 when no such stimulation may be necessary. Alternatively, the common-mode signal may cause sensing module 92A to fail to sense an arrhythmia on heart 14 when such arrhythmia exists. In response to not sensing an arrhythmia, simulation generator 90A may not stimulate heart 14 when such stimulation may be needed. Similarly, a stimulation generated by stimulation generator 90A of cardiac module 82 may cause common-mode interference with sensing module 92B and/or stimulation generator 90B of neuro module 84.

Furthermore, defibrillation pulse or stimulation generated by one of the modules, e.g., cardiac module 82 or neuro module 84, may cause shunt current to flow into the other module. As one example, if cardiac module 82 generates a defibrillation pulse as its defibrillation output, the defibrillation pulse generated via electrodes 100A and 100B may feed into the neuro module 84 via electrodes 104A and 104B because the high voltage of the defibrillation pulse from cardiac module 82 is referenced to the same ground as neuro module 84. The shunt current is provided a complete current path due to the shared common ground. The shunt current may unintentionally stimulate tissue, particularly tissue proximate to electrodes 104A and 104B. Additionally, the shunt current may stress neuro module 84, and, in particular, stimulation generator 90B and sensing module 92B of neuro module 84.

In some examples, the rise time of the defibrillation pulse generated by electrodes 100A and 100B may be relatively rapid. The pulse width of the defibrillation pulse may be approximately 10 milliseconds (ms). In some examples, there may be some capacitive coupling between electrodes 104A, 104B and neuro module 84. Due to the rapid rise time of the defibrillation pulse, the capacitive coupling may provide a relatively low impedance path for the shunt current into the neuro module 84 for the duration of the rapid rise time of the defibrillation pulse.

In accordance with this disclosure, various isolation circuits (not shown in FIG. 5) may reduce or eliminate the commonality between neuro module 84 and cardiac module 82 by isolating common circuitry that is shared by neuro module 84 and cardiac module 82. In other words, the isolation circuits described in this disclosure may break the electrical path between cardiac module 82, power source 96, ground (housing 70) and neuro module 84. As such, the crosstalk or at least a portion of the crosstalk does not have an electrical path, or has only a relatively weak path or in other words a relatively high impedance path, via which to reach the other one of the modules.

Various isolation circuits are described in this disclosure, particularly with respect to FIGS. 16-21, which reduce or eliminate the commonality between cardiac module 82 and neuro module 84. In one example, the isolation circuits may couple power source 96 to a power input of either cardiac module 82 or neuro module 84, e.g., power input 99A or 99B. In another example, the isolation circuits may couple a stimulation output of either cardiac module 82 or neuro module 84, e.g., stimulation generator 90A or 90B, and a conductor or electrode of a lead. In a further example, the isolation circuits may couple a sensing input of either cardiac module 82 or neuro module 84, e.g., sensing module 92A or 92B, and a conductor or electrode of a lead. In other examples, there may be a plurality of isolation circuits at various locations throughout IMD 16.

As described above, the isolation circuits may break the electrical path between the cardiac module 82, the common power source 96, neuro module 84 and ground (e.g., housing 70). In one example, the isolation circuit may comprise a plurality of switches and one or more capacitors, sometimes referred to as a flying capacitor circuit. The switches may be opened and closed to charge the one or more capacitors via input lines of the isolation circuit and discharge the stored charge via output lines of the isolation circuit. At no time, however, are the switches closed such that a direct connection exists between power source 96 and the component or module connected to the output of the isolation circuit. As such, the power provided to the component or module connected to the output of the isolation circuit is isolated from power source 96, e.g., references a different ground.

In some instances, the isolation circuit may store charge received from power source 96, and discharge the stored charge to power either cardiac module 82 or neuro module 84. Within the isolation circuit, a first set of switches may be coupled to power source 96 and a second set of switches may be coupled to the power input of cardiac module 82 or neuro module 84. The first set of switches may be toggled to a closed state to charge the capacitors within the isolation circuit while the second set of switches may be toggled to an open state. Capacitors are provided as merely one example. Any device capable of storing energy may be used, e.g., an inductor. After the capacitors are charged, the first set of switches may then be toggled to an open state, i.e., opened, and the second set of switches may be toggled to a closed state, i.e., closed, to discharge the stored charge to power cardiac module 82 or neuro module 84. At no time, however, are the switches closed such that a direct connection exists between power source 96 and the component or module connected to the output of the isolation circuit. As such, the power provided to the component or module connected to the output of the isolation circuit is isolated from power source 96, e.g., references a different ground. Stated another way, the output of the isolation circuit shares no commonality with power source 96.

In other instances, the isolation circuit may be coupled to the stimulation or sensing electrodes of either cardiac module 82 or neuro module 84. In this case, the one or more capacitors may either store the charge that is to be delivered by the respective stimulation generators, e.g., stimulation generator 90A and 90B, or may store the charge sensed by the respective sensing modules, e.g., sensing module 92A and 92B. A first set of the switches may be coupled to the respective stimulation generator or sensing module of cardiac device 82 or neuro device 84, and a second set of switches may be coupled to the respective electrodes of cardiac module 82 and neuro module 84. As described in more detail with respect to FIG. 21, since the first set of switches are open every time the second set of switches are closed, no shunt current may flow through the isolation circuit, thus reducing or eliminating the commonality between cardiac module 82 and neuro module 84. Additionally, since the stimulation generated by the either cardiac module 82 or neuro module 84 is no longer referenced to the same ground as the other module, the stimulation signal may not impose a common voltage, e.g., common-mode interference, across electrode pairs coupled to the other module.

Figure 18A:
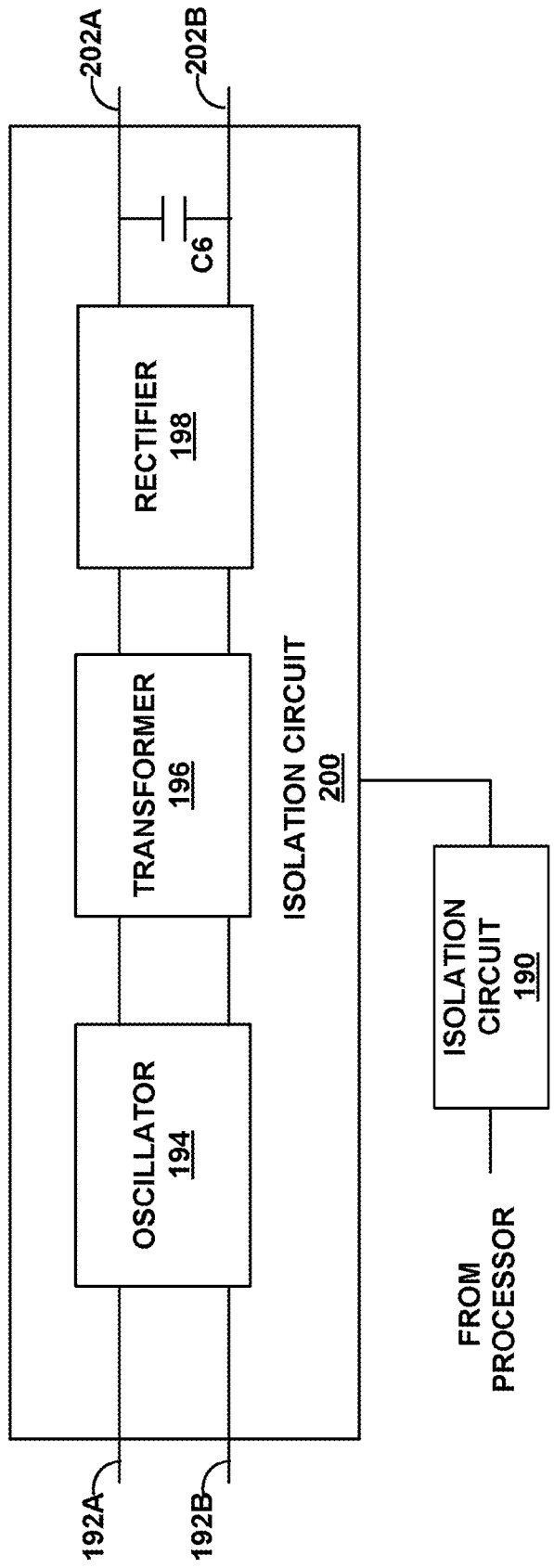
FIG. 18A is a circuit diagram of another example of an isolation circuit.
Figure 18B:
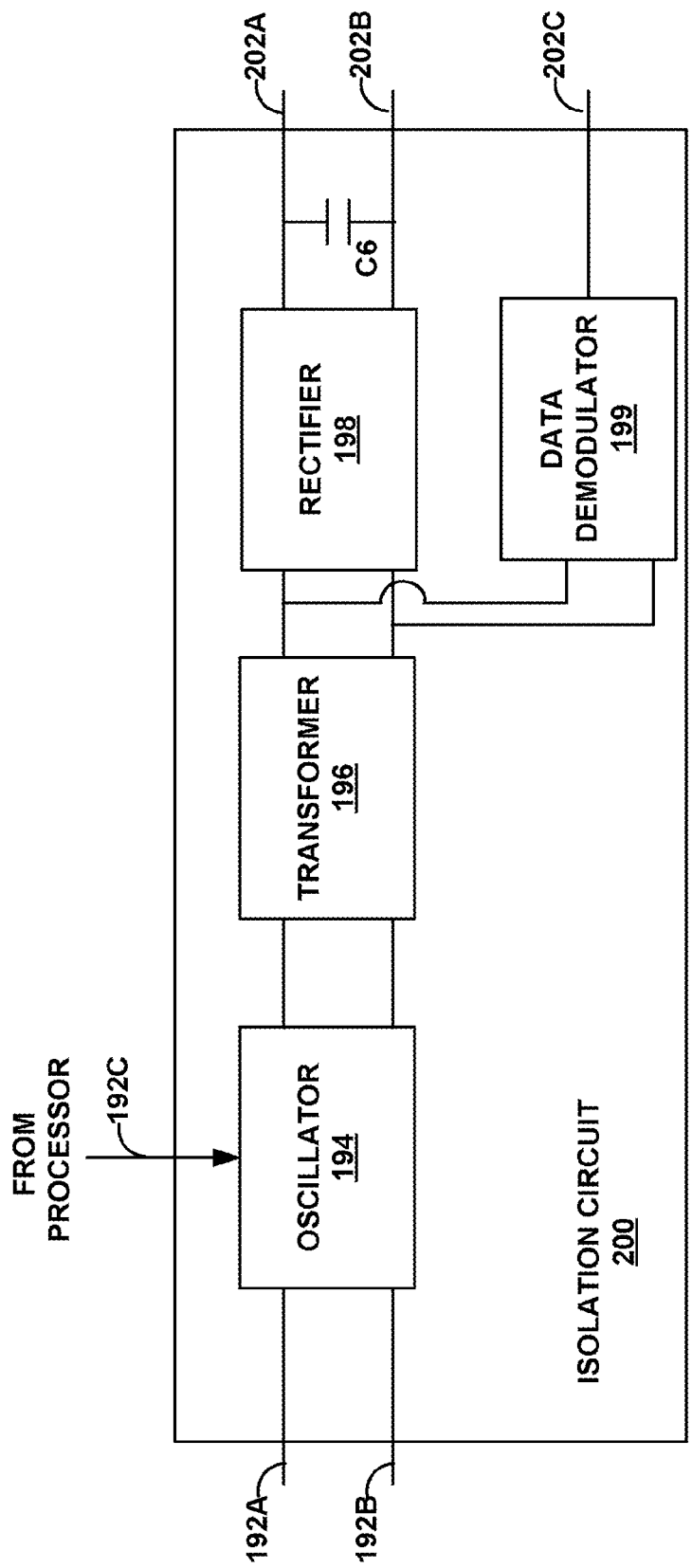
FIG. 18B is a circuit diagram of another example of an isolation circuit.
Figure 19:
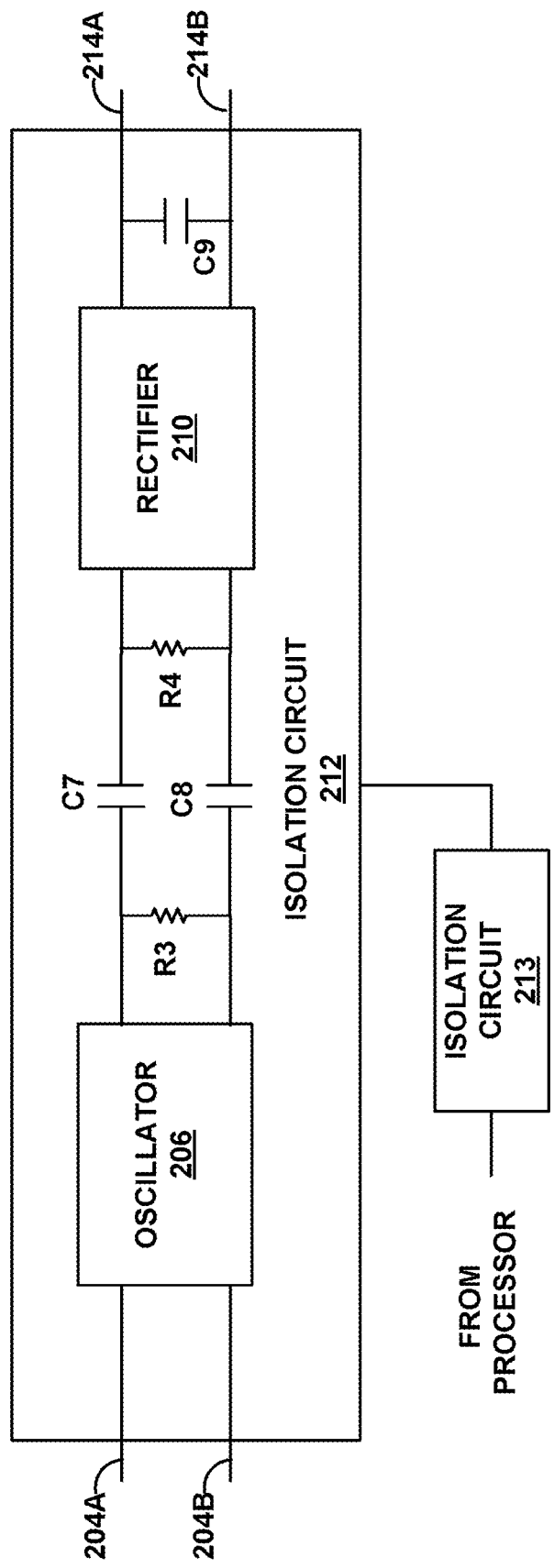
FIG. 19 is a circuit diagram of another example of an isolation circuit.
Figure 20:
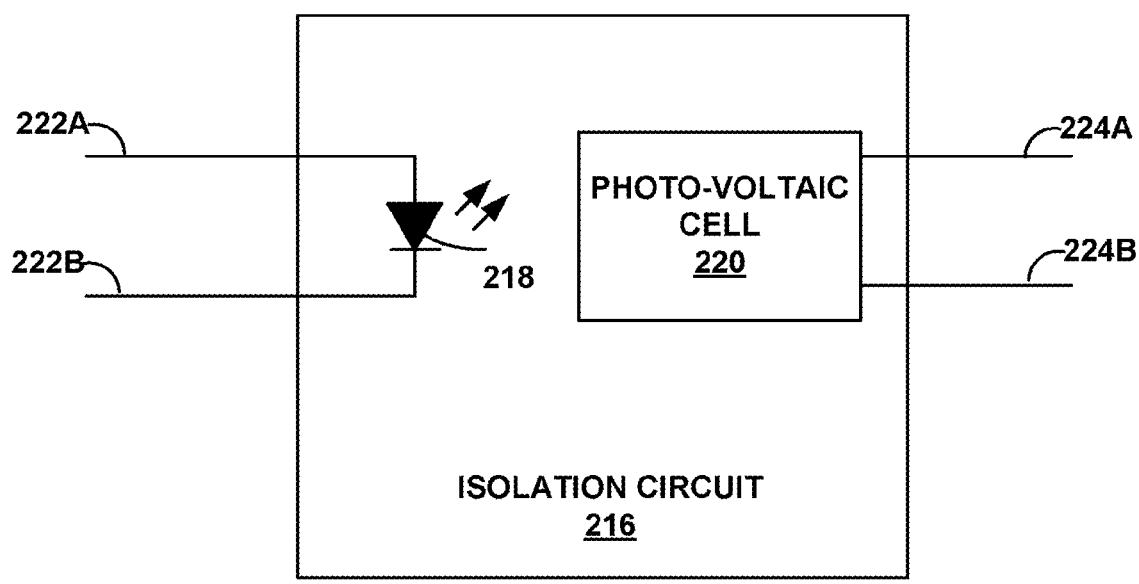
FIG. 20 is a circuit diagram of another example of an isolation circuit.

Isolation circuits may perform similar functions using other configurations, such as using a transformer circuit, a barrier circuit, a photo-voltaic cell, as described in FIGS. 18, 19 and 20, respectively. Regardless of the type of isolation circuit used, the isolation circuit may reduce or eliminate common-mode interference and/or shunt currents. As described above, in some instances, a stimulation signal generated by either cardiac module 82 or neuro module 84 may impose a common voltage on the other module due to the shared commonality. This may cause common-mode interference by affecting the ability of either of the modules to sense a signal. Also, in some instances, a stimulation signal generated by either cardiac module 82 or neuro module 84 may be detected by electrodes of the other module and feed into the other module as shunt current. The shunt current may stimulate tissue that is not intended to be stimulated and/or cause stress to circuitry of the modules.

Providing one or more isolation circuits may reduce or eliminate the shunt current portion attributed to the presence of a common located at the case or housing of IMD 16. Another shunt current that may not be mitigated by isolation is the result of the interception of current between two electrodes located at the spine, which is not related to having a common. By eliminating the shunt current portion attributed to the case or housing of IMD 16, the shunt current at the spine electrodes may be reduced to a more tolerable level. Reducing the shunt current at the spine electrodes may reduce or eliminate tissue stress at the electrode/tissue interface.

The various isolation circuits may reduce or eliminate the common-mode interference generated by cardiac module 82 or neuro module 84 by eliminating the commonality. For example, assume the power input of neuro module 84 is coupled to at least one of the isolation circuits described above and the power input of cardiac module 82 is coupled to power source 96. A stimulation signal generated by cardiac module 82 may not generate common-mode interference because the stimulation signal is no longer referenced to the same ground as the neuro module. In this manner, although within a common housing 70, the crosstalk between the cardiac and neuro modules may be as if they are separate devices.

The various isolation circuits may also reduce or eliminate the shunt current by cardiac module 82 or neuro module 84 by eliminating a complete current path between the modules 82, 84. The complete current path for the shunt current, assuming no isolation circuit, would be from the stimulation generated by one of cardiac module 82 or neuro module 84 into the other module and to a common shared ground, e.g., the ground provided by housing 70. The various isolation circuits may create a barrier for the shunt current. For example, assume the isolation circuit is coupled to stimulation output and sensing input of neuro module 84, e.g., stimulation generator 90B and sensing module 92B, a shunt current generated by cardiac module 82 may not feed into neuro module 84 because the various switches within the isolation circuit will be toggled to an open state. Similarly, if the isolation circuit is coupled to stimulation output and sensing input of cardiac module 82, e.g., stimulation generator 90A and sensing module 92B, a stimulation signal generated by neuro module 84 may not feed into cardiac module 82 because the various switches within the isolation circuit will be toggled to an open state.

Telemetry module 94A and 94B support wireless communication between cardiac module 82 and neuro module 84, respectively, and an external programmer 24 (FIG. 1) or another computing device. Processor 86A and 86B of cardiac module 82 and neuro module 84, respectively, may receive, as updates to programs, values for various stimulation parameters such as amplitude and electrode combination, from programmer 24 via telemetry module 94A and 94B, respectively. The updates to the therapy programs may be stored within memory 88A and 88B, respectively.

The various components of cardiac module 82 and neuro module 84 are coupled to power source 96, which may include a rechargeable or non-rechargeable battery. A non-rechargeable battery may be selected to last for several years, while a rechargeable battery may be inductively charged from an external device, e.g., on a daily or weekly basis. In other examples, power source 96 may be powered by proximal inductive interaction with an external power supply carried by patient 12.

In some examples, to reduce common mode interference and shunt currents, cardiac module 82 and neuro module 84 may each comprise separate power supplies, e.g., rather than a single, shared power source 96. The power supplies may not be coupled to one another. Furthermore, cardiac module 82 and neuro module 84 may each comprise separate ground connections, e.g., separate than housing 70. The ground connections may not be coupled to one another. In such examples, there may not be commonality between cardiac module 82 and neuro module 84. Accordingly, there may be reduction in common-mode interference and shunt current. Cardiac module 82 and neuro module 84 may communicate with one another via telemetry modules 94A and 94B.

However, the requirement for separate power supplies within cardiac module 82 and neuro module 84 may increase costs. Additionally, the functionality of each separate power source may need to be checked separately. For example, a clinician may need to ensure that each power supply is functioning properly instead of ensuring that only one power supply, e.g., power source 96, is functioning properly. Furthermore, cardiac module 82 and neuro module 84 may require different amounts of power. Each power supply may discharge at different rates. The different discharge rates may cause the patient to make repeated trips to the clinician's office to recharge the power supplies. Accordingly, separate power supplies for cardiac module 82 and neuro module 84 may potentially increase costs, increase clinician time, and increase patient visits, but may be desirable in providing isolation.

As shown in FIG. 5, the device that provides cardiac therapy, e.g., cardiac module 82 and the device that provides neurostimulation, e.g., neuro module 84, within IMD 16 share only a common voltage source and ground. However, aspects of this disclosure are not so limited. In some aspects, the devices that provide cardiac therapy and neurostimulation may share other common components or circuitry in addition to or instead of the common ground. For example, in some aspects, the devices that provide cardiac therapy and neurostimulation may share a common processor, memory, and telemetry module, as well as share a common power source and ground.

Figure 6:
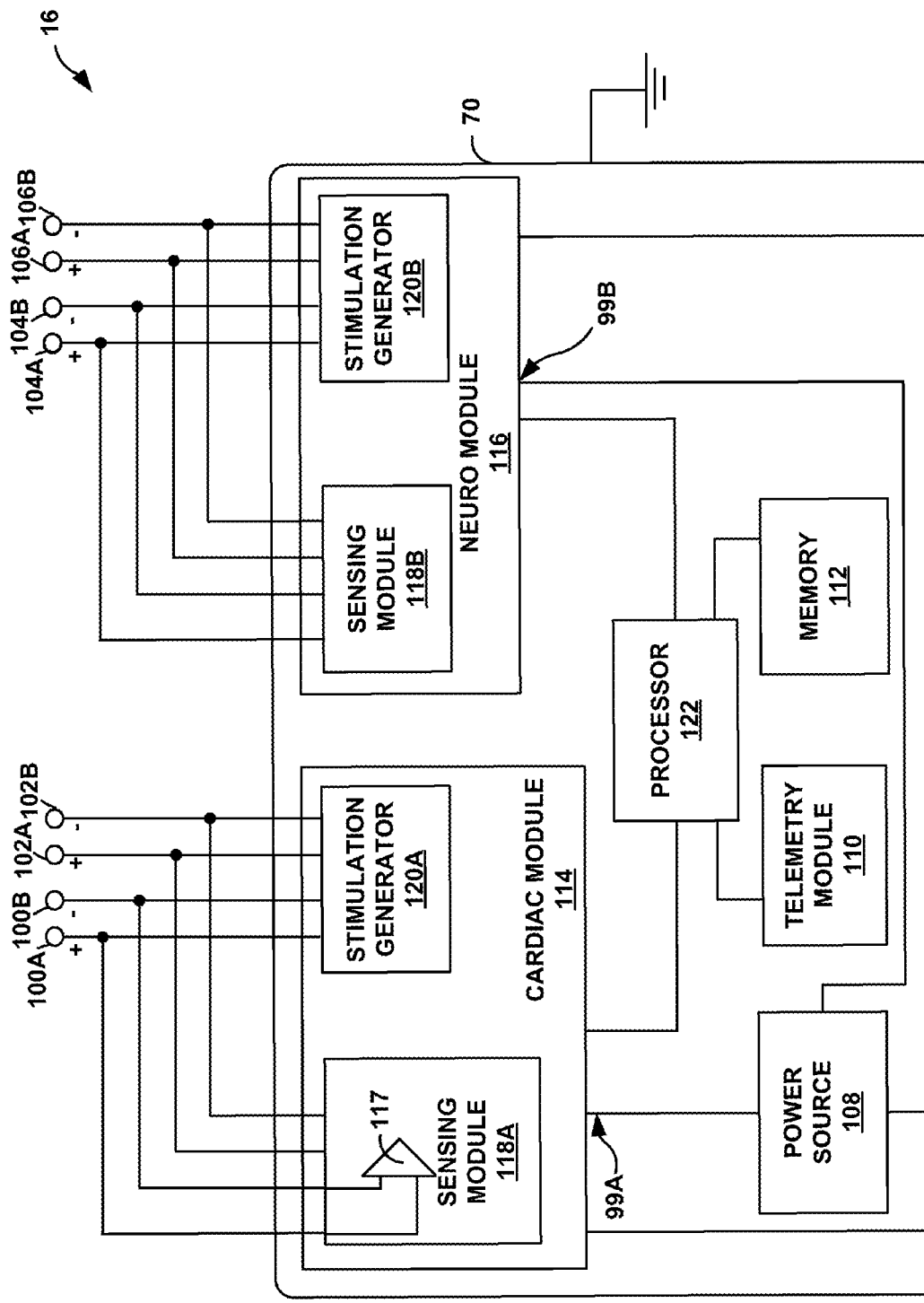
FIG. 6 is a functional block diagram of another example configuration of an IMD

FIG. 6 is a functional block diagram of another example configuration of IMD 16. IMD 16 includes a power source 108, telemetry module 110, memory 112, cardiac module 114, neuro module 116, and processor 122. Cardiac module 114 includes sensing module 118A and stimulation generator 120A. Stimulation generator 120A provides stimulation via electrodes 100A, 100B, 102A, and 102B. Neuro module 116 includes sensing module 118B and stimulation generator 120B. Stimulation generator 120B provides stimulation via electrodes 104A, 104B, 106A, and 106B. In some examples, the ground terminal of power source 108 may be coupled to housing 70, but aspects of this disclosure are not so limited. In examples where housing 70 is a metallic, the ground terminal of power source 108 may be coupled to housing 70. In examples where housing 70 is non-metallic, the ground terminal of power source 108 may not be coupled to housing 70. However, for purposes of clarity, as described herein, the ground terminal of power source 108 is coupled to housing 70. Lines extending from power source 108, cardiac module 114 and neuro module 116 to housing 70 illustrate ground connections.

As shown in FIG. 6, cardiac module 114 and neuro module 116 may share telemetry module 110, memory 112, processor 122, and power source 108. Telemetry module 110 may perform the functions of telemetry module 94A and 94B (FIG. 5). For example, as described with respect to FIG. 5, telemetry module 94A provides communication for cardiac module 82 with programmer 24, and telemetry module 94B provides communication for neuro module 84 with programmer 24. Telemetry module 110 provides communication for cardiac module 114 and neuro module 116 with programmer 24 applying substantially similar techniques as those described for telemetry module 94A and 94B.

Memory 112 may perform the functions of memory 88A and 88B (FIG. 5). Mainly, memory 112 includes computer-readable instructions that, when executed by processor 122, cause cardiac module 114 and neuro module 116 and processor 122 to perform various functions attributed to cardiac module 114, neuro module 116, and processor 122. Memory 112 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. As shown in FIG. 6, instead of requiring two separate memories for providing cardiac and neuro therapy, as shown in FIG. 5, IMD 16 requires only one memory for providing cardiac and neuro therapy.

Processor 122 may perform the same functions as processor 86A and 86B. Similar to processors 86A and 86B, processor 122 may include any one or more of a microprocessor, a controller, a digital signal processor (DSP), an application specific integrated circuit (ASIC), a field-programmable gate array (FPGA), or equivalent discrete or integrated logic circuitry. In some examples, processor 122 may include multiple components, such as any combination of one or more microprocessors, one or more controllers, one or more DSPs, one or more ASICs, or one or more FPGAs, as well as other discrete or integrated logic circuitry. The functions attributed to processor 122 in this disclosure may be embodied as software, firmware, hardware or any combination thereof. In some examples, processor 122 may include integral memory.

Processor 122 controls stimulation generator 120A to deliver stimulation therapy to heart 14 according to a selected one or more of therapy programs, which may be stored in memory 112. Processor 122 also controls stimulation generator 120B to deliver stimulation therapy to therapy stimulation site 40 or spinal cord 44, to name a few examples. Specifically, processor 122 may control stimulation generator 120A and stimulation generator 120B to deliver electrical pulses with the amplitudes, pulse widths, frequency, or electrode polarities specified by the selected one or more therapy programs. Processor 122 may store values in control registers for retrieval by a respective processor that may be associated with modules 114 or 116 or particular components of modules 114, 116, or transmit such values directly to such circuitry. The values may control activation, timing, pulse width, pulse rate, amplitude, electrode combination, electrode polarity and/or other aspects of the stimulation delivered by stimulation generator 120A. Where appropriate, in some examples, processors or other circuitry may include or be coupled to analog-to-digital and/or digital-to-analog conversion circuitry to convert signals communicated between processor 122, neuro module or cardiac module.

Stimulation generator 120A and stimulation generator 120B may be substantially similar to stimulation generator 90A and stimulation generator 90B (FIG. 5), and perform substantially similar functions. Sensing module 118A and sensing module 118B may be substantially similar to sensing module 88A and sensing module 88B (FIG. 5), and perform substantially similar functions. Power source 108 may be substantially similar to power source 96 (FIG. 5), and perform substantially similar functions.

As described above, in accordance with this disclosure, stimulation generated by stimulation generator 120A or 120B may cause common-mode interference on sensing module 118A or 118B. For example, the stimulation generated by stimulation generator 120B may impose a common voltage, e.g., common-mode interference, across electrode pair 100A, 100B and electrode pair 102A, 102B. Because stimulation generator 120B and sensing module 118A share the same common ground, e.g., the ground provided by housing 70, the common-mode interference may feed into sensing module 118A. Due to the common-mode interference, sensing module 118A may incorrectly sense arrhythmia of heart 14 when no arrhythmia exists or fail to sense arrhythmia when arrhythmia exists. For example, as shown in FIG. 6, sensing module 118A includes amplifier 117. Amplifier 117 may be substantially similar to amplifier 95 (FIG. 5), and perform in a substantially similar manner. The common-mode interference may cause amplifier 117 to function improperly, possibly causing sensing module 118A to incorrectly sense a physiological condition. For example, amplifier 117 may be unable to effectively reject the common-mode signal because the common-mode interference is larger due to the coupling to the common ground. Similar to FIG. 5, though only one amplifier is shown in FIG. 6, there may be more than one amplifier in sensing module 118A. Each amplifier may couple to the electrode pair. Furthermore, though no amplifier is shown in sensing module 118B, there may be one or more amplifiers in sensing module 118B that are substantially similar to amplifier 117 and function in a substantially similar manner.

Furthermore, as described above, the stimulation generated by stimulation generator 120A or 120B may create a shunt current that flows through the low impedance electrodes, e.g., electrodes 100A, 100B, 102A, 102B, 104A, 104B, 106A, and 106B. For example, a stimulation generated by 120A may couple into electrodes 104A and 104B as shunt current. The shunt current may stimulate tissue that is unintended to be stimulated, particularly tissue proximate to electrodes 104A and 104B, as well as stress circuitry of the non-delivering device.

Nevertheless, even though cardiac module 114 and neuro module 116 share more circuitry compared to cardiac module 82 and neuro module 84, various isolation circuits located at various locations within IMD 16 may eliminate or reduce the common-mode interference and/or shunt currents. For example, as described with respect to FIG. 5, the various isolation circuits may be coupled to a power input of either cardiac module 114 or neuro module 116, e.g., power input 99A or 99B, a stimulation output of either cardiac module 114 or neuro module 116, e.g., stimulation generator 120A or 120B, or a sensing input of either cardiac module 114 or neuro module 116, e.g., sensing module 118A or 118B. The isolation circuits may comprise at least one of a flying-capacitor circuit, a transformer circuit, a barrier circuit, or a photo-voltaic cell.

When at least one of the isolation circuits is coupled to the power input of either cardiac module 114 or neuro module 116, the isolation circuits may reduce or eliminate the commonality between cardiac module 114 and neuro module 116. By reducing or eliminating the commonality at the power input of cardiac module 114 or neuro module 116, the common-mode interference caused by the module that provides stimulation may not couple into the other module. Also, by reducing or eliminating the commonality at the power input of cardiac module 114 or neuro module 116, a shunt current generated by the module that provides stimulation may not couple into the other module because the isolation circuit creates a barrier for the shunt current. When at least one of the isolation circuits is coupled to a stimulation output or a sensing input of either cardiac module 114 or neuro module 116, a shunt current generated by the module that provides stimulation may not couple into the other module because the isolation circuit creates a barrier for the shunt current.

Figure 7:
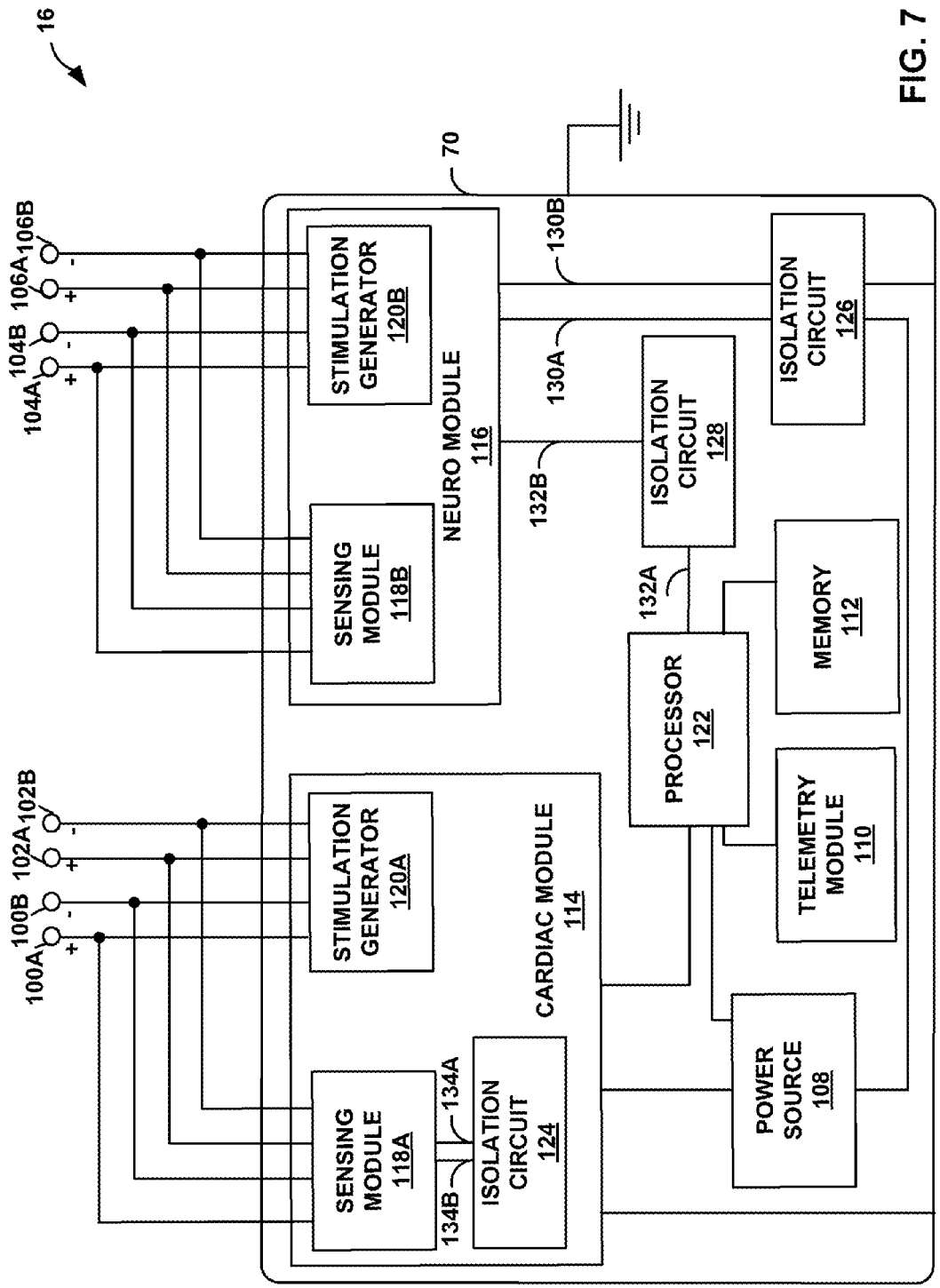
FIG. 7 is a functional block diagram of an example configuration of an IMD comprising isolation circuits to reduce or eliminate commonality.

FIG. 7 is a functional block diagram of an example configuration of IMD 16 comprising isolation circuits to reduce or eliminate commonality. As shown in FIG. 7, IMD 16 includes cardiac module 114, neuro module 116, power source 108, processor 118, telemetry module 110, and memory 112. Cardiac module 114 is coupled to electrodes 100A, 100B, 102A, and 102B. Neuro module 116 is coupled to electrodes 104A, 104B, 106A, and 106B. Cardiac module 114, neuro module 116, power source 108, processor 118, telemetry module 110, memory 112, and electrodes 100A, 100B, 102A, 102B, 104A, 104B, 106A, and 106B function substantially similar to cardiac module 114, neuro module 116, power source 108, processor 118, telemetry module 110, memory 112, and electrodes 100A, 100B, 102A, 102B, 104A, 104B, 106A, and 106B as described with respect to FIG. 6.

IMD 16 may also include isolation circuit 126 and isolation circuit 128. Cardiac module 114 may also include isolation circuit 124. As described above with respect to FIG. 6, the commonality between cardiac module 114 and neuro module 116 may cause common-mode interference and/or shunt currents. Isolation circuit 126 reduces or eliminates the power source commonality between cardiac module 114 and neuro module 116. As shown in FIG. 7, isolation circuit 126 receives voltage from power source 108. The voltage from power source 108 is referenced to ground, which may be the housing 70 of IMD 16. Isolation circuit 126 outputs floating power and floating ground on floating power line 130A and floating ground line 130B, respectively. The output of isolation circuit 126 is referred to as floating power and floating ground because neither power line 130A nor ground line 130B are referenced to power source 108 or ground, e.g., housing 70. Instead, power line 130A and ground line 130B are referenced relative to one another. Stated another way, power source 108 is referenced to the ground provided by housing 70. Power line 130A is referenced to ground line 130B, and neither power line 130A nor ground line 130B is referenced to either power source 108 or the ground provided by housing 70. Examples of isolation circuit 126 include a flying-capacitor circuit, a transformer circuit, a barrier circuit, and a photo-voltaic cell and are shown in FIGS. 16, 18, 19, and 20.

Figure 8:
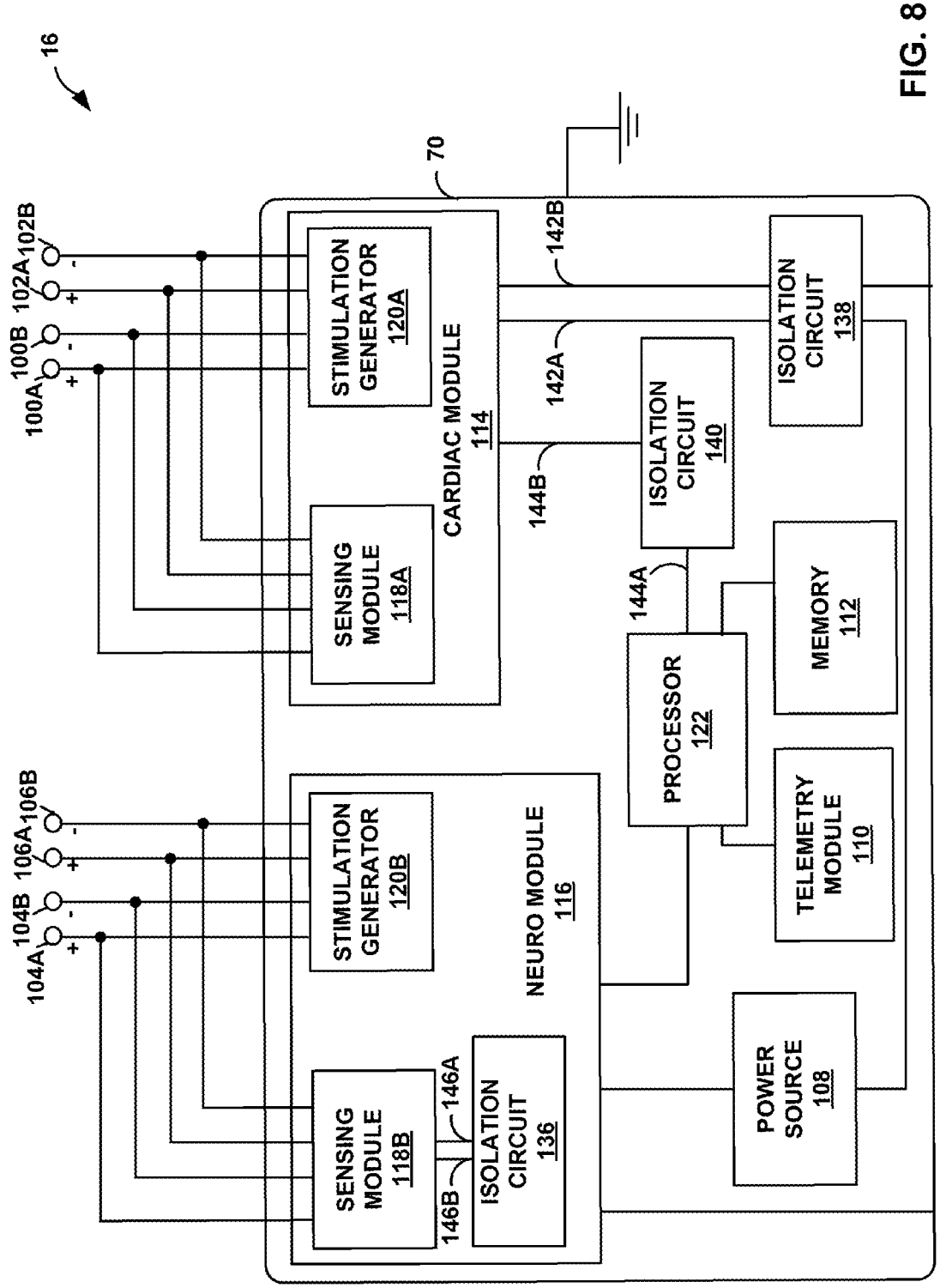
FIG. 8 is a functional block diagram of another example configuration of an IMD comprising isolation circuits to reduce or eliminate commonality.

As described in more detail with respect to FIGS. 16, 18, 19, and 20, isolation circuit 124 and 126 may comprise at least one of a flying-capacitor circuit, a transformer circuit, a barrier circuit, or a photo-voltaic cell. The various isolation circuits receive voltage from power source 108 and generate a voltage that is not referenced to power source 108 or ground provided by housing 70. For example, in a flying-capacitor circuit, as described in more detail with respect to FIG. 16, power and ground lines are coupled to power source 108 and housing 70, respectively. The power and ground lines may be coupled to one or more capacitors via a first set of a plurality of switches, e.g., switches S7 and S8 of FIG. 16. A second set of the plurality of switches may be coupled to the floating power and ground lines 130A, 130B which may be coupled to neuro module 116, e.g., switches S11 and S12 of FIG. 16. As shown in FIG. 7, floating power and ground lines 130A, 130B are coupled to a power input and ground terminal, respectively, of neuro module 116, but may be coupled to a power input and ground terminal, respectively, of cardiac module 114, as shown in FIG. 8. The first set of switches may be closed to charge the one or more capacitors, and the second set of switches may be opened so no voltage is provided to the floating power and ground lines while the capacitor is charging. Once the one or more capacitors are charged to a proper level, the first set of switches may be opened, and the second set of switches may be closed to provide voltage to the power input of either cardiac module 114 or neuro module 116. The voltage is provided across floating power and ground lines 130A, 130B only when the first set of switches is open. Accordingly, there is no direct connection, e.g., commonality, between power source 108 or ground provided by housing 70 and the floating power and ground lines 130A, 130B because the switches are never closed to directly couple power source 108 through floating power and ground lines 130A, 130B.

In examples where the isolation circuit is a transformer circuit, as described in more detail with respect to FIG. 18A and FIG. 18B, an oscillator receives power from power source 108. The oscillator generates a voltage pulse. As one non-limiting example, a voltage pulse with a 5 volt amplitude may be generated by the oscillator. The 5 volt amplitude is with respect to the ground provided by housing 70. The oscillator provides the voltage pulse to a primary of a transformer, which in turn generates a voltage pulse on the secondary of the transformer. The output of the transformer generates a voltage that is not referenced to power source 108 because there is no direct connection between the secondary of the transformer and power source 108 or ground provided by housing 70. The output of the transformer is provided to a rectifier that is coupled to one or more capacitors. The output of the one or more capacitors is coupled to the floating power and ground lines 130A, 130B. Because there is no direct connection, e.g., commonality, between the primary side and secondary side of the transformer, the voltage across the one or more capacitors is not referenced to power source 108 or ground provided by housing 70. Accordingly, the voltage at the floating power and ground lines 130A, 130B are referenced to one another, and not to power source 108 or ground provided by housing 70. Various types of transformers may be used such as electrical transformers and piezoelectric transformers.

In examples where the isolation circuit is a barrier circuit, as described in more detail with respect to FIG. 19, an oscillator receives power from power source 108. The oscillator generates a voltage pulse. The oscillator provides the voltage pulse to a plurality of coupling capacitors. The coupling capacitors create a barrier for any direct current (DC) voltage, thereby removing any connection with power source 108 or ground provided by housing 70. The output of the coupling capacitors is provided to a rectifier that is coupled to one or more capacitors. The output of the one or more capacitors is coupled to the floating power and ground lines 130A, 130B. Due to the coupling capacitors there is no commonality between floating power and ground lines 130A, 130B and the power source 108 or the ground provided by housing 70.

In examples where the isolation circuit is a photo-voltaic cell, as described in more detail with respect to FIG. 20, a light emitting diode (LED), as one non-limiting example, or the like is coupled to power source 108 and the ground provided by housing 70. Power source 108 causes the LED to illuminate. The illumination of the LED causes photo-voltaic cell to create a voltage and current. The output of the photo-voltaic cell is coupled to floating power and ground lines 130A, 130B. Due to the conversion of the voltage provided by power source 108 to a light, and the conversion of the light to a voltage there is no commonality between floating power and ground lines 130A, 130B and the power source 108 or the ground provided by housing 70.

Accordingly, as shown in FIG. 7, power line 130A and ground line 130B provide a voltage source for the various circuitry within neuro module 116. For example, power line 130A and ground line 130B provide voltage to sensing module 118B and stimulation generator 120B. Accordingly, the stimulation signals generated by stimulation generator 120B are referenced to power line 130A and ground line 130B, and are not referenced to power source 108 and the ground provided by housing 70.

Isolation circuit 124 provides further reduction in commonality between cardiac module 114 and neuro module 116. In some examples, isolation circuit 124 may not be necessary. As shown in FIG. 7, isolation circuit 124 receives voltage from power source 108 which is referenced to the ground provided by housing 70. Similar to isolation circuit 126, isolation circuit 124 outputs floating power and floating ground via power line 134A and 134B, respectively. Floating power line 134 couples to a power input of sensing module 118A and floating ground line 134B couples to a ground terminal of sensing module 118A. Similar to power line 130A and ground line 130B, power line 134A and ground line 134B are not referenced to power source 108 and the ground provided by housing 70. As described above with respect to isolation circuit 126, power line 134A and ground line 134B are referenced to one another instead of power source 108 and ground provided by housing 70. Power line 134A and ground line 134B are completely independent of power line 130A and ground line 130B. Isolation circuit 124 may be substantially similar to isolation circuit 126. Examples of isolation circuit 124 include a flying-capacitor circuit, a transformer circuit, a barrier circuit, and a photo-voltaic cell and are shown in FIGS. 16, 18, 19, and 20.

Power line 134A and ground line 134B provide voltage to the various circuitry within sensing module 118A. Accordingly, sensing module 118A is referenced independent to stimulation generator 120B. In accordance with the disclosure, isolation circuit 126 and 124 may provide reduction or elimination in the common-mode interference and shunt currents. For example, a stimulation generated by stimulation generator 120B may not impose a common-mode signal upon electrode pairs 100A, 100B and 102A, 102B because sensing module 118A does not share any commonality with the ground provided by housing 70. Stated another way, isolation circuit 124 creates a barrier for the common-mode interference so that the common-mode interference cannot be imposed upon sensing module 118A. Thus, although sensing module 118A may sense a differential signal from the neurostimulation, the interference may be much smaller than the common-mode signal that would be sensed if cardiac module 114 and neuro module 116 shared a common ground.

Though not shown in FIG. 7, sensing module 118A and sensing module 118B may include amplifiers that are substantially similar to amplifier 95 (FIG. 5) and amplifier 117 (FIG. 6). Particularly, the amplifiers may be coupled to electrode pairs 100A, 100B and 102A, 102B with respect to sensing module 118A, and coupled to electrode pairs 104A, 104B and 106A, 106B with respect to sensing module 118B.

Isolation circuit 126 may also reduce or eliminate the shunt current. For example a stimulation generated by stimulation generator 120B may not feed into electrodes 100A, 100B, 102A, and 102B because there is not a complete current path for the shunt current. Isolation circuit 126 creates a high impedance barrier for the shunt current to flow from electrodes 104A, 104B, 106A, and 106B, through electrodes 100A, 100B, 102A, and 102B, and back into stimulation generator 120B because isolation circuit 126 reduces or eliminates any commonality with cardiac module 114 and neuro module 116 and the ground provided by housing 70. Similarly, a stimulation generated by stimulation generator 120A may not feed into electrodes 104A, 104B, 106A, and 106B because there is no complete current path for the shunt current. Isolation circuit 126 creates a high impedance path for the shunt current to flow from electrodes 100A, 100B, 102A, and 102B, through electrodes 104A, 104B, 106A, and 106B, and back into stimulation generator 120A.

As shown in FIG. 7, processor 122 transmits data signals to and receives data signals from cardiac module 114 and neuro module 116. Processor 122 controls stimulation generator 120A to deliver stimulation therapy to heart 14 according to a selected one or more therapy program(s), which may be stored in memory 112. Processor 122 may control stimulation generator 120A to deliver electrical pulses with the amplitudes, pulse widths, frequency, or electrode polarities specified by the selected one or more therapy programs. For example, in some implementations, processor 122 may store values in control registers that control the operation of stimulation generator 120A. The values may control activation, timing, pulse width, pulse rate, amplitude, electrode combination, electrode polarity and/or other aspects of the stimulation delivered by stimulation generator 120A. In some cases, cardiac module 114 or stimulation generator 120A of cardiac module 114 may include a processor or related circuitry for receiving values from control registers or directly from processor 122. A processor of cardiac module 114 or stimulation generator 120A may control stimulation generator 120A to deliver stimulation therapy according to a selected one or more therapy programs. For example, a processor may control stimulation generator 120A to generate an electrical stimulation waveform that conforms to the therapy program parameters.

Processor 122 controls stimulation generator 120B to deliver stimulation therapy to a tissue site, such as target tissue site 40, according to a selected one or more therapy programs, which may be stored in memory 112. Specifically, processor 122 may provide signals to a processor (not shown in FIG. 7) of neuro module 116 or of stimulation generator 120B. Processor 122 may provide stored values in control registers for retrieval by a processor or circuitry of neuro module 116 or stimulation generator 120B of neuro module 116, or provide values directly to a processor of neuro module 116 or stimulation generator 120B. The values may control activation, timing, pulse width, pulse rate, amplitude, electrode combination, electrode polarity and/or other aspects of the stimulation delivered by stimulation generator 120B. A processor of neuro module 116 or stimulation generator 120B may control stimulation generator 120B to deliver stimulation therapy according to selected one or more therapy programs. For example, the processor may control circuitry within stimulation generator 120B that generates a waveform that conforms to the therapy program parameters.

In some examples, processor 122 may also facilitate communication between cardiac module 114 and neuro module 116. Without isolation for processor 122, commonality may exist between cardiac module 114 and neuro module 116 through processor 122. This commonality may also result in common-mode interference or crosstalk between cardiac module 114 and neuro module 116. As shown in FIG. 7, isolation circuit 128 provides isolation between the common circuitry, e.g. processor 122, shared by cardiac module 114 and neuro module 116. As shown in FIG. 7, processor 122 transmits or receives data on control line 132A and 132B. Control line 132A is separated from control line 132B via isolation circuit 128. In some aspects, control line 132A may be referenced to power source 108 and the ground provided by housing 70. Stated another way, the signal on control line 132A may be with respect to power source 108 and the ground provided by housing 70. For example, if there is a signal on control line 132A, the voltage of that signal will be with respect to the ground provided by housing 70. In some aspects, control line 132B is referenced to power line 130A and ground line 130B which are floating power and floating ground, respectively. Stated another way, in some aspects, the signal on control line 132B may be with respect to floating power and ground lines 130A, 130B. As described above, power line 130A and ground line 130B are independent of power source 108A and the ground provided by housing 70. Accordingly, control line 132A and 132B are referenced independent of one another.

It should be noted that a common connection between modules occurs when the electrodes of both modules are connected to the patient, since the patient is a relatively low impedance path. The commonality that may be eliminated or reduced using the techniques of this disclosure is the commonality that would otherwise occur within the device or circuit. Thus, some of the techniques of the disclosure seek to avoid a complete circuit, through the device itself that may result in a shunt current path completion or result in a common mode condition.

Furthermore, though control lines 132A and 132B are shown as single lines for purposes of illustration, in some examples, control lines 132A and 132B may comprise a plurality of control lines in parallel with one another. For example, processor 122 may communicate multiple signals simultaneously to neuro module 116, or neuro module 116 may communicate multiple signals simultaneously to processor 122. In such examples, processor 122 and/or neuro module 116 may communicate via the parallel control lines.

Figure 15B:
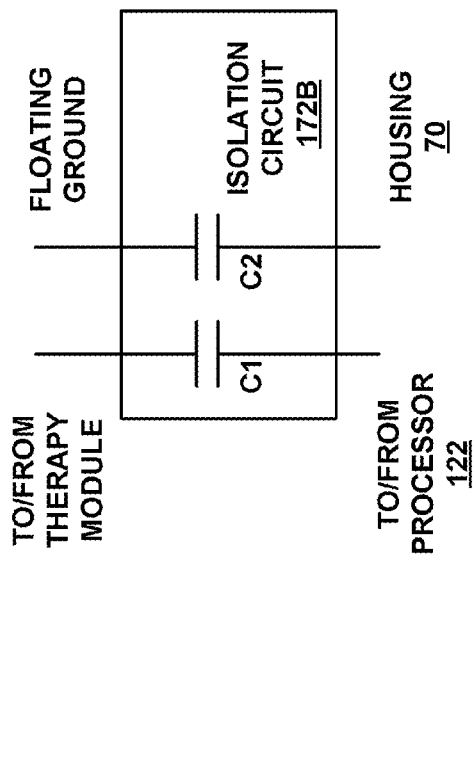
FIG. 15B is a circuit diagram of another example of an isolation circuit.
Figure 15A:
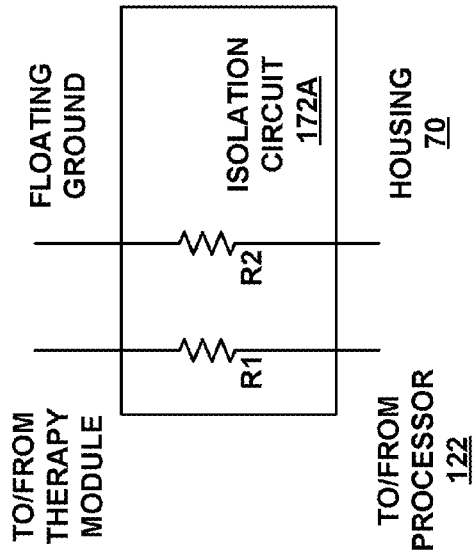
FIG. 15A is a circuit diagram of an example of an isolation circuit.
Figure 15C:
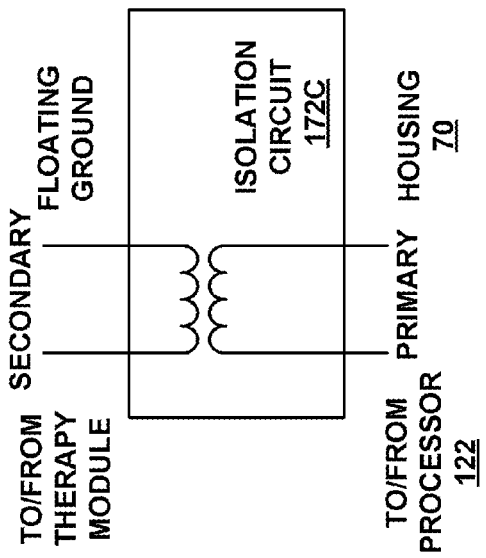
FIG. 15C is a circuit diagram of another example of an isolation circuit.
Figure 15D:
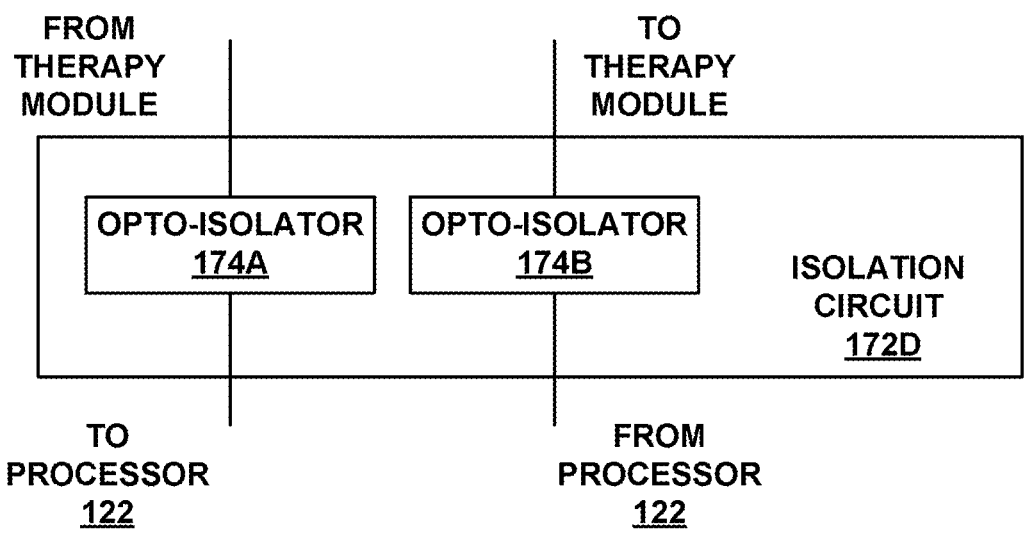
FIG. 15D is a circuit diagram of another example of an isolation circuit.

Isolation circuit 128 may be resistors, capacitors, a transformer, opto-isolators, photo-voltaic cells, a solid state memory device, or a microprocessor. An example of isolation circuit 128 comprising resistors is shown in FIG. 15A. An example of isolation circuit 128 comprising capacitors is shown in FIG. 15B. An example of isolation circuit 128 comprising a transformer is shown in FIG. 15C. An example of isolation circuit 128 comprising opto-isolators is shown in FIG. 15D. An example of isolation circuit 128 comprising photo-voltaic cells is shown FIG. 15E. An example of isolation circuit 128 comprising the solid state memory device is shown in FIG. 15F. An example of isolation circuit 128 comprising the microprocessor is shown in FIG. 15G.

In some examples, communication between neuro module 116 and processor 122 may require a communication line and a reference. For example, in some implementations, the output of processor 122 may be serial digital data. To properly transmit a binary 1 or a binary 0, the digital values require a reference. Similarly, the measurement of a voltage, e.g., binary 1 or binary 0, therefore requires two lines, the communication line that transmits the digital data and a reference line. The communication line may comprise control lines 132A and 132B. However, neuro module 116 and processor 122 do not share a common reference. In other words, neuro module 116 and processor 122 are not referenced the same, e.g., neuro module 116 is referenced to floating ground 130B and processor 122 is referenced to the ground provided by housing 70. Accordingly, to properly communicate between neuro module 116 and processor 122, in some examples, a common reference may be needed to overcome the lack of reference between neuro module 116 and processor 122. Isolation circuit 128 may provide the common reference to allow communication between processor 122 and neuro module 116.

The common reference between processor 122 and neuro module 116 may potentially create commonality between processor 122 and neuro module 116. As described in more detail below, isolation circuit 128 may provide weak commonality between processor 122 and neuro module 116. Weak commonality allows there to be proper communication between processor 122 and neuro module 116. However, weak commonality does not provide a low-impedance path for the shunt current. Nor does the weak commonality allow appreciable common-mode interference.

Only in some examples does communication between processor 122 and neuro module 116 require a communication line and a reference. In examples where isolation circuit 128 comprises resistors, capacitors, or a transformer, communication between neuro module 116 and processor 122 may require a communication line and a reference. In examples where isolation circuit 128 comprises opto-isolators, photovoltaic cells, and a solid state memory device, communication between neuro module 116 and processor 112 may not require a communication line and a reference. In examples that include an opto-isolator, a photo-voltaic cell, and a solid state memory device, a communication line may not be required.

Isolation circuit 128 may comprise two high impedance resistors as shown in more detail with respect to FIG. 15A. Two high impedance resistors may provide isolation between control line 132A and 132B. A first resistor may be coupled between control line 132A and control line 132B. A second resistor may be coupled between the ground provided by housing 70 and floating ground 130B. Control line 132A coupled to control line 132B via the first resistor may comprise the communication line and housing 70 coupled to floating ground 130B may comprise the reference. Impedance values for the resistors may be within a range of 10 kiloohms to 10 megaohms, as one non-limiting example. In examples where isolation circuit 128 comprises high impedance resistors, there may still be commonality between neuro module 116 and cardiac module 114 via processor 122. However, the commonality is greatly reduced. That is, because of the high impedance resistors, coupling between neuro module 116 and cardiac module 114 is weak.

In one example (not shown), a coupling resistor may be utilized to connect the ground provided by housing and floating ground together. The control lines do not utilize a resistor, but instead a data line connects to the high impedance input of an amplifier, or in some examples, two data lines are utilized in which a differential signal is applied as a signal that is detected by measuring the differential signal of the receiving module.

In examples where control line 132A and 132B comprise a plurality of control lines in parallel, isolation circuit 128 may comprise more than two resistors. Isolation circuit 128 may comprise a plurality of resistors where each resistor couples each one of the plurality of control lines. In such examples, only one reference may be necessary. The reference may be provided by coupling housing 70 to floating ground 130B via the high impedance resistor.

Isolation circuit 128 may comprise two capacitors as shown in more detail with respect to FIG. 15B. A first capacitor may be coupled between control line 132A and control line 132B. A second capacitor may be coupled between the ground provided by housing 70 and floating ground 130B. Control line 132A coupled to control line 132B via the first capacitor may comprise the communication line and housing 70 coupled to floating ground 130B may comprise the reference. Capacitance values for the capacitors may be within a range of approximately 10 pico-farads to 100 pico-farads, as one non-limiting example. The capacitors may limit commonality between cardiac module 114 and neuro module 116 via processor 122 because the capacitors provide DC voltage isolation.

In examples where control line 132A and 132B comprise a plurality of control lines in parallel, isolation circuit 128 may comprise more than two capacitors. Isolation circuit 128 may comprise a plurality of capacitors where each capacitor couples each one of the plurality of control lines. In such examples, only one reference may be necessary. The reference may be provided by coupling housing 70 to floating ground 130B via the capacitor.

Isolation circuit 128 may comprise a transformer as shown in more detail with respect to FIG. 15C. The primary of the transformer may be coupled to control line 132A and the ground provided by housing 70. The secondary of the transformer may be coupled to control line 132B and the floating ground line 130B. Because the energy transfers inductively between the primary and secondary windings of the transformer, there is no direct electrical connection between processor 122 and neuro module 116. The signal on the primary of the transformer may be referenced to the ground provided by housing 70. The signal on the secondary of the transformer may be referenced to floating ground line 130B. However there is no direct electrical connection between the ground provided by housing 70 and floating ground line 130B. Similarly, there is no direct connection between control line 132A and control line 132B. Accordingly, the transformer may reduce or eliminate the commonality between cardiac module 114 and neuro module 116 via processor 122.

Isolation circuit 128 may comprise opto-isolators as shown in more detail with respect to FIG. 15D. In such examples, a communication line and a reference may not be necessary. A communication line may suffice. The opto-isolators may provide isolation between control line 132A and 132B. One opto-isolator may transmit data from processor 122 to neuro module 116. Another opto-isolator may transmit data from neuro module 116 to processor 122. Opto-isolators may use a short optical transmission path to transfer signals between processor 122 and neuro module 116 while keeping them electrically isolated. The opto-isolators convert the electrical signal into an optical signal and back to an electrical signal. The electrical connection between control line 132A and 132B may be eliminated because the data is provided optically. Examples of opto-isolators include opto-relays, opto-transistors, opto-field effect transistors (FETs), opto-diodes, and opto-silicon controlled rectifier (SCR). In examples where isolation circuit 128 is an opto-isolator, there may be no commonality between neuro module 116 and cardiac module 114 via processor 122 because the opto-isolator reduces or eliminates the commonality. In examples where isolation circuit 128 is an opto-isolator, the opto-isolator may receive power via isolation circuit 126.

Similar to above, in examples where control line 132A and 132B comprise a plurality of control lines in parallel, isolation circuit 128 may comprise a plurality of opto-isolators. Isolation circuit 128 may comprise a plurality of opto-isolators where each opto-isolator couples each one of the plurality of control lines. Notably, opto-isolators that transmit data from neuro module 116 to processor 122 may be needed for each of the plurality of control lines. Similarly, opto-isolators that transmit data from processor 122 to neuro module 116 may be needed for each of the plurality of control lines.

Figure 15E:
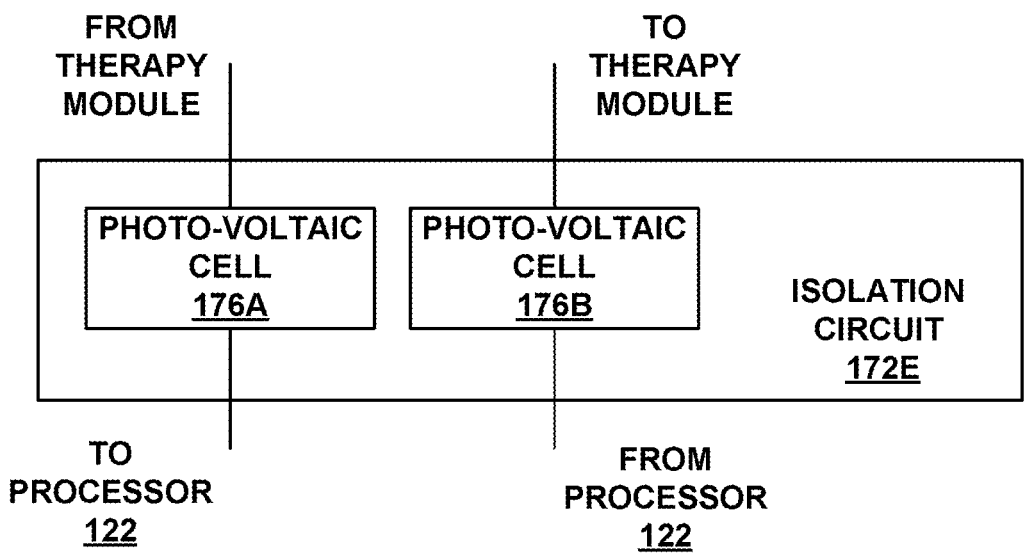
FIG. 15E is a circuit diagram of another example of an isolation circuit.
Figure 15F:
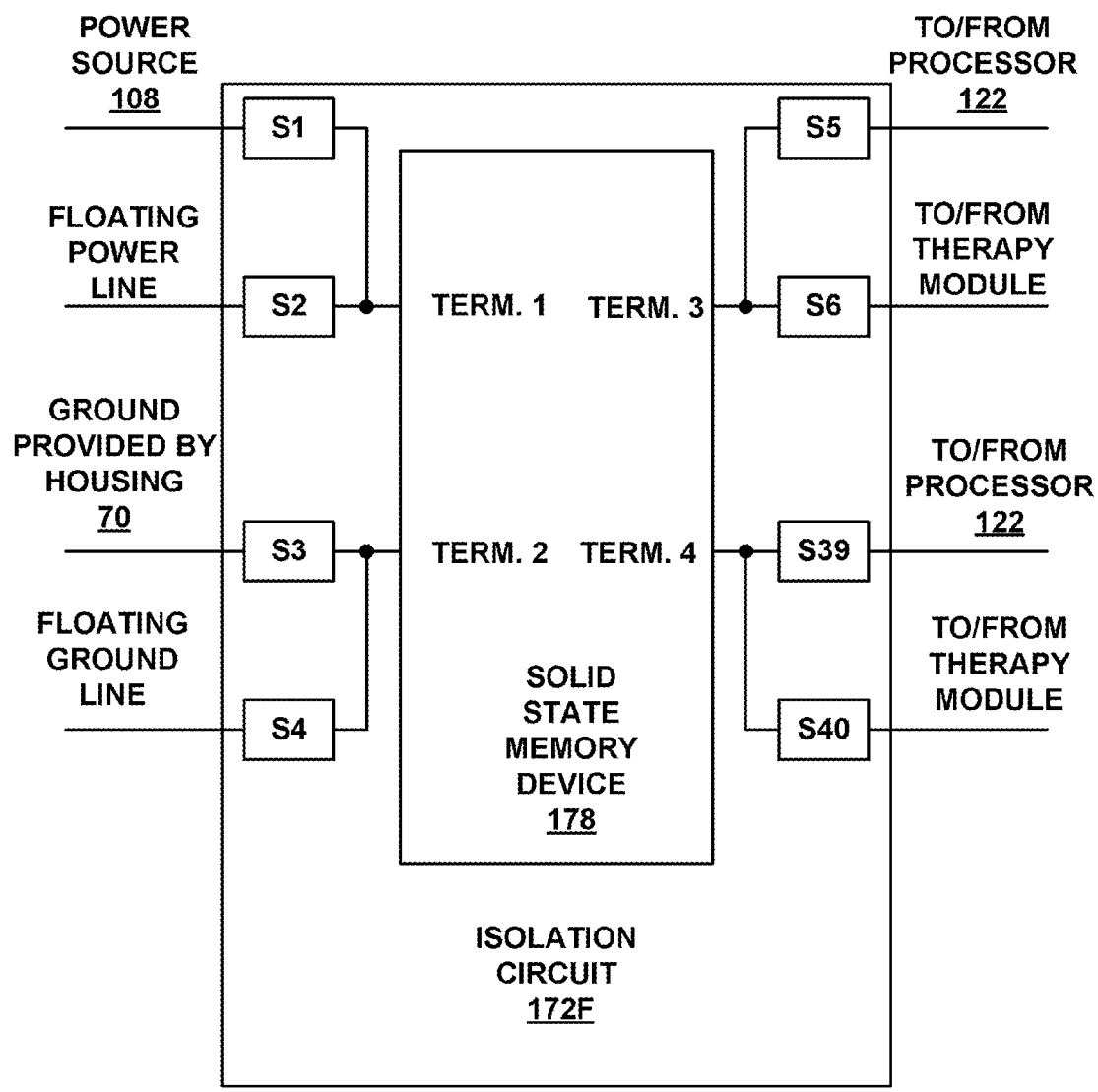
FIG. 15F is a circuit diagram of another example of an isolation circuit.
Figure 15G:
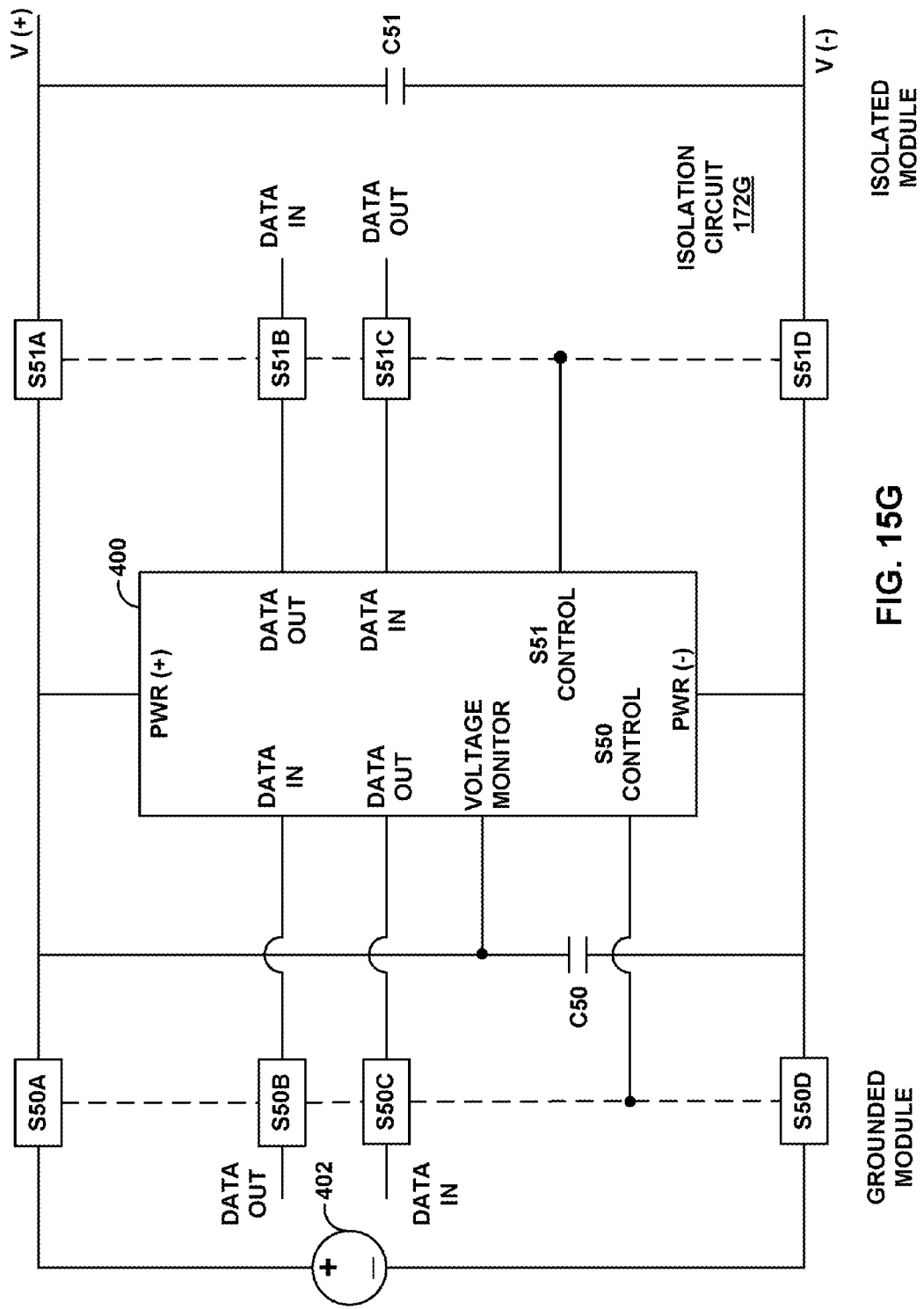
FIG. 15G is a circuit diagram of another example of an isolation circuit.

Isolation circuit 128 may comprise photo-voltaic cells as shown in more detail with respect to FIG. 15E. In such examples, a communication line and a reference may not be necessary. A communication line may suffice. The photo-voltaic cells may provide isolation between control line 132A and 132B. The photo-voltaic cells may function substantially similar to opto-isolators. Particularly, the photo-voltaic cells may receive a signal, convert the signal into an optical signal, and convert the optical signal back to an electrical signal. Similar to opto-isolators, two photo-voltaic cells may be needed. One photo-voltaic cell may transmit data from processor 122 to neuro module 116. Another photo-voltaic cell may transmit data from neuro module 116 to processor 122.

Similar to above, in examples where control line 132A and 132B comprise a plurality of control lines in parallel, isolation circuit 128 may comprise a plurality of photo-voltaic cells. Isolation circuit 128 may comprise a plurality of photo-voltaic cells where each photo-voltaic cell couples each one of the plurality of control lines. Notably, photo-voltaic cells that transmit data from neuro module 116 to processor 122 may be needed for each of the plurality of control lines. Similarly, photo-voltaic cells that transmit data from processor 122 to neuro module 116 may be needed for each of the plurality of control lines.

In some examples, isolation circuit 128 may comprise a solid state memory device as shown in more detail with respect to FIG. 15F. The solid state memory may be volatile or non-volatile memory, and may be used to exchange data between processor 122 and a neuro or cardiac module (generally "therapy module") on an isolated basis. In some cases, the solid state memory may comprise a resistor random-access memory (RRAM) using, for example, memristors. In other cases, the solid state memory may comprise random-access memory (RAM), static random access memory (SRAM), electrically erasable programmable read-only memory (EEPROM), read-only memory (ROM), FLASH memory, and the like. Example configurations that include volatile memory, e.g., RAM or SRAM, may require a capacitor or battery, for example, to power the memory during transitions between modules, as well as a set of switches for the power to the memory as provided by each module. The solid state memory device may be a memory device similar or identical to memory chips commonly referred to as two-wire serial memory chips. In one example, the solid state memory device may comprise four terminals; a power terminal, a ground terminal, a serial read/write terminal, and a serial control terminal.

The power and ground terminals provide power to the memory device. The serial read/write terminal allows a neuro module 116 or processor 122 to serially write data into the solid state memory device, or serially read data out of the solid state memory device. The serial control terminal may allow selection between read and write modes. Similarly, for cardiac module 114, the serial read/write terminal allows cardiac module 114 or processor 122 to serially write data into the solid state memory device, or serially read data out of the solid state memory device.

The power terminal may be selectively coupled to power source 108 via a first switch and may be selectively coupled to the floating power line 130A via a second switch. The ground terminal may be selectively coupled to the ground provided by housing 70 via a third switch and may be selectively coupled to the floating ground line 130B via a fourth switch. In this manner, the solid state memory device can be alternately powered by grounded power and floating power. The read/write terminal may be selectively coupled to processor 122 via the fifth switch and may be selectively coupled to a therapy module (such as cardiac module 114 or neuro module 116) via a sixth switch. In some examples, the read/write terminal may be selectively coupled to a processor of a therapy module via the sixth switch. The control terminal may be selectively coupled to processor 122 via a seventh switch and to neuro module 116, a processor within neuro module 116, or a processor within stimulation generator 120B via an eighth switch.

In some examples, an enable signal may be generated based on a clock signal from a clock source (not shown) to provide a signal to control the serial loading of data in and out of the solid state memory device. Processor 122, or a processor within stimulation generator 120B, may serially write data to or serially receive data from the solid state memory device at different times based on respective enable signals. In this manner, processor 122 utilizes the memory device for read and write operations at selected times, while the therapy (neuro or cardiac) module utilizes the memory device for read and write operations at different, selected times. Hence, processor 122 uses the memory device at different times, providing an isolation interface for exchange of information between processor 122 and a therapy module. When processor 122 uses the memory device, the memory device may be powered by the grounded power source 108. When the therapy (cardiac or neuro) module uses the memory device, the memory device may be powered by a floating power supply that does not share a common reference with power source 108.

When processor 122 has its own power during "fly time," such as via a capacitor or a battery, processor 122 may control the switches S5, S6, S39, and S40 in FIG. 15F. Processor 122 may monitor the voltage across switches S1, S2, S3, and S4 in order to determine when those switches toggle to an open state. When switches S1, S2, S3, and S4 are opened, processor 122 closes switches S5, S6, S39, and S40, thereby transferring data and power. When the transfer of data and power is completed, processor 122 opens switches S5, S6, S39, and S40 in anticipation for the next connection to switches S1, S2, S3, and S4. It should be noted that data can be moved in either direction.

In operation, in response to a first enable signal, processor 122 may apply a signal to the serial control terminal to permit reading of data by serially loading data from the solid state memory device via the serial read/write terminal, and apply a signal to the serial control terminal to permit writing of data by serially loading data from the solid state memory device via the serial read/write terminal. In response to a second enable signal, a processor or other circuitry associated with a therapy module may perform similar operations at a different time. In this manner, at alternating times, processor 122 may read data that was previously written to the solid state memory device by the therapy module, and the therapy module may read data that was previously written to the solid state memory device by processor 122. In each case, along with reading data, the processor 122 or therapy module may also write data to the solid state memory device, permitting the processor 122 and therapy (cardiac or neuro) module to exchange data such as control parameters, operational data, sensor data or the like across an isolation interface that does not share a common reference.

In some cases, the serial data stream loading to and from the read/write port by processor 122 or the therapy module may include read commands, write commands, addressing information, end of data markers, or other information to control the operation of the solid state memory device in storing data from processor 122 or the therapy module. In some examples, the solid state memory device may recognize particular data bits or bit patterns of the serial data stream as commands and store and retrieve a serial data stream in response to the commands. The enable signal may cause processor 122 to start and stop transmitting the serial data stream, and be used to control switches coupled to the various terminals of the solid state memory device.

Processor 122 and the therapy module may use different clocks that are not referenced to one another to produce the enable signals at different times, or use isolated versions of the same clock signal to produce the enable signals at different times. If different clocks are used in an asynchronous manner relative to one another, the length of the enable signal, i.e., the time between rising and falling edges of the enable signal that triggers read and write operations, may be selected to be substantially smaller than the period of the enable signal so that that small errors in the different clocks are less likely to cause the enable signals to overlap with each other over an extended period of time. In some examples, the asynchronous clocks may be periodically resynchronized to minimize the risk of overlap of the enable signals generated for the processor 122 and the therapy module. In this manner, it is possible to prevent the processor 122 from reading and writing at the same time the therapy (neuro or cardiac) module is reading and writing with respect to the solid state memory device.

As described above, separate clocks may be used to generate the enable signals for the processor 22 and therapy module. Although a common clock signal could be used to generate the enable signals, the common clock signal could cause commonality between the therapy module and processor 122. Accordingly, in examples where IMD 16 includes only one clock source, an additional isolation circuit may be provided to isolate the clock signal for use by the therapy module. The isolation circuit may be any one of isolation circuits described above (FIGS. 15A-15E). In the case of separate clock sources, the two clock sources may be independent of one another, and not share any common components. The two clock sources may be considered to be asynchronous. A first clock source may be referenced to power source 108 and the ground provided by housing 70, and the second clock source may be referenced to floating power and ground lines 130A, 130B. The clock sources may be used to generate respective enable signals and, in some cases, clock the serial data read from and written to the solid state memory device.

In one example, a clock on the left side of memory device 178 may be used to drive the rate of switch activation for switches on the left side of memory device 178. By virtue of the rate/timing at which processor 122 connects to the right side of memory device 178, which corresponds directly with the timing that the switches on the right side of memory device 178 toggles, the clock may be conveyed from the left side to the right side of memory device 178. A processor may monitor for when the right side switches toggle to a closed stated in order to determine the corresponding clock rate/synchrony of the left side.

Referring again to FIG. 15F, using separate enable signals, processor 122 and a processor associated with the therapy (cardiac or neuro) module may be controlled to open and close their respective switches so that the first, third, fifth, and seventh switches (S1, S3, S5, and S39, respectively) are not in a closed state when the second, fourth, sixth, and eighth switches (S2, S4, S6, and S40, respectively) are in a closed state. Again, in some examples, processor 122 may include integral memory and/or may be coupled to memory 112. For processor 122 to read or write data, assertion of a first enable signal causes closing of the first, third, fifth, and seventh switches. Deassertion of the enable signal causes the first, third, fifth and seventh switches to open. For processor 122 to read data, processor 122 may provide a signal to the control terminal indicating that the solid state memory device should be in read mode. Processor 122 may then read serial data from the solid state memory device, thereby reading data that was previously written by the therapy module, as applicable. To write data, processor 122 may provide a signal to the control terminal indicating that the solid state memory device should be in write mode. Processor 122 may then write the serial data to the solid state memory device. Hence, read and write modes may be carried out sequentially in response to the same enable signal. For example, processor 122 may first read data and then write data. In some cases, the write operation may overwrite the read data. In other examples, the processor 122 may perform read and write operations at different times in response to different enable signals.

In some examples, rather than processor 122 controlling the second, fourth, sixth, and eighth switches, the processor(s) within neuro module 116 may control the second, fourth, sixth, and eighth switches. In these examples, when neuro module 116 transmits or receives data, neuro module 116 may control the times when neuro module 116 reads data from or writes data to the solid state memory device. Alternatively, in some examples, the solid state memory device itself may control the second, fourth, sixth, and eighth switches via a processor internal to the solid state memory device. In these examples, solid state memory device may determine when it should receive data from neuro module 116 or transmit data to neuro module 116.

Similarly, for a processor or other circuitry associated with a therapy module, assertion of a second enable signal causes closing of the second, fourth, sixth, and eighth switches. Deassertion of the second enable signal causes the second, fourth, sixth and eighth switches to open. In this example, a processor carried by or coupled to a therapy module may provide a signal to the control terminal indicating that the solid state memory device should be in read mode, in which case serial data may be read from the serial read/write terminal. To write data, a signal may be applied to the control terminal to indicate the write mode, in which case a processor or other circuitry associated with a therapy module may write data to the solid state memory device via the serial read/write port. Again, read and write modes may be carried out sequentially in response to the same enable signal, or performed at separate times in response to different enable signals.

In the examples described above, the first, third, fifth, and seventh switches are in an open state when the second, fourth, sixth, and eighth switches are in a closed state, and vice versa. Accordingly, processor 122 and therapy module are never coupled directly to one another, or to the solid state memory device at the same time. In other words, due to the first, third, fifth, and seventh switches being open when the second, fourth, sixth, and eighth switches are closed, and vice versa, there is no commonality between processor 122 and the therapy module. In these examples, the solid state memory device may be considered as flying between processor 122 and the therapy (neuro or cardiac) module because the solid state memory device receives power from the same power source that provides power to processor 122, e.g., power source 108, in one state, and receives power from the same power source that provides power to the therapy module, e.g., floating power and ground lines 130A, 130B for neuro module 116, in another state.

In examples where solid state memory device is volatile memory, e.g., RAM, the data stored within the solid state memory device may be erased when power is removed. In such examples, to avoid loss of power to the solid state memory device a component or device that stores power or provides power may be coupled between the power and ground terminals of the solid state memory device to provide power to the solid state memory device when power from power source 108 is removed. Examples of components or devices that store power or provide power are a capacitor, e.g., a ceramic or electrolytic capacitor having a value of about 0.1 microfarads to about 100 microfarads, a super capacitor, an ultra capacitor, a rechargeable battery or cell, or a primary battery or cell coupled to a diode. For example, when the first and third switches are closed power source 108 and the ground provided by housing 70 provide power to the solid state memory device and charges the capacitor or the rechargeable battery. When the first and third switches are opened but before the second and fourth switches are closed, the capacitor, rechargeable battery, or the primary battery provide power to the solid state memory device. When the second and fourth switches are closed, floating power and ground lines 130A, 130B provide power to the solid state memory device and the charges the capacitor or the rechargeable battery. When the second and fourth switches are opened but before the first and third switches are closed, the capacitor, rechargeable battery, or primary battery provide power to the solid state memory device.

In examples where the solid state memory device is non-volatile memory, it may be beneficial to include a component or device that stores power or provides power when power from power source 108 is removed to the solid state memory device. In some examples of non-volatile memory, after power is removed and then subsequently reapplied to the non-volatile memory, the non-volatile memory may require a startup time before the memory is fully functional. Components that provide power to the solid state memory device when power from power source 108 is removed may allow the solid state memory device to be functional without the need for startup.

Use of a solid state memory device may reduce or eliminate the commonality between cardiac module 114 and neuro module 116 or cardiac module 114 while permitting the transfer of information such as control parameters, operational data, sensor data or the like. As described above, when processor 122 is coupled to the memory device, the cardiac or neuro module is not. Accordingly, there is no commonality between neuro or cardiac module and processor 122, yet the memory device stores data that can be accessed and written by the respective processor and modules.

As shown in FIG. 7, cardiac module 114 and neuro module 116 share processor 122, telemetry module 110, and memory 112. However, aspects of this disclosure are not so limited. In some examples, cardiac module 114 and neuro module 116 may each include a processor and share telemetry module 110 and memory 112. In such examples, isolation circuits may be necessary on telemetry module 110 and memory 112 to reduce or eliminate the commonality between cardiac module 114 and neuro module 116. As another example, cardiac module 114 and neuro module 116 may each include memory and share telemetry module 110 and processor 122. In such examples, isolation circuits may only be necessary on processor 122 since telemetry module 110 can communicate with cardiac module 114 and neuro module 116 via processor 122. Different combinations may be possible and are contemplated by this disclosure.

FIG. 8 is a functional block diagram of another example configuration of IMD 16 comprising isolation circuits to reduce or eliminate commonality. In the example shown in FIG. 8, isolation circuit 138 provides power to cardiac module 114 via power line 142A and ground line 142B. Isolation circuit 138 is substantially similar to isolation circuit 126 (FIG. 7) but provides power to cardiac module 114 instead of neuro module 116 via power line 142A and ground line 142B. Power line 142A and ground line 142B are substantially similar to power line 130A and ground line 130B, respectively but are coupled to cardiac module 114. Isolation circuit 136 is substantially similar to isolation circuit 124 but provides power to sensing module 118B via power line 146A and ground line 146B. Power line 146A and ground line 146B are substantially similar to power line 134A and ground line 134B but are coupled to sensing module 118B. Isolation circuit 140 is substantially similar to isolation circuit 128. Control line 144B is substantially similar to control line 132B. Control line 144A is substantially similar to control line 132A but is coupled to cardiac module 114.

In accordance with this disclosure, isolation circuits 136, 138, and 140 may reduce or eliminate common-mode interference and shunt currents substantially similar to the manner in which isolation circuit 126 and 128 reduce or eliminate common-mode interference as described above with respect to FIG. 7. The common-mode interference may be reduced or eliminated because a stimulation signal may not impose a voltage common-mode voltage or impose a smaller common-mode voltage on the module not providing stimulation. The stimulation signal may not impose a voltage because the commonality between the modules may be reduced or eliminated by isolation circuit 136 and 138. Similarly, no shunt current may feed into electrodes 100A, 100B, 102A, and 102B or electrodes 104A, 104B, 106A, and 106B due to a stimulation generated by either stimulation generator 120A or 120B because isolation circuit 138 provides a high impedance barrier within the complete current path of the shunt current.

Figure 9:
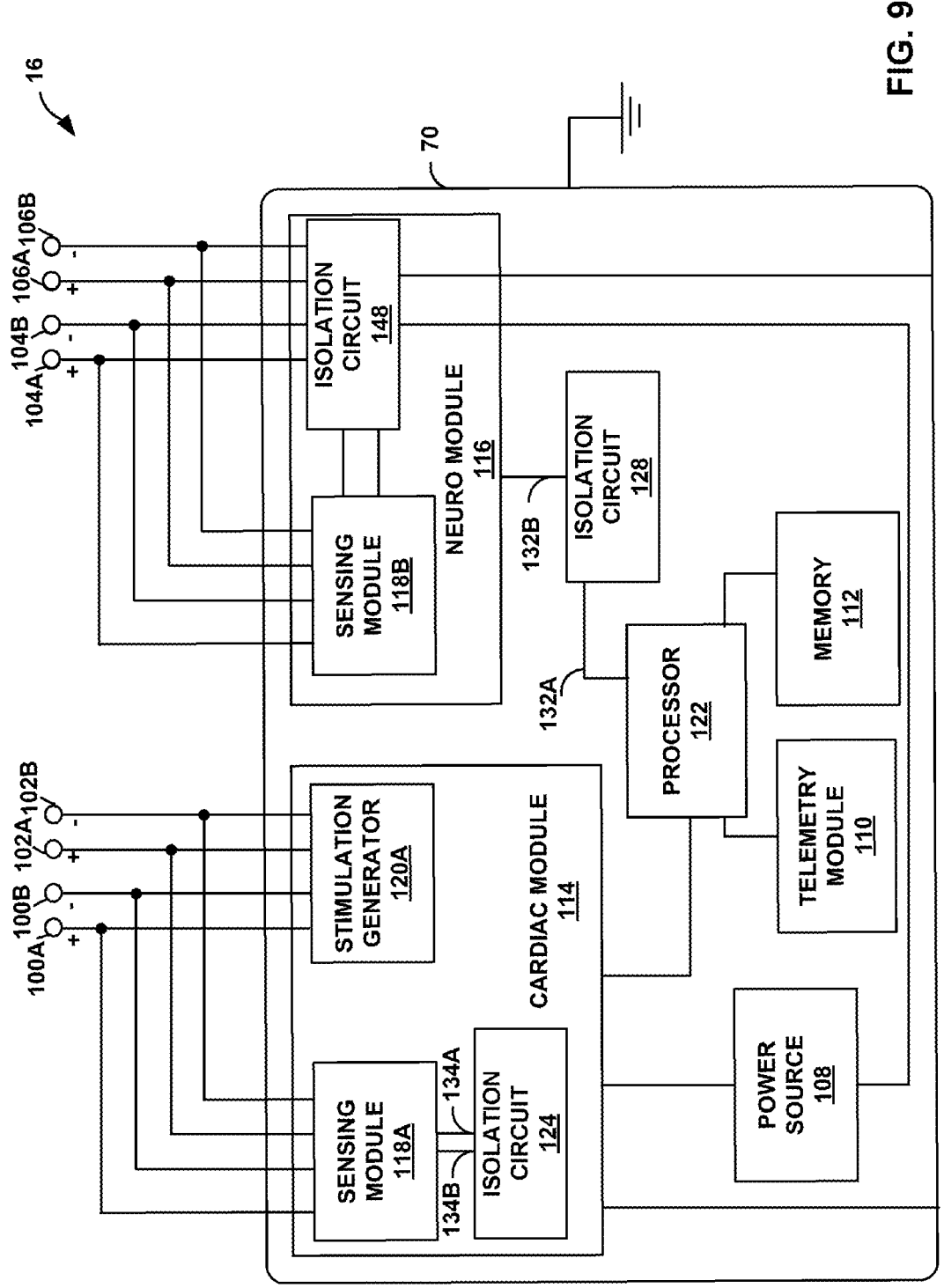
FIG. 9 is a functional block diagram of another example configuration of IMD comprising isolation circuits to reduce or eliminate commonality.

FIG. 9 is a functional block diagram of another example configuration of IMD 16 comprising isolation circuits to reduce or eliminate commonality. The example of IMD 16 shown in FIG. 9 is substantially similar to the example of IMD shown in FIG. 7. However, in the example of IMD 16 shown in FIG. 9 there is no stimulation generator 120B and isolation circuit 126 (FIG. 7). Instead, isolation circuit 148 may provide all the functionality of stimulation generator 120B and isolation circuit 126. For purposes of clarity, the functionality of cardiac module 114, sensing module 118A and 118B, stimulation generator 120A, power source 108, telemetry module 110, memory 112, isolation circuit 124 and 128, control line 134A and 134B, and control line 132A and 132B will be not be described with respect to FIG. 9 since their functionality has already been described with respect to FIG. 7.

Isolation circuit 148 reduces or eliminates the power source commonality between cardiac module 114 and neuro module 116. Isolation circuit 148 may comprise a plurality of sub-isolation circuits, as described in more detail with respect to FIGS. 21, 22, and 23. Examples of sub-isolation circuits include a flying-capacitor circuit and a transformer circuit, as described in more detail with respect to FIGS. 21, 22 and 23. For example, isolation circuit 148 may comprise three sub-isolation circuits. The first sub-isolation circuit may provide power to sensing module 118B. The remaining two sub-isolation circuits provide stimulation signals to electrodes 104A, 104B, 106A, and 106B. For example, one output of the second sub-isolation circuit may be coupled to electrode 104A, and the other output of the second sub-isolation circuit may be coupled to electrode 104B. One output of the third sub-isolation circuit may be coupled to electrode 106A, and the other output of the third sub-isolation circuit may be coupled to electrode 106B.

Figure 21:
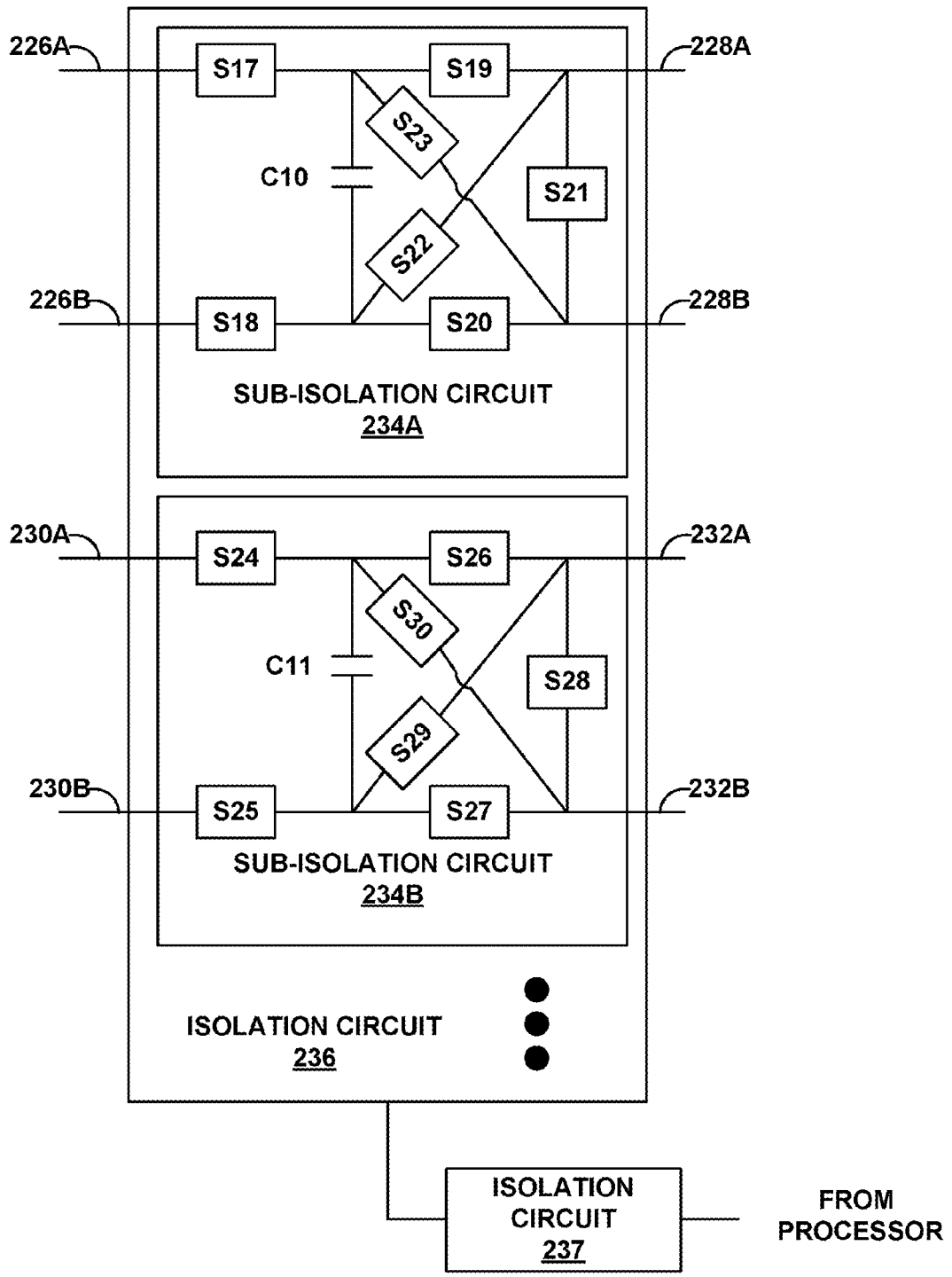
FIG. 21 is a circuit diagram of another example of an isolation circuit.

As described in more detail with respect to FIG. 21, in one example isolation circuit 148 may comprise a plurality of sub-isolation circuits, where each sub-isolation circuit is a flying-capacitor circuit as shown in FIG. 21. Each sub-isolation circuit may comprise a plurality of switches and one or more capacitors. To provide stimulation, processor 122 may close a first set of the switches and open a second set of switches to charge up a first capacitor and second capacitor to the stimulation voltage. After the first capacitor and second capacitor is charged to its preset level, processor 122 may open the first set of switches, and processor 122 may close the second set of switches to discharge the first capacitor to electrodes 104A, 104B, and discharge the second capacitor to 106A, and 106B. The preset level of the capacitor may be the amplitude of the stimulation signal set by the therapy program. Since either the first set of switches or the second set of switches will be open when the other is closed, there is no commonality and no current path between neuro module 116 and electrodes 104A, 104B, 106A, and 106B.

Figure 22:
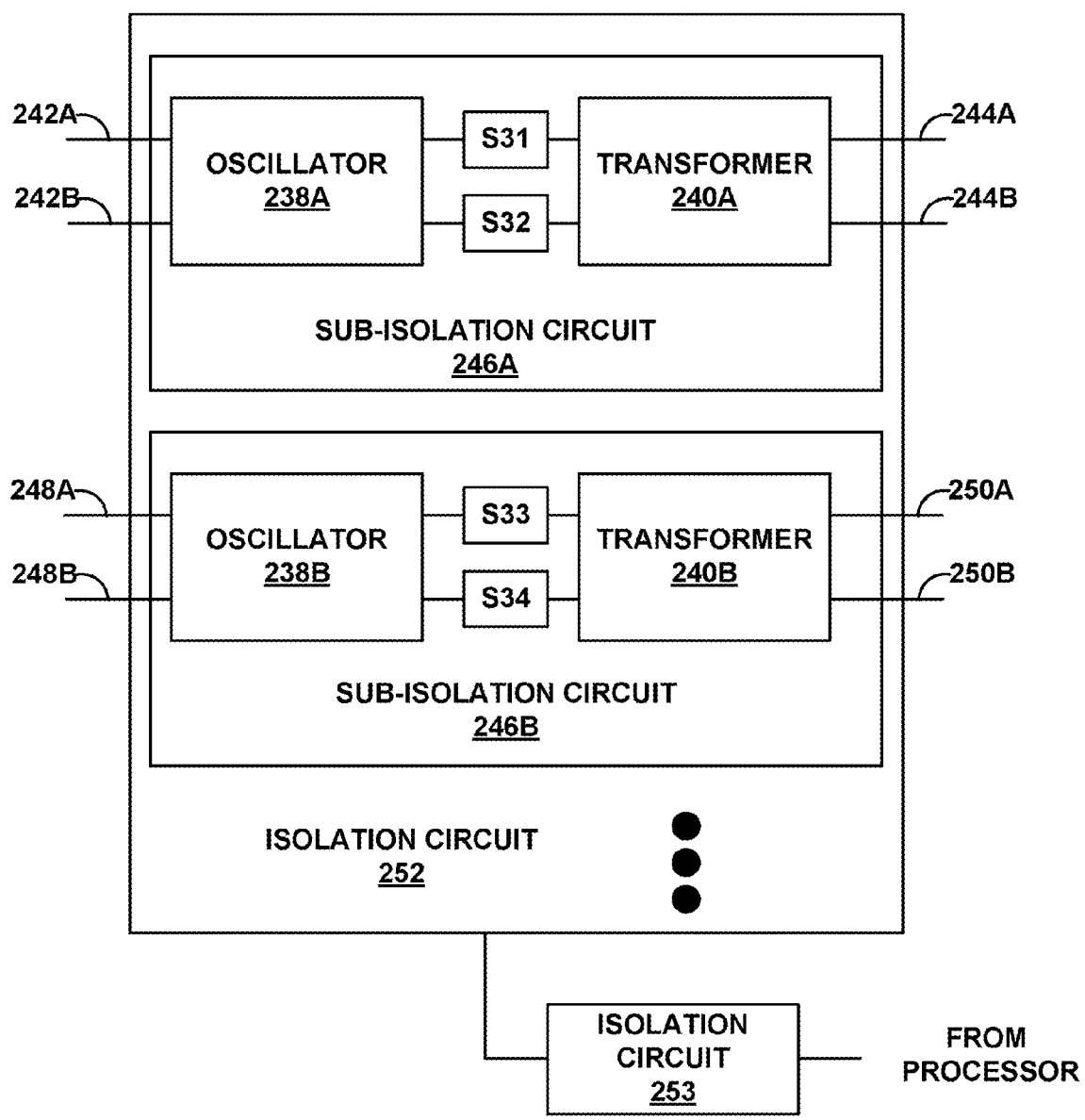
FIG. 22 is a circuit diagram of another example of an isolation circuit.

As described in more detail with respect to FIG. 22, in another example isolation circuit 148 may comprise a plurality of sub-isolation circuits, where each sub-isolation circuit is a transformer circuit as shown in FIG. 22. Each sub-isolation circuit may comprise an oscillator, a plurality of switches, and at least one transformer. The switches may be opened for each sub-isolation circuit for all instances except for when neuro module 116 provides stimulation via isolation circuit 148. Each oscillator within each sub-isolation circuit may be referenced to power source 108 and ground provided by housing 70. In accordance with this disclosure, to deliver stimulation, each oscillator within each sub-isolation circuit may generate a pulse with an amplitude, pulse width, and frequency set by the therapy program. The output of the oscillators may be coupled to a primary side of each of the transformers within each of the sub-isolation circuits. The secondary side of the transformers may be coupled to the switches. Processor 122 may close switches for one of the sub-isolation circuits so that the stimulation is provided through the transformer to electrodes 104A, 104B. Simultaneously, processor 122 may close the switches for another one of the sub-isolation circuits so that the stimulation is provided through the transformer to electrodes 106A, and 106B. Since the switches are open at all times except for when neuro module 116 delivers stimulation via a transformer, there is no commonality and no current path between neuro module 116 and electrodes 104A, 104B, 106A, and 106B.

In accordance with this disclosure, processor 122 provides a control signal via control lines 132A and 132B that are isolated from one another via isolation circuit 128. In the example IMD 16 shown in FIG. 9, processor 122 may provide control signals that cause isolation circuit 148 to output stimulation signals on electrodes 104A, 104B, 106A, and 106B. In examples where there are more electrodes than 104A, 104B, 106A, and 106B, isolation circuit 148 comprises additional sub-isolation circuits that provide stimulation to the additional electrodes.

Similar to FIGS. 7 and 8, isolation circuit 148 reduces or eliminates the power source commonality between cardiac module 114 and neuro module 116 thereby reducing or eliminating common-mode interference. For example, a stimulation generated by isolation circuit 148 may not impose a common voltage, e.g., common-mode interference upon electrode pairs 100A, 100B and 102A, 102B because there is no shared commonality between the output of isolation circuit 148 and cardiac module 114. Accordingly, the common-mode interference may not feed into sensing module 118A. Similarly, a stimulation generated by stimulation generator 120A may not impose a common voltage upon electrode pairs 104A, 104B and 106A, and 106B because there is no shared commonality between the output of isolation circuit 148 and cardiac module 114. Accordingly, the common-mode interference may not feed into sensing module 118B. Furthermore, a shunt current generated by stimulation generator 120A may not feed into electrodes 104A, 104B, 106A, and 106B because, as described above, at least the switches of each of the sub-isolation circuits with isolation circuit 148 may be opened thereby creating a high impedance path for the shunt current. Also a shunt current generated by isolation circuit 148 may not feed into electrodes 100A, 100B, 102A, and 102B because isolation circuit 148 does not allow for a complete current path for the shunt current.

Figure 10:
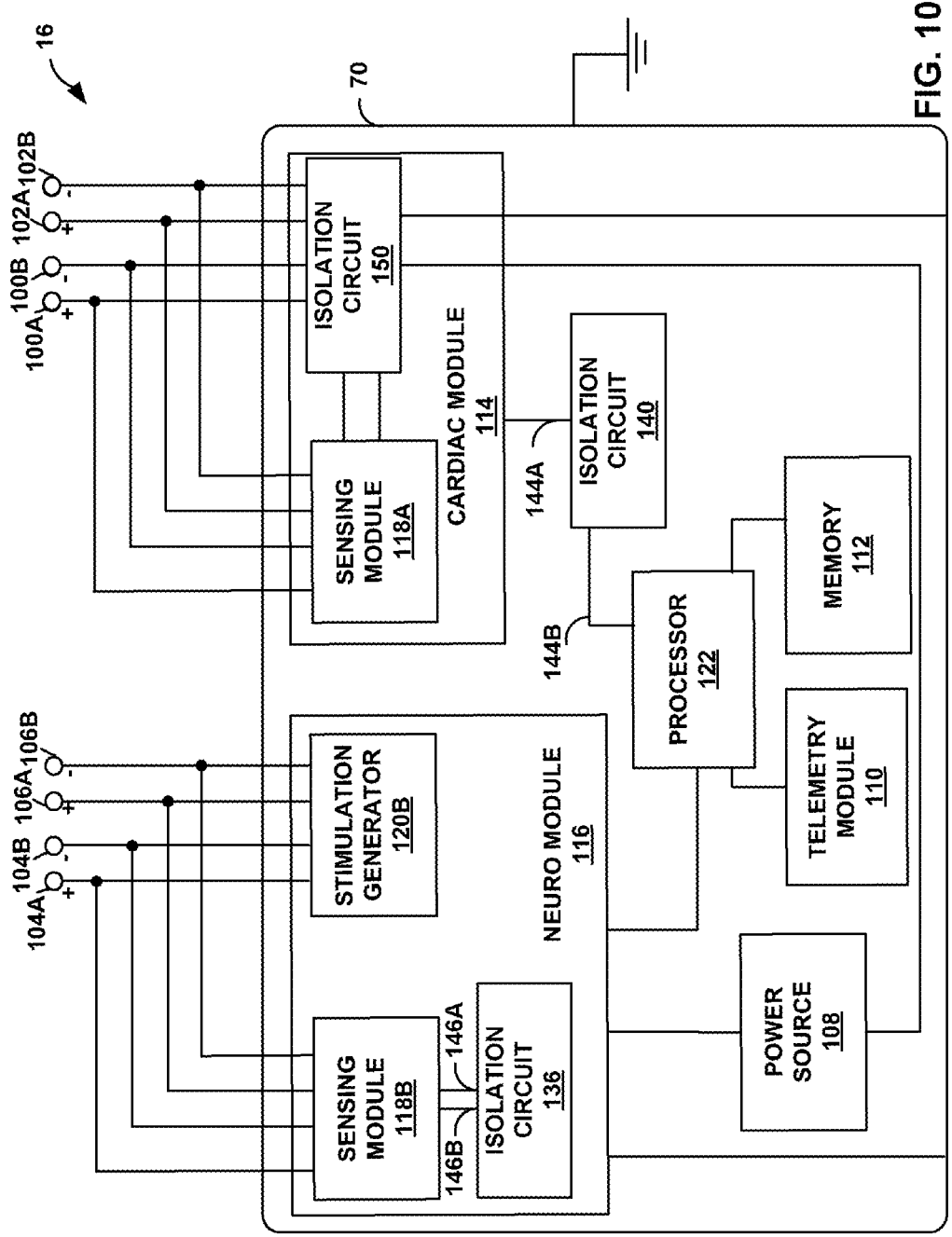
FIG. 10 is a functional block diagram of another example configuration of IMD comprising isolation circuits to reduce or eliminate commonality.

FIG. 10 is a functional block diagram of another example configuration of IMD 16 comprising isolation circuits to reduce or eliminate commonality. The example of IMD 16 shown in FIG. 10 is substantially similar to the example of IMD shown in FIG. 8. However, in the example of IMD 16 shown in FIG. 10 there is no stimulation generator 120A and isolation circuit 138 (FIG. 8). Instead, isolation circuit 150 may provide all the functionality of stimulation generator 120A and isolation circuit 138. In addition, in some examples, isolation circuit 150 may provide power to sensing module 118A. For purposes of clarity, the functionality of neuro module 116, sensing module 118A and 118B, stimulation generator 120A, power source 108, telemetry module 110, memory 112, isolation circuit 136 and 140, control line 144A and 144B, and control line 146A and 146B will be not be described with respect to FIG. 10 since their functionality has already been described with respect to FIG. 8.

Similar to isolation circuit 148 of FIG. 9, isolation circuit 150 reduces or eliminates the power source commonality between cardiac module 114 and neuro module 116. Isolation circuit 150 may be substantially similar to isolation circuit 148. For example, similar to isolation circuit 148, isolation circuit 150 may comprise a plurality of sub-isolation circuits, as described in more detail with respect to FIGS. 21, 22 and 23. Examples of sub-isolation circuits include a flying-capacitor circuit and a transformer circuit, as described in more detail with respect to FIGS. 21, 22 and 23. For example, isolation circuit 150 may comprise three sub-isolation circuits. The first sub-isolation circuits may provide power to sensing module 118A. The remaining two sub-isolation circuits provide stimulation signals to electrodes 100A, 100B, 102A, and 102B. For example, one output of the second sub-isolation circuit may be coupled to electrode 100A, and the other output of the second sub-isolation circuit may be coupled to electrode 100B. One output of the third sub-isolation circuit may be coupled to electrode 102A, and the other output of the third sub-isolation circuit may be coupled to electrode 102B. In accordance with this disclosure, processor 122 provides a control signal via control lines 144A and 144B that are isolated from one another via isolation circuit 140. In the example IMD 16 shown in FIG. 10, processor 122 may provide control signals that cause isolation circuit 150 to output stimulation signals on electrodes 100A, 100B, 102A, and 102B. In examples where there are more electrodes than 100A, 100B, 102A, and 102B, isolation circuit 150 comprises additional sub-isolation circuits that provide stimulation to the additional electrodes.

Isolation circuit 150 may provide stimulation signals substantially similar to isolation circuit 148, as described above with respect to FIG. 9. For example, in instances where the sub-isolation circuits within isolation circuit 150 comprise a flying-capacitor circuit, a capacitor may store charge. Processor 122 may toggle switches within the flying-capacitor circuit that causes the flying-capacitor circuit to discharge the capacitor thereby generating a stimulation signal that is provided to the heart. As another example, as described in more detail below, in instances where the sub-isolation circuit within isolation circuit 150 comprise a transformer circuit, an oscillator within the transformer circuit may generate pulses with a certain amplitude, pulse width, and frequency. When cardiac module 114 needs to output a stimulation, processor 122 may toggle switches to output the signal from the oscillator to a primary side of the transformer. The primary side of the transformer may be coupled to the oscillator, and the secondary side of the transform may be coupled to electrodes 100A and 100B that provide stimulation to the heart. In this manner, isolation circuit 150 may function as a stimulation generator.

Isolation circuit 150 reduces or eliminates the power source commonality between cardiac module 114 and neuro module 116 thereby reducing or eliminating common-mode interference in a substantially similar manner as described above with respect to isolation circuit 148. Additionally, isolation circuit 150 reduces or eliminates shunt currents in a substantially similar manner as described above with respect to isolation circuit 148.

As described so far, the various examples of IMD 16 described with respect to FIGS. 7-10 describe placing isolation circuits in various locations within IMD 16 to reduce or eliminate the commonality between cardiac module 114 and neuro module 116. Particularly, in the examples described in FIGS. 7-10, cardiac module 114 and neuro module 116 share common circuitry such as a processor, telemetry module, and memory. However, aspects of this disclosure are not so limited. As described with respect to FIG. 5, in some examples, cardiac module 114 and neuro module 116 do not share a common processor, telemetry module, and memory, but instead share a common power source. In such examples, isolation circuits may be placed in various locations to reduce or eliminate the commonality between cardiac module 114 and neuro module 116.

Figure 11:
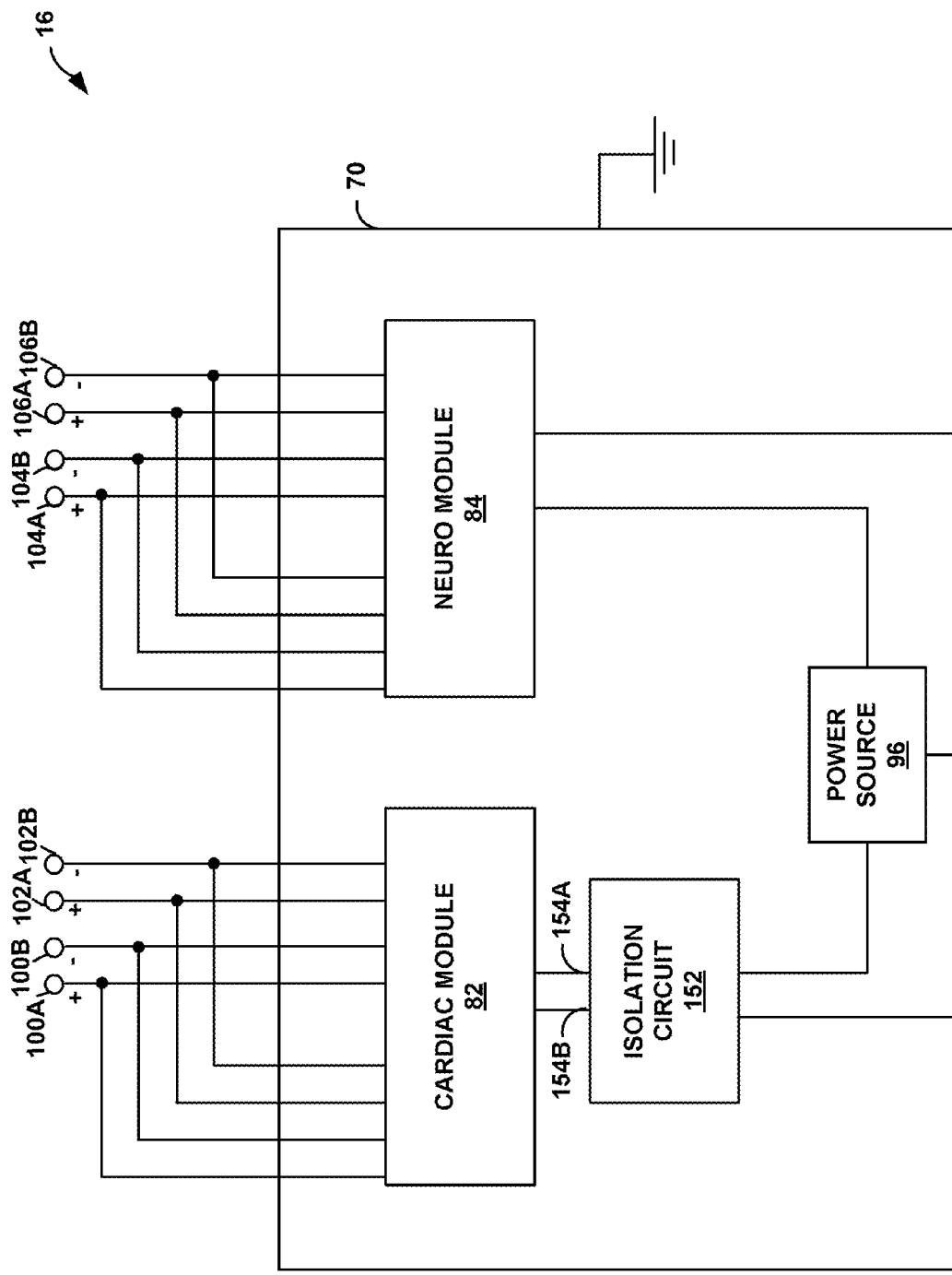
FIG. 11 is a functional block diagram of another example configuration of IMD comprising isolation circuits to reduce or eliminate commonality.

FIG. 11 is a functional block diagram of another example configuration of IMD 16 comprising isolation circuits to reduce or eliminate commonality. As shown in FIG. 11, IMD 16 comprises cardiac module 82, neuro module 84, and power source 96. Cardiac module 82, neuro module 84, and power source 96 are substantially similar to cardiac module 82, neuro module 84, and power source 96 (FIG. 5), respectively. For purposes of clarity, the various components within cardiac module 82 and neuro module 84, as shown in FIG. 5, are not shown in FIG. 11. The example of IMD 16 shown in FIG. 11 also includes isolation circuit 152.

Isolation circuit 152 may be substantially similar to isolation circuit 124, 126 (FIG. 7) 136, or 138 (FIG. 8). Isolation circuit 152 reduces or eliminates the commonality between cardiac module 82 and neuro module 84. Examples of isolation circuit 152 include a flying-capacitor circuit, a transformer circuit, a barrier circuit, and a photo-voltaic cell as shown in FIGS. 16, 18, 19, and 20. Cardiac module 82 and neuro module 84 share power source 96. Neuro module 84 receives power from power source 96 referenced to the ground provided by housing 70. Isolation circuit 152 receives voltage from power source 96 is that referenced to the ground provided by housing 70. Isolation circuit 152 outputs a floating power and floating ground. The floating power and floating ground are provided to cardiac module 82 via power line 154A and ground line 154B, respectively. The outputs of isolation circuit 152 are referred to as floating power and floating ground because neither are referenced to power source 96 or the ground provided by housing 70. Instead, the outputs of isolation circuit 152 are only referenced to one another. The various control lines within cardiac module 82 and neuro module 84 do not require isolation circuits because there is no commonality between the various components within cardiac module 82 and neuro module 84.

The common-mode interference and shunt currents may be reduced or eliminated due to isolation circuit 152. A stimulation generated by neuro module 84 may not impose a common voltage upon electrode pairs 104A, 104B and 106A, 106B because the commonality between cardiac module 82 and neuro module 84 is reduced or eliminated. Additionally, a stimulation provided by cardiac module 82 may not impose a common voltage, e.g., common-mode interference, upon electrodes coupled to neuro module 84 because the stimulation signal generated by cardiac module 82 is not referenced to the ground provided by housing 70, e.g., the commonality is reduced or eliminated. Furthermore, a shunt current generated by cardiac module 82 may not feed into neuro module 84 because isolation circuit 152 provides a high impedance barrier within the complete current path for the shunt current. Similarly, a shunt current generated by neuro module 84 may not feed into cardiac module 82 because isolation circuit 152 provides a high impedance for the shunt current.

Figure 12:
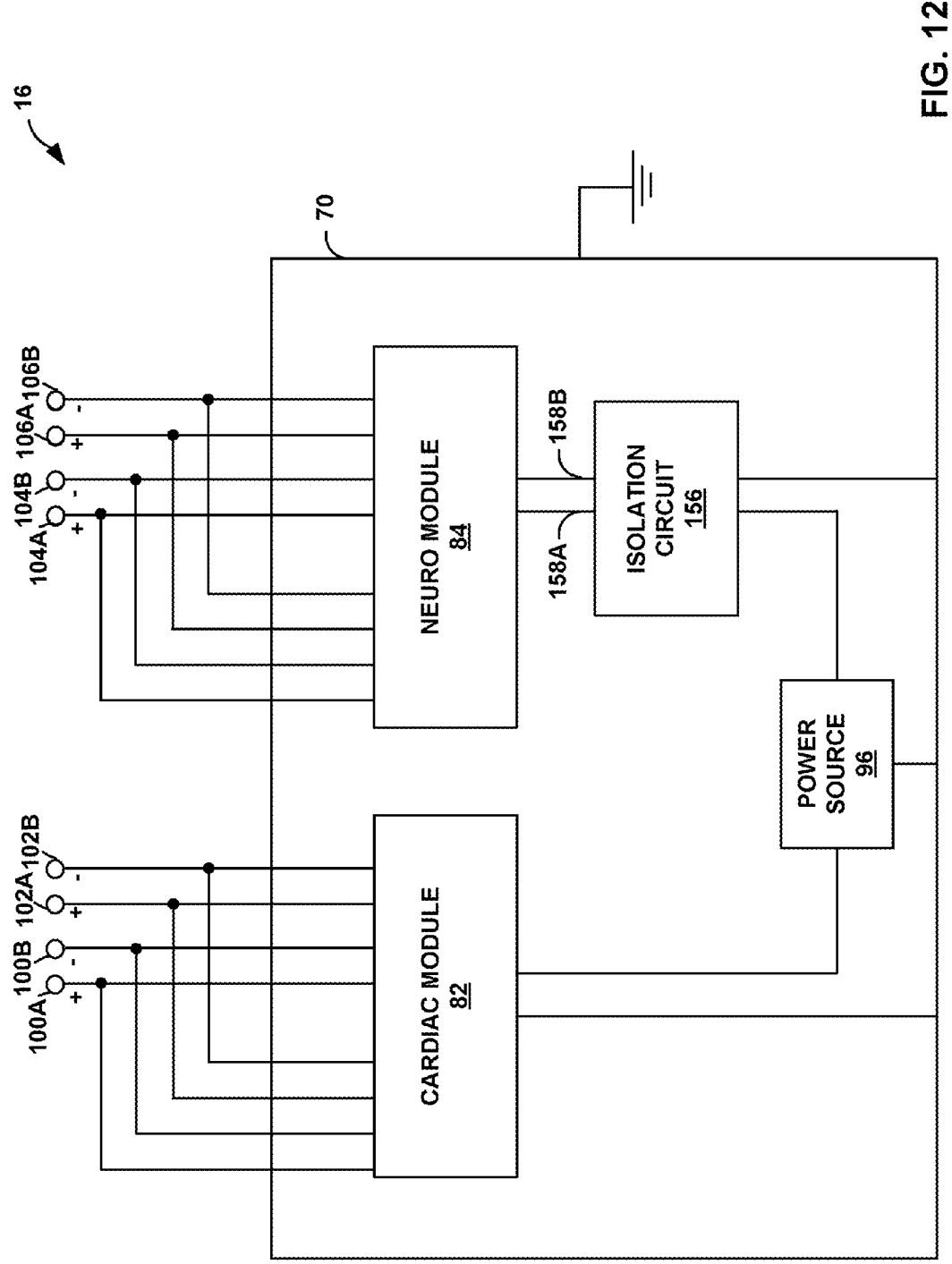
FIG. 12 is a functional block diagram of another example configuration of IMD comprising isolation circuits to reduce or eliminate commonality.

FIG. 12 is a functional block diagram of another example configuration of IMD 16 comprising isolation circuits to reduce or eliminate commonality. The example of IMD 16 shown in FIG. 12 is substantially similar to the example of IMD 16 shown in FIG. 11. Isolation circuit 156 is substantially similar to isolation circuit 152, e.g., similar to isolation circuit 126, 128 (FIG. 7), 136, and 138 (FIG. 8). However, isolation circuit 156 provides floating power and floating ground to neuro module 84 via power line 158A and ground line 158B. Power source 96 provides power to cardiac module 82.

Similar to FIG. 11, the common-mode interference and shunt currents may be reduced or eliminated due to isolation circuit 156. A stimulation generated by cardiac module 82 may not impose a common voltage upon electrode pairs 100A, 100B and 102A, 102B because the commonality between cardiac module 82 and neuro module 84 is reduced or eliminated. Additionally, a stimulation provided by cardiac module 82 may not impose a common voltage, e.g., common-mode interference, upon electrodes coupled to neuro module 84 because the stimulation signal generated by cardiac module 82 is not referenced to the ground provided by housing 70, e.g., the commonality is reduced or eliminated. Additionally, a stimulation provided by neuro module 84 may not impose a common voltage, e.g., common-mode interference, upon electrodes coupled to cardiac module 82 because the stimulation signal generated by neuro module 84 is not referenced to the ground provided by housing 70, e.g., the commonality is reduced or eliminated. Furthermore, a shunt current generated by neuro module 84 may not feed into cardiac module 82 because isolation circuit 156 provides a high impedance barrier within the complete current path for the shunt current. Similarly, a shunt current generated by cardiac module 82 may not feed into neuro module 84 because isolation circuit 156 provides a high impedance for the shunt current.

As described so far, the cardiac therapy module, e.g., cardiac module 82 or cardiac module 114, and the neuro therapy module, e.g., neuro module 84 or neuro module 116, are isolated from one another by isolating the power source and control lines. However, in some examples, cardiac module 82 and neuro module 84, or cardiac module 114 and neuro module 116, may be isolated from one another by isolating the stimulation output, e.g., stimulation generated by the cardiac therapy device and the neuro therapy device, and/or isolating the sensing input, e.g., signals sensed by the cardiac therapy module and the neuro therapy module.

Figure 13:
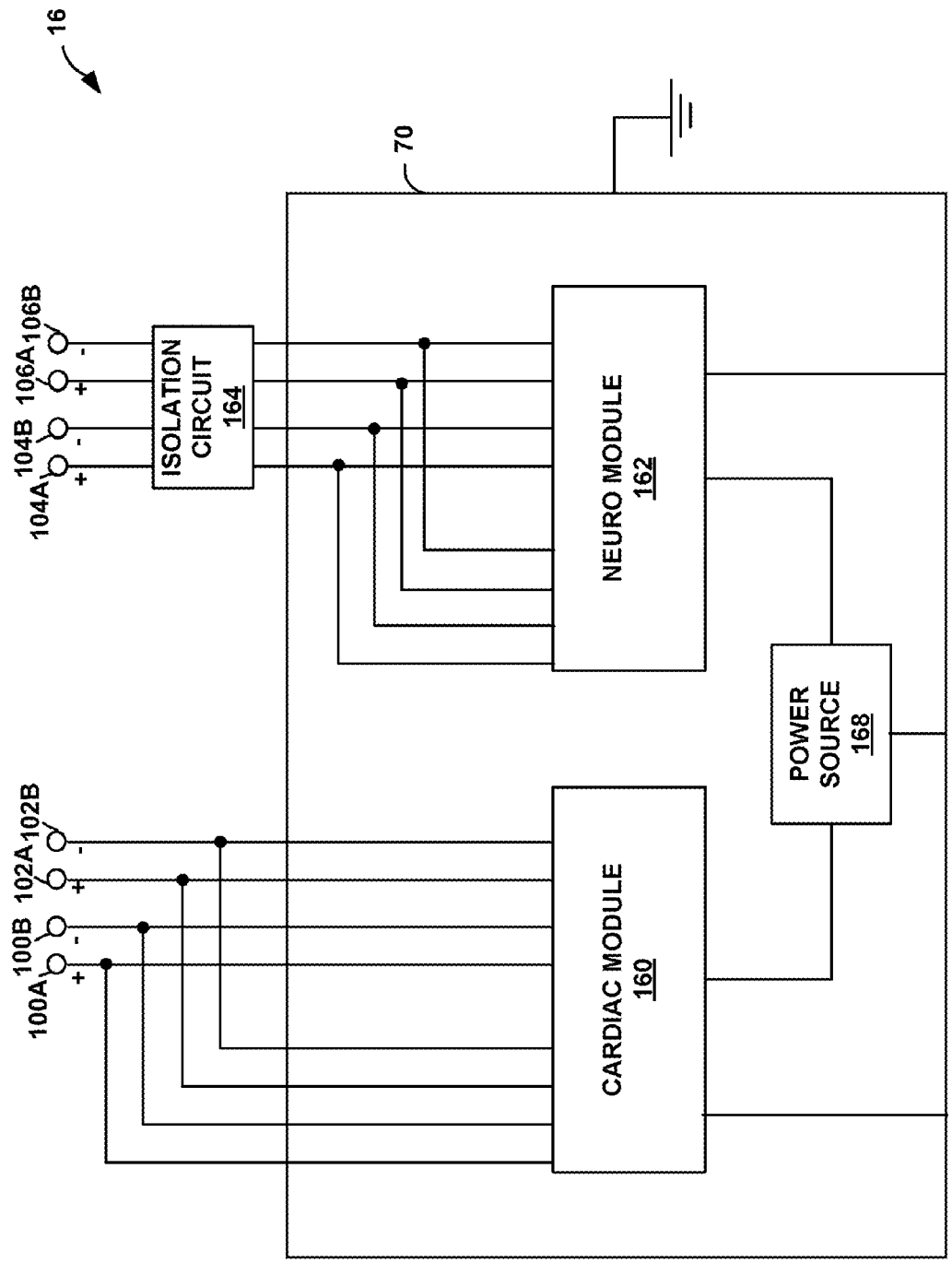
FIG. 13 is a functional block diagram of another example configuration of IMD comprising isolation circuits to reduce or eliminate commonality.

FIG. 13 is a functional block diagram of another example configuration of IMD 16 comprising isolation circuits to reduce or eliminate commonality. The example of IMD 16 shown in FIG. 13 includes cardiac module 160, neuro module 162, power source 164, and isolation circuit 164. Cardiac module 160 may be substantially similar cardiac module 82 or cardiac module 114. Neuro module 162 may be substantially similar to neuro module 84 or neuro module 116. For purposes of clarity, the various other components within IMD 16 are not shown. For example, in instances where cardiac module 160 is substantially similar to cardiac module 82 and where neuro module 162 is substantially similar to neuro module 84, the various components within cardiac module 82 and neuro module 84 (shown in FIG. 5) are not shown in FIG. 13. Similarly, in instances where cardiac module 160 is substantially similar to cardiac module 114 and where neuro module 162 is substantially similar to neuro module 116, the various components within cardiac module 114, neuro module 116, the common shared circuitry, and the control line isolation circuits (shown in FIGS. 6 and 8) are not shown in FIG. 13.

In accordance with this disclosure, isolation circuit 164 reduces or eliminates the commonality between the stimulation generated by a stimulation output of neuro module 162 that may be sensed by a sensing input of cardiac module 160 and the stimulation generated by a stimulation output of cardiac module 160 that may be sensed by a sensing input of neuro module 162. Due to the stimulation and sensing isolation between cardiac module 160 and neuro module 162, the common-mode interference and the shunt current may be reduced or eliminated. As shown in FIG. 13, isolation circuit 164 may be external to housing 70. However, aspects of this disclosure are not so limited. In some examples, isolation circuit 164 may be enclosed within housing 70. For example, isolation circuit may be enclosed within housing 70 but external to neuro module 162. In some examples, isolation circuit 164 may be enclosed within, carried by or otherwise integrated with neuro module 162. In some examples, isolation circuit 164 may be enclosed within a connector of a lead that includes electrodes 104A, 104B, 106A, and 106B. In some examples, isolation circuit 164 maybe enclosed within a lead that includes electrodes 104A, 104B, 106A, and 106B.

As shown in FIG. 13, power source 168 provides power to both cardiac module 160 and neuro module 162. Neuro module 162 generates stimulation signals that are referenced to the power source 168 and the ground provided by housing 70. Isolation circuit 164 receives the stimulation signals and outputs stimulation signals that are no longer referenced to power source 168. Instead, the stimulation signals are referenced to one another. For example, a stimulation signal may be referenced between 104A and 104B and not be referenced to power source 168 and the ground provided by housing 70. Isolation circuit 164 may comprise a plurality of sub-isolation circuits each coupled to an electrode pair. For example, isolation circuit 164 may comprise two sub-isolation circuits. One output of the first sub-isolation circuit may be coupled to electrode 104A, and the other output of the first sub-isolation circuit may be coupled to electrode 104B. One output of the second sub-isolation circuit may be coupled to electrode 106A, and the other output of the second sub-isolation circuit may be coupled to electrode 106B. In this manner, the stimulation provided by electrodes 104A, 104B, 106A, and 106B is not referenced cardiac module 160 which in turn reduces or eliminates the crosstalk or common-mode interference. Moreover, for purposes of clarity, isolation circuit 164 is shown outside of neuro module 162. However, in some aspects, isolation circuit 164 may be comprised within neuro module 162.

Figure 23:
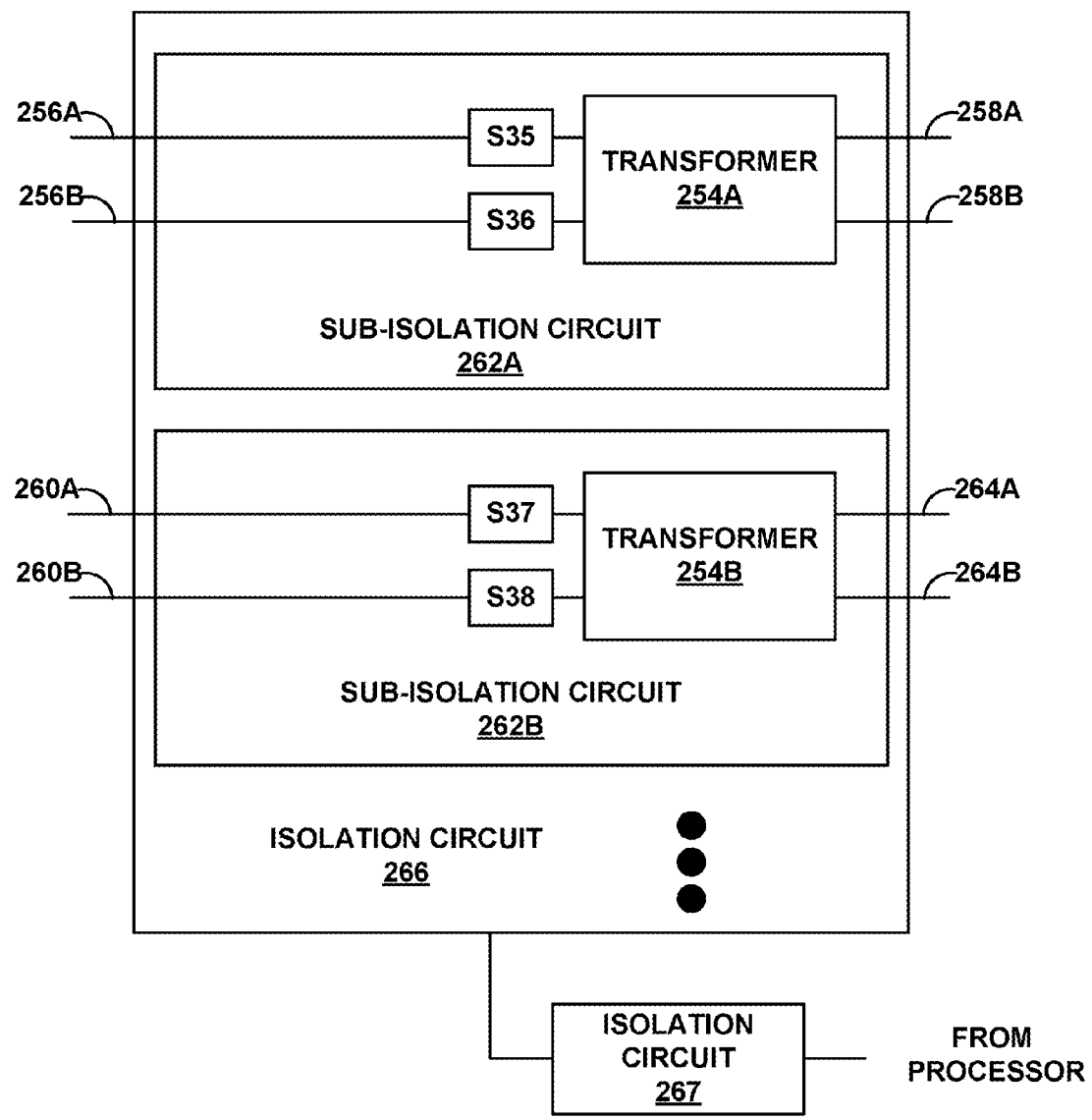
FIG. 23 is a circuit diagram of another example of an isolation circuit.

As described in more detail below, examples of isolation circuit 164 include a flying-capacitor circuit and a transformer circuit, as shown in FIGS. 21, 22, and 23. In some examples, the processor or processors, e.g., processor 86B (FIG. 5) or processor 122 (FIG. 6), within IMD 16 provide control signals that cause isolation circuit 164 to output the stimulation signal. In examples where isolation circuit 164 is a flying-capacitor circuit, isolation circuit 164 comprises a plurality of sub-isolation circuits, each of the sub-isolation circuits may be a flying-capacitor circuit, as shown in FIG. 21. Isolation circuit 164 may comprise a plurality of switches and at least one capacitor. A first set of switches may be coupled to neuro module 162 and a second set of switches may be coupled to various electrode pairs, e.g. either electrodes 104A and 104B or 106A and 106B. To provide stimulation, neuro module 162 may close the first set of switches to charge the capacitor to a preset value, e.g., the stimulation amplitude level set by the therapy program. After the capacitor is charged, the first set of switches may open and the second set of switches may be closed to output the stimulation to electrodes 104A, 104B, 106A, and 106B. In another example, a processor within neuro module 162 may toggle the second set of switches according to the pulse width and frequency set by the therapy program to provide stimulation in accordance with the therapy program. Either the first set of switches or the second set of switches is opened while the other is closed. Accordingly, there is no commonality between the stimulation generated by neuro module 162 and the ground provided by housing 70.

To sense a signal, a processor within neuro module 162 may close the second set of switches and open the first set of switches. The toggling of switches may utilize a sampling of the sensed signal, typically at a sampling rate that is sufficient to accurately capture the signal as it fluctuates. For example, the sampling rate may be two or more times higher than the highest frequency component intended to be present at the input to the switches. The capacitor may be charged by the signal that is to be sensed. After the capacitor is charged, neuro module 162 may open the second set of switches and close the first set of switches. Similar to the stimulation, either the first set of switches or the second set of switches is opened while the other is closed. Accordingly, there is no commonality between the stimulation generated by neuro module 162 and the ground provided by housing 70.

In examples where isolation circuit 164 is a transformer circuit, isolation circuit 164 comprises a plurality of sub-isolation circuit, each of the sub-isolation circuits may be a transformer circuit, as substantially shown in FIG. 23. Accordingly, in examples where isolation circuit 164 is a transformer circuit, neuro module 162 may couple directly to a plurality of switches. To provide stimulation neuro module 162 may toggle the plurality of switches to provide the stimulation to the transformer. In some examples, neuro module 162 may open and close the plurality of switches at a frequency and pulse width set by the therapy program. The switches may be open at all times except for when neuro module 162 provides stimulation. Also, the transformer reduces or eliminates the commonality between the stimulation generated by neuro module 162 and cardiac module 160.

To sense a signal, a processor within neuro module 162 may close the switches to allow the signal to feed into neuro module 162. The switches may be opened at all times except for when neuro module 162 senses the signal.

A stimulation generated by neuro module 162 may not impose a common voltage upon electrode pairs 100A, 100B, and 102A, 102B as common-mode interference because the stimulation generated by neuro module 162 shares no commonality with the ground provided by housing 70 due to the transformer(s) within isolation circuit 164. Furthermore, a shunt current generated by cardiac module 160 may not feed into neuro module 162 because as described above, the switches will be opened, creating a high impedance path for the shunt current.

In some examples, various switches within isolation circuit 164 may be opened at all times expect for when neuro module 162 transmits a stimulation, senses a physiological condition of the patient, or performs an impedance measurement of the tissue or electrodes. The switches with isolation circuit 162 may be closed only to provide stimulation or to sense or measure impedance. In this manner, the shunt current may be reduced or eliminated since the switches are open at all times except for brief intervals when neuro module 162 provides stimulation or to sense or measure impedance. In some examples, the impedance measurement may be disabled when a shunt current condition is expected, e.g., when defibrillation is invoked.

As shown in FIG. 13, isolation circuits are provided on the stimulation output and sensing input of neuro module 162. However, in some aspects, isolation circuits may be provided on the stimulation output and sensing input of cardiac module 160. The isolation circuit may perform substantially similar to isolation circuit 164.

Figure 14:
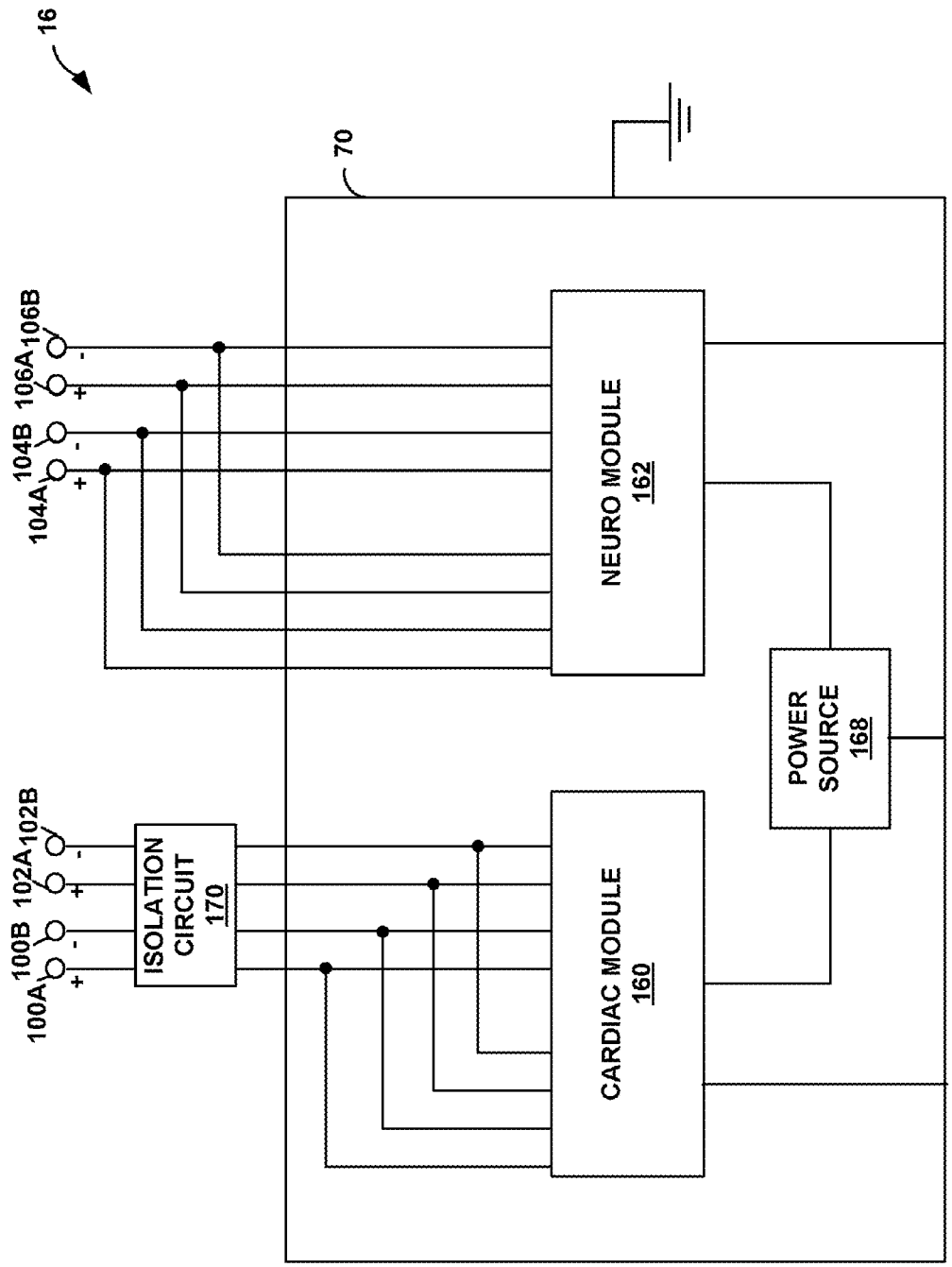
FIG. 14 is a functional block diagram of another example configuration of IMD comprising isolation circuits to reduce or eliminate commonality.

FIG. 14 is a functional block diagram of another example configuration of IMD 16 comprising isolation circuits to reduce or eliminate commonality. The example of IMD 16 shown in FIG. 14 includes cardiac module 160, neuro module 162, power source 168, and isolation circuit 170. Similar to FIG. 13, for purposes of clarity, the various additional components within cardiac module 160, neuro module 162, and any common shared circuitry is not shown.

Isolation circuit 170 may be substantially similar to isolation circuit 164. In accordance with this disclosure, isolation circuit 170 reduces or eliminates the common-mode interference and the shunt current between cardiac module 160 and neuro module 162. As shown in FIG. 14, isolation circuit 170 may be external to housing 70. However, aspects of this disclosure are not so limited. In some examples, isolation circuit 170 may be enclosed within housing 70. For example, isolation circuit may be enclosed within housing 70 but external to cardiac module 160. In some examples, isolation circuit 170 may be enclosed within, carried by, or otherwise integrated with cardiac module 162. In some examples, isolation circuit 170 may be enclosed within a connector of a lead that includes electrodes 100A, 100B, 102A, and 102B. In some examples, isolation circuit 170 may be enclosed within a lead that includes electrodes 100A, 100B, 102A, and 102B.

Similar to the example of IMD 16 shown in FIG. 13, power source 168 provides power to both cardiac module 160 and neuro module 162. Cardiac module 160 generates stimulation signals that are referenced to the power source 168 and the ground provided by housing 70. Isolation circuit 170 receives the stimulation signals and outputs stimulation signals that are no longer referenced to power source 168. Instead, the stimulation signals are referenced to one another. For example, a stimulation signal may be referenced between 100A and 100B and not be referenced to power source 168 and the ground provided by housing 70. Isolation circuit 170 may comprise a plurality of sub-isolation circuits each coupled to an electrode pair. For example, isolation circuit 170 may comprise two sub-isolation circuits. One output of the first sub-isolation circuit may be coupled to electrode 100A, and the other output of the first sub-isolation circuit may be coupled to electrode 100B. One output of the second sub-isolation circuit may be coupled to electrode 102A, and the other output of the second sub-isolation circuit may be coupled to electrode 102B. In this manner, the stimulation provided by electrodes 100A, 100B, 102A, and 102B is not referenced neuro module 162 which in turn reduces or eliminates the crosstalk or common-mode interference. Moreover, for purposes of clarity, isolation circuit 170 is shown outside of cardiac module 160. However, in some examples, isolation circuit 170 may be located within cardiac module 160.

Isolation circuit 170 may reduce or eliminate commonality in a manner substantially similar to isolation circuit 164. For example, isolation circuit 170 may comprise one or more sub-isolation circuits that are flying-capacitor circuits as shown in FIG. 21. In some examples, isolation circuit 170 may comprise one or more sub-isolation circuits that are transformer circuits as substantially shown in FIGS. 22 and 23. The stimulation generated by cardiac module 160 may not impose a common voltage as common-mode interference because there is no commonality between the stimulation generated by cardiac module 160 and the ground provided by housing 70 due to isolation circuit 170. Similarly, no shunt current may flow into cardiac module 160 because, as described above, the switches within isolation circuit 170 may be open at all times except for when cardiac module 160 provides stimulation or senses the signal.

Stated another way, in some examples, various switches within isolation circuit 170 may be opened at all times expect for when cardiac module 160 transmits a stimulation signal, senses a physiological condition of the patient, or performs an impedance measurement of the tissue or electrodes. The switches with isolation circuit 170 may be closed only to provide stimulation or to sense or measure impedance. In this manner, the shunt current may be reduced or eliminated since the switches are open at all times except for brief intervals immediately prior to and while cardiac module 160 provides stimulation or to sense or measure impedance.

The various examples of IMD 16 shown in FIGS. 7-14 show one or more isolation circuits located at various locations within IMD 16. In some aspects, IMD 16 may be a combination of one or more examples of IMD 16 as shown in FIGS. 7-14. For example, IMD 16 may comprise isolation circuits as shown in FIGS. 7 and 8. As another example, IMD 16 may comprise isolation circuits as shown in FIGS. 11 and 12. As yet another example, IMD 16 may comprise isolation circuits as shown in FIGS. 11-14. Many such combinations are possible, and all are contemplated by this disclosure.

FIG. 15A is a circuit diagram of an example of an isolation circuit 172A. Isolation circuit 172A may, for example, be one or more of isolation circuit 128 (FIGS. 7 and 9) and isolation circuit 140 (FIGS. 8 and 10). As shown in FIG. 15A, isolation circuit 172A comprises at least two resistors, resistors R1 and R2. Each of resistors R1 and R2 may have a impedance value of approximately 10 kiloohms to approximately 2 megaohms, as one non-limiting example. Resistor R1 may couple processor 122 to a therapy module. For example, with respect to FIGS. 7 and 9, resistor R1 may couple processor 122 to neuro module 116. In such examples, control line 132A may comprise the connection between processor 122 and resistor R1 and control line 132B may comprise the connection between resistor R1 and neuro module 116. Control lines 132A and 132B may comprise a communication line between processor 122 and neuro module 116. As another example, with respect to FIGS. 8 and 10, resistor R1 may couple processor 122 to cardiac module 114. In such examples, control line 144A may comprise the connection between processor 122 and resistor R1 and control line 144B may comprise the connection between resistor R1 and cardiac module 114. Control lines 144A and 144B may comprise a communication line between processor 122 and cardiac module 114. In examples where control lines 132A, 132B or control lines 144A, 144B comprise a plurality of control lines, isolation circuit 172A may comprise resistors in addition to resistors R1 and R2, that couple each one of control lines 132A or 144A to their respective control lines 132B or 144B.

Resistor R2 couples the ground provided by housing 70 to floating ground line 130B (FIGS. 7 and 9) or floating ground line 142B (FIGS. 8 and 10). The coupling of the ground provided by housing 70 to the floating ground provides a reference voltage for proper measurement of the signals through control lines 132A, 132B, 144A, and 144B.

The coupling of processor 122 to the therapy module, e.g., cardiac module 144 or neuro module 116, may create some commonality between neuro module 116 and cardiac module 114 via processor 122. Similarly, the coupling of the ground provided by housing 70 and floating ground line 132B or 142B may create some commonality between neuro module 116 and cardiac module 114. Although there may be some commonality between neuro module 116 and cardiac module 114, due to the high impedance of resistors R1 and R2, the shunt current may still be mitigated, i.e., there is a high impedance path of the shunt current between cardiac module 114 and neuro module 116. Similarly, the common-mode interference may also be mitigated due to the high impedance of resistors R1 and R2. In other words, the commonality created by resistors R1 and R2 may be sufficient to allow proper transfer of signals between processor 122 and the therapy module. However, the commonality may not be sufficient to appreciably affect the shunt current mitigation and common-mode interference mitigation described in this disclosure.

FIG. 15B is a circuit diagram of another example of an isolation circuit 172B. Isolation circuit 172B may, for example, be one or more of isolation circuit 128 (FIGS. 7 and 9) and isolation circuit 140 (FIGS. 8 and 10). As shown in FIG. 15B, isolation circuit 172B comprises at least two capacitors, capacitors C1 and C2. Each of capacitors C1 and C2 may have a capacitance value in a range of approximately 100 pico-farads to about 1 micro-farad, as one non-limiting example. Capacitor C1 may couple processor 122 to a therapy module. For example, with respect to FIGS. 7 and 9, capacitor C1 may couple processor 122 to neuro module 116. In such examples, control line 132A may comprise the connection between processor 122 and capacitor C1 and control line 132B may comprise the connection between capacitor C1 and neuro module 116. Control lines 132A and 132B may comprise a communication line between processor 122 and neuro module 116. As another example, with respect to FIGS. 8 and 10, capacitor C1 may couple processor 122 to cardiac module 114. In such examples, control line 144A may comprise the connection between processor 122 and capacitor C1 and control line 144B may comprise the connection between capacitor C1 and cardiac module 114. Control lines 144A and 144B may comprise a communication line between processor 122 and cardiac module 114. In examples where control lines 132A, 132B or control lines 144A, 144B comprise a plurality of control lines, isolation circuit 172B may comprise additional capacitors, more than capacitors C1 and C2, that couple each one of control lines 132A or 144A to their respective control lines 132B or 144B.

Capacitor C2 couples the ground provided by housing 70 to floating ground line 130B (FIGS. 7 and 9) or floating ground line 142B (FIGS. 8 and 10). The coupling of the ground provided by housing 70 to the floating ground provides a reference voltage for proper measurement of the signals through control lines 132A, 132B, 144A, and 144B.

Similar to FIG. 15A, the coupling of processor 122 to the therapy module, e.g., cardiac module 144 or neuro module 116, may create some commonality between neuro module 116 and cardiac module 114 via processor 122. Similarly, the coupling of the ground provided by housing 70 and floating ground line 132B or 142B may create some commonality between neuro module 116 and cardiac module 114. However, capacitors C1 and C2 may block DC voltages since capacitors C1 and C2 are high impedance for voltages at low frequencies. The commonality created by capacitors C1 and C2 may be sufficient to allow proper transfer of signals between processor 122 and the therapy module. However, the commonality may not be sufficient to appreciably affect the shunt current mitigation and common-mode interference mitigation described in this disclosure.

FIG. 15C is a circuit diagram of another example of an isolation circuit 172C. Isolation circuit 172C may, for example, be one or more of isolation circuit 128 (FIGS. 7 and 9) and isolation circuit 140 (FIGS. 8 and 10). As shown in FIG. 15C, isolation circuit 172C comprises at least one transformer. The primary winding of the transformer may couple to processor 122 and the ground provided by housing 70 via control line 132A (FIGS. 7 and 9) or control line 144A (FIGS. 8 and 10). The secondary winding of the transformer may couple to the therapy module, e.g., neuro module 116 or cardiac module 114 and the floating ground line, e.g., 130B or 142B. In examples where control lines 132A, 132B or control lines 144A, 144B comprise a plurality of control lines, isolation circuit 172C may comprise a multiple tap transformer where each tap couples each one of control lines 132A or 144A to their respective control lines 132B or 144B. In some examples, isolation circuit 172C may comprise a piezoelectric transformer.

The transformer may eliminate a direct electrical connection between control lines 132A or 144A and control lines 132B and 144B. Similarly, the transformer may eliminate a direct electrical connection between the ground provided by housing 70 and floating ground line 130B or 142B. Stated another way, the signal on the primary may be referenced to the ground provided by housing 70 and the signal on the secondary may be referenced to floating ground line 130B or 144B. Because the transformer transfers signals via inductively coupled conductors, there is no direct electrical connection between control lines 132A and 132B and control lines 144A and 144B. Similarly, there is no direct electrical connection between the ground provided by housing 70 and floating ground line 130B or 142B. In some cases, processor 122 may provide digital signals to digital circuitry in neuro module 116 or cardiac module 114. In other cases, processor 122 may include digital-to-analog (DAC) circuitry to provide analog signals to neuro module 116 or cardiac module 114. In each case, isolation circuit 172A, 172B, or 172C may be provided to reduce or eliminate commonality between processor 122 and the pertinent module 114, 116. Accordingly, the transformer may reduce or eliminate the commonality between cardiac module 114 and neuro module 116 via processor 122.

FIG. 15D is a circuit diagram of another example of an isolation circuit 172D. Isolation circuit 172D may, for example, be one or more of isolation circuit 128 (FIGS. 7 and 9) and isolation circuit 140 (FIGS. 8 and 10). As shown in FIG. 15D, isolation circuit 172D comprises opto-isolator 174A and opto-isolator 174B. Opto-isolator 174A may allow transmission of signals from processor 122 to the therapy module, e.g., cardiac module 114 or neuro module 116. Opto-isolator 174B may allow transmission of signals from the therapy module to processor 122. The opto-isolators convert the electrical signal into an optical signal and back to an electrical signal. The electrical connection between control line 132A and 132B or control line 144A and 144B may be eliminated because the data is provided optically. Accordingly, opto-isolators 174A and 174B may reduce or eliminate the commonality between cardiac module 114 and neuro module 116 via processor 122. Examples of opto-isolators include opto-relays, opto-transistors, opto-field effect transistors (FETs), opto-silicon controlled rectifier (SCR).

Similar to above, in examples where control lines 132A, 132B and control lines 144A, 144B comprise a plurality of control lines in parallel, isolation circuit 172D may comprise a plurality of opto-isolators. Isolation circuit 172D may comprise a plurality of opto-isolators where each opto-isolator couples each one of the plurality of control lines. Notably, opto-isolators that transmit data from the therapy module to processor 122 and opto-isolators that transmit data from the processor to the therapy module may be needed for each of the plurality of control lines.

FIG. 15E is a circuit diagram of another example of an isolation circuit 172E. Isolation circuit 172E may, for example, serve as one or more of isolation circuit 128 (FIGS. 7 and 9) and isolation circuit 140 (FIGS. 8 and 10). As shown in FIG. 15E, isolation circuit 172E comprises photo-voltaic cell 176A and photo-voltaic cell 176B. Photo-voltaic cells 176A may comprise an LED, or a similar device, that illuminates in response to the signal provided by processor 122. When the LED is illuminated a current and voltage is generated on the cell within photo-voltaic cell 176A. The voltage from photo-voltaic cell 176A may form the signal to the therapy module. It should be noted that an insulative barrier exists between the cell and the LED. Similarly, photo-voltaic cell 176B may comprise an LED, or a similar device, that illuminates in response to the signal provided by the therapy module, e.g., cardiac module 114 or neuro module 116. When the LED is illuminated a current and voltage is generated on the cell within photo-voltaic cell 176B. The voltage from photo-voltaic cell 176B may form the signal to processor 122.

Photo-voltaic cell 176A may provide power or allow transmission of signals, e.g., in the form of voltage or current, from processor 122 to the therapy module, e.g., cardiac module 114 or neuro module 116. Photo-voltaic cell 176B may provide power or allow transmission of signals from the therapy module to processor 122. The photo-voltaic cells convert the electrical signal into an optical signal and back to an electrical signal. The electrical connection between control line 132A and 132B or control line 144A and 144B may be eliminated because the data is provided optically. Accordingly, photo-voltaic cells 176A and 176B may reduce or eliminate the commonality between cardiac module 114 and neuro module 116 via processor 122.

Similar to above, in examples where control lines 132A, 132B and control lines 144A, 144B comprise a plurality of control lines in parallel, isolation circuit 172E may comprise a plurality of photo-voltaic cells. Isolation circuit 172E may comprise a plurality of photo-voltaic cells where each photo-voltaic cell couples each one of the plurality of control lines. Notably, photo-voltaic cells that transmit data from the therapy module to processor 122 and photo-voltaic cells that transmit data from the processor to the therapy module may be needed for each of the plurality of control lines.

FIG. 15F is a circuit diagram of another example of an isolation circuit 172F. Isolation circuit 172F may, for example, be one or more of isolation circuit 128 (FIGS. 7 and 9) and isolation circuit 140 (FIGS. 8 and 10). As shown in FIG. 15F, isolation circuit 172F comprises solid state memory device 178 and switches S1-S6, and S39 and S40. Solid state memory device 178 may be volatile memory or non-volatile memory. Solid state memory device 178 may comprise a RRAM, EEPROM, RAM, ROM, and the like.

Solid state memory device 178, as described above, may be similar to devices often referred to as a two-wire serial memory chips. In the example of FIG. 15F, solid state memory device 178 comprises four terminals: a power terminal (Term. 1), a ground terminal (Term. 2), a serial read/write terminal (Term. 3), and a serial control terminal (Term. 4). In other examples, more or less terminals may be possible. The power and ground terminals (1 and 2) provide power to solid memory device 178. The serial read/write terminal (3) allows an isolated therapy module, e.g., neuro module 116 (FIG. 7) or cardiac module (FIG. 8), or processor 122 to serially write data into solid state memory device 178, and/or serially read data out of solid state memory device 178. The serial control terminal (4) allows selection between read and write modes.

The power terminal may be selectively coupled to power source 108 via a switch S1 at a first time and may be coupled to the floating power line 130A via a switch S2 at a second time different from the first time. The ground terminal may be selectively coupled to the ground provided by housing 70 via switch S3 at the first time and may be coupled to the floating ground line 130B via switch S4 at the second time. In general, switches S1, S3, S5, and S39 are closed when switches S2, S4, S6 and S40 are open, and vice versa. The states of switches S1, S3, S5, and S39 are switches S2, S4, S6 and S40 may be controlled by respective enable signals that are asserted at different times. In this manner, the memory device 178 may be alternatively powered by ground power and floating power when accessed by processor 122 or a therapy (cardiac or neuro) module, respectively. The read/write terminal may be coupled to processor 122 via switch S5 at the first time and may be coupled to the isolated therapy module via a switch S6 at the second time. In some examples, the read/write terminal may be coupled to a processor of the isolated therapy module via switch S6.

In some examples, a processor of the isolated therapy module or stimulation generator within the isolated therapy module, i.e., a processor that controls therapy parameters and causes the stimulation generator to generate stimulation signals that conform to the therapy parameters, may be carried by or integrated with solid state memory device 178. The control terminal may be coupled to processor 122 via a switch S39 and to the isolated therapy module, a processor within the isolated therapy module, or a processor within a stimulation generator of the isolated therapy module via switch S40. For ease of description, a processor or other control or processing circuitry associated with a therapy module may be referred to as a module processor, which may be different than processor 122.

Enable signals generated at selected times based on respective clock sources (not shown) may provide signals to serially load data in and/or serially load data out of solid state memory device 178. For example, assertion of a first enable signal may cause switches S1, S3, S5 and S39 to close, such that memory device 178 is powered by power source 108 and ground provided by housing 70, and processor 122 is coupled to read and/or write data with respect to the solid state memory device. In this state, processor 122 applies a control signal to control terminal 4 to initiate a read mode by which processor 122 reads data from solid state memory device 178 via serial read/write terminal 3. In this manner, processor 122 may read data from device 178 that was previously written by the therapy module or module processor associated with a therapy module. Processor 122 may also apply a control signal to initiate a write mode in which processor may write data to device 178. Data may be written to and read from different memory locations or the same locations in solid state memory device 178. In some cases, processor 122 may first read and then write, in which case processor 122 may in some cases overwrite data that was already read. Switches S1, S3, S5 and S39 open upon deassertion of the first enable signal.

Assertion of a second enable signal may cause switches S2, S4, S6 and S40 to close, such that memory device 178 is powered by a floating power line and floating ground line, and the therapy module (via a module processor in some cases) is coupled to read and/or write data with respect to the solid state memory device. In this state, the therapy module applies a control signal to control terminal 4 to initiate a read mode by which the therapy module reads data from solid state memory device 178 via serial read/write terminal 3. In this manner, the therapy module may read data from device 178 that was previously written by processor 122. The therapy module may also apply a control signal to initiate a write mode in which the therapy module may write data to device 178. Again, data may be written to and read from different memory locations or the same locations in solid state memory device 178, and may be overwritten in some cases. Switches S2, S4, S6 and S40 open upon deassertion of the second enable signal.

To ensure that switches S2, S4, S6, and S38 are not in a closed state when switches S1, S3, S5, and S39 are in a closed state, the first and second enable signals are asserted at different times. Processor 122 and the therapy module may use different clocks that are not referenced to one another to produce the enable signals at different times, or use isolated versions of the same clock signal to produce the enable signals at different times. A common clock signal may be used to generate enable signals that control switches S1, S3, S5, and S39 and switches S2, S4, S6, and S40, but may cause commonality between the therapy module and processor 122 via the clock source. Accordingly, in examples where IMD 16 includes only one clock source, an additional isolation circuit may be needed. The switches S1, S3, S5, and S39 may be coupled to the clock source and the switches S2, S4, S6, and S40 may be coupled to the clock source via an isolation circuit, or vice versa. A first clock source may be referenced to power source 108 and the ground provided by housing 70, and the second clock source may be referenced to floating power and ground lines. An isolation circuit used to provide isolated clock signals may be provided by any one of isolation circuits 172A-172E (FIGS. 15A-15E).

In other examples, instead of a single clock source, IMD 16 may comprise at least two clock sources (not shown). The two clock sources may be independent of one another, i.e., the two clock sources may not share any common components, and may be unsynchronized with respect to one another. In this sense, the two clock sources may be considered to be asynchronous relative to one another. If different clocks are used in an asynchronous manner relative to one another, the length of the enable signal, i.e., the time between rising and falling edges of the enable signal that triggers read and write operations, may be selected to be substantially smaller than the period of the enable signal so that small errors in the different clocks are less likely to cause the enable signals to overlap with each other over an extended period of time. In this manner, it is possible to prevent processor 122 from reading and writing at the same time the therapy (neuro or cardiac) module is reading and writing with respect to the solid state memory device. In particular, the first enable signal is asserted at a first time when the second enable signal is not asserted, and is deasserted well in advance of assertion of the second enable signal, and vice versa. Although there may be significant length of time between deassertion of one enable signal and assertion of the other enable signal, in some cases, deassertion of one enable signal may be closely followed by, but not overlap with, assertion of the other enable signal.

In some examples, separate clocks may be periodically resynchronized to minimize the risk of overlap of the enable signals generated for the processor 122 and the therapy module. Due to possible changes in frequency as the clock sources age, the frequency of the first clock signal and the frequency of the second clock signal may deviate. Hence, the first and second clock sources may periodically require a resynchronization signal that causes them to output clock signals at substantially the same frequency. In some cases, a resynchronization signal may be provided to the first clock source and a resynchronization signal may be provided to a second clock source via an isolation circuit substantially similar at least one of the isolation circuits described with respect to FIGS. 15A-15E.

The following describes techniques to transmit and receive data between the isolated therapy module and processor 122. For purposes of illustration, the described techniques utilize the example where two asynchronous clocks are provided, although a signal clock source may be used with isolation in some cases. For processor 122 to transmit data, a first enable signal (timed based on a first clock signal) is asserted to close switches S1, S3, S5, and S39. In this example, processor 122 may provide a signal to the control terminal indicating that solid state memory device 178 should be in the read mode. Processor 122 may then read serial data from device 178. For processor 122 to write data, the first clock signal closes switches S1, S3, S5, and S39. In this example, processor 122 may provide a signal to the control terminal indicating that solid state memory device 178 should be in write mode. Processor 122 may then write serial data to device 178. The read and write operations may be performed successively in the same enable period or performed separately in separate enable periods. The order of the read and write operations may be read first, write second or write first, read second. In the manner describe above, the processor 22 can transmit and receive information to and from the therapy module via the isolation interface provided by device 178.

Similarly, for the therapy module, assertion of the second enable signal closes switches S2, S4, S6, and S40. In this example, therapy module may provide a signal to the control terminal indicating that solid state memory device 178 should be in read mode. The therapy module may then read serial data for device 178. For the therapy module to write data, the second enable signal is asserted (or remains asserted) to close switches S2, S4, S6, and S40. In this example, the therapy module may provide a signal to the control terminal indicating that solid state memory device 178 should be in the write mode. The therapy module may then write serial data to device 178. Again, the read and write operations may be performed successively in the same enable period or performed separately in separate enable periods. Also, the order of the read and write operations may be read first, write second or write first, read second. In each case, the therapy module can transmit and receive information to and from processor 122 via the isolation interface provided by device 178.

In the examples described above, switches S1, S3, S5, and S39 are in an open state when the switches S2, S4, S6, and S40 are in a closed state, and vice versa. Accordingly, processor 122 and the isolated therapy module are never coupled to one another. In other words, due to the switches S1, S3, S5, and S39 being open when switches S2, S4, S6, and S40 are closed, and vice versa, as a function of the assertion and deassertion of the respective enable signals, there is no commonality between processor 122 and the isolated therapy module. In these examples, solid state memory device 178 may be considered as flying between processor 122 and the isolated therapy module because solid state memory device 178 receives power from the same power source that provides power to processor 122, e.g., power source 108 in one state, and receives power from the same power source that provides power to isolated therapy module, e.g., floating power and ground lines 130A, 130B (FIG. 7).

In examples where solid state memory device 178 is volatile memory, e.g., RAM, the data stored within solid state memory device 178 may be erased when power is removed. In such examples, a capacitor, e.g., a super capacitor or an ultra capacitor, a rechargeable battery or cell, or a primary battery or cell coupled to a diode may be coupled between the power and ground terminals. For example, when the switches S1 and S3 are closed, power source 108 and the ground provided by housing 70 provide power to solid state memory device 178 and charges the capacitor or the rechargeable battery. When switches S1 and S3 are opened but before the switches S2 and S4 are closed, the capacitor, rechargeable battery, or the primary battery provide power to solid state memory device 178. When switches S2 and S4 are closed, the floating power and ground lines, e.g., floating power and ground lines 130A, 130B provide power to solid state memory device 178 and the charges the capacitor or the rechargeable battery. When the switches S2 and S4 are opened but before switches S1 and S3 are closed, the capacitor, rechargeable battery, or primary battery provide power to solid state memory device 178.

Solid state memory device 178 may reduce or eliminate the commonality between cardiac module 114 and neuro module 116 (FIG. 7). As described above, when switches S1, S3, S5, and S39 are closed, switches S2, S4, S6, and S40 are open. Accordingly, in this state there is no commonality between the therapy module, e.g., neuro module 116 and processor 122. As described above, when switches S2, S4, S6, and S40 are closed, switches S1, S3, S5, and S39 are open. Similarly, in this state there is no commonality between the therapy module, e.g., neuro module 116 and processor 122.

FIG. 15G is a circuit diagram of another example of an isolation circuit 172G. Isolation circuit 172G may, for example, be one or more of isolation circuit 128 (FIGS. 7 and 9) and isolation circuit 140 (FIGS. 8 and 10). As shown in FIG. 15G, isolation circuit 172G comprises a microprocessor 400, a first group of switches 550A, 550B, 550C, S50D (collectively "switch S50"), a second group of switches S51A, S51B, S51C, S51D (collectively "switch S51"), C50, and C51. Isolation circuit 172G, also known as a "flying processor," is a control circuit that may be utilized to convey data in one or both directions across the isolation barrier, perform calculations on data, and operate switches associated with the commutation connection to each side. In some examples, processor 400 is in communication with a memory device (not shown). The memory device may be integral with processor 400, or the memory device may be an external device that is in communication with processor 400.

Processor 400 may be unpowered during times when it is not connected to power on either side, i.e., while in fly. In one example, processor 400 may use a capacitor or a battery (shown generally as voltage source 402 in FIG. 15G) for power during the time that it is not connected to the grounded power. The power for processor 400 while flying may be a capacitor, a primary battery, or a rechargeable battery that also is providing the power that is conveyed to the isolated module. Processor 400 may be used to control the transfer of power and/or data. In addition, processor 400 may control the switches, e.g., switches S50 and S51, to connect/disconnect from the grounded module and from the isolated module. Processor 400 may also process data before transferring it to the other side. For example, processor 400 may compress data, perform algorithms, and translate data formats.

In FIG. 15G, capacitor C50 is a flying storage capacitor that provides both power to processor 400 and power to be transferred to the isolated side, which charges capacitor C51. In some examples, though not shown in FIG. 15G, capacitor C51 may be replaced by a rechargeable battery. In these examples, rather than charging capacitor C51, the rechargeable battery is charged by the power transfer to the isolated side. In operation, switch S50, i.e., S50A, S50B, S50C, and S50D, closes, or is normally closed. Switch S50 may be closed by a control signal from processor 400 via its S50 control line. Then, data is transferred to processor 400. Processor 400 monitors the voltage on C50 via its voltage monitor input. When processor 400 determines that capacitor C50 has reached a sufficient voltage, has stabilized to full voltage, has been dwelling at a target voltage for a target time, or when a command is issued to processor 400 via its "data in" input, processor 400 opens switch S50 and then closes S51, i.e., S51A, S51B, S51C, and S51D. Both data and the energy stored in capacitor C1 are transferred to the isolated module. Processor 400, via its switch S51 control output, opens switch S51 after processor 400 has determined that sufficient energy and data have been transferred to the isolated module, and after processor 400 has received data from the isolated module. This determination may be based on a predetermined time, a voltage level measured across capacitor C1, an acknowledgment that the data transfer is complete, or upon receiving data from the isolated module indicating that it is time for processor 400 to open switch S51. Then, processor 400 closes switch S50 to recharge capacitor C50 and to convey data to the grounded module. The process repeats as needed.

In some examples, processor 400, via its voltage monitor input, monitors the voltage changes on capacitor C50 to determine the voltage on capacitor C51. This may help processor 400 determine whether capacitor C51 needs to charge further, and if so, how much additional charge is needed. Such a determination may ensure that processor 400 is not operating more frequently than needed to keep the power supply sufficient on the isolated side, thereby conserving power.

Processor 400 may be used to transfer power, transfer data, or transfer both power and data. In one example configuration, there may be a first isolation circuit 172G used for power and a second isolation circuit 172G used for data, independent of the first isolation circuit 172G, that run synchronously or asynchronous of each other.

Isolation circuit 172G may be used to convey stimulation signals or to convey input signals via a capacitor using the flying processor to control the switches.

In one example, processor 400 may be used to control only the switches at the isolated side, e.g., switch S51, and the grounded module controls the switch on its side, e.g., switch S50. In such a configuration, processor 400 may monitor switch S50 to detect when switch S50 opens, for example, when voltage on capacitor C50 begins to slowly drop. Then, processor 400 closes switch S51. Switch S51 is only closed for a predetermined amount of time, for example, about 1 millisecond to about 50 milliseconds. Switch S50 is not closed again for a predetermined amount of time to ensure that switch S51 is open prior to switch S50 being closed again.

Processor 400 may be a microprocessor, microcontroller, peripheral interface controller (PIC), field-programmable gate array (FPGA), or any other type of programmable device, as well as an application specific integrated circuit (ASIC), as well as, circuit comprised of discrete components such as FETs, operational amplifiers, comparators, latches, timers, and the like.

Figure 16:
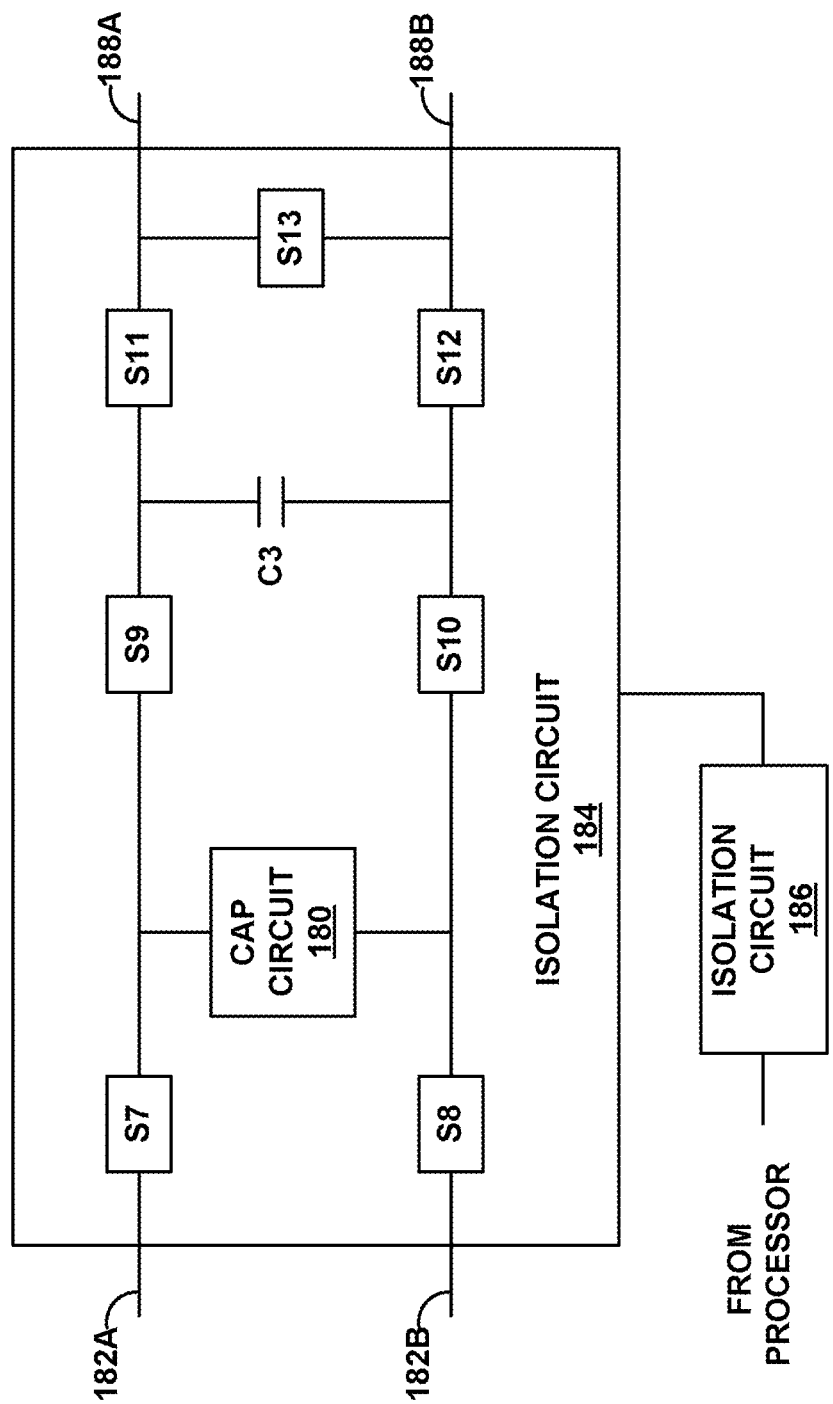
FIG. 16 is a circuit diagram of another example of an isolation circuit.

FIG. 16 is a circuit diagram of another example of an isolation circuit 184. Isolation circuit 184 may, for example, be used to form one or more of isolation circuits 124 (FIG. 7), 126 (FIG. 7), 136 (FIG. 8), 138 (FIG. 8), 152 (FIG. 11), and 156 (FIG. 12). As illustrated in FIG. 16, isolation circuit 184 comprises a flying capacitor that includes a capacitor circuit 180, capacitor C3, and switches S7-S13. Switches S7-S13 may be any type of switches, including microelectromechanical system (MEMS) switches or opto-isolators such as opto-relays, opto-transistors, opto-FETs, and opto-SCRs. Switches S7-S13 may be controlled by processor 122 via isolation circuit 186.

In some examples, each one of switches S7-S13 may comprise a plurality of MEMS switches in series, e.g., 2 to 20 MEMS switches. For example, switch S7 may comprise five MEMS switches in series, switch S6 may comprise five MEMS switches in series, and so on for switches S8-S13. A plurality of MEMS switches in series may provide higher switching voltage capability compared to using only one MEMS switch. Each of the MEMS switches within each of the switches S7-13 may close and open at the same time, or may close and open sequentially. In one example, the plurality of switches in series may be all of the same type of switch. In other examples, the plurality of switches in series may be a combination of types of switches.

In some examples where each one of switches S7-13 comprises a plurality of MEMS switches in series, a resistor may be coupled across each MEMS switch of the plurality of MEMS switches. Each resistor may have a resistance value in a range of approximately 100 kilohms to approximately 100 megaohms, as one non-limiting example. The resistors may assure that when the MEMS switches are open, the voltage at each open MEMS switch is relatively the same for all the MEMS switches within each one of switches S7-S13. Alternatively, the resistors may ensure that the MEMS switches within each one of switches S7-S13 is kept below a breakdown voltage of each MEMS switch. When the MEMS switches are opened in each one of switches S7-S13, the resistors may allow some current to flow through because the resistors are coupled across the MEMS switches. However, due to the large resistance of the resistors, the resistors may limit the amount of current that may flow through.

In some examples where switches S7-S13 include a plurality of MEMS switches in series, in addition to or instead of resistors coupled across the MEMS switches, transient voltage absorbers, voltage triggered current limiters, capacitors, spark gap MEMS devices, or other devices may be coupled across the MEMS switches. The transient voltage absorbers, voltage triggered current limiters, capacitors, or spark gap MEMs devices may protect the MEMS switches from overvoltage breakdown. When activated, the transient voltage absorbers, voltage triggered current limiters, and spark gap MEMs devices may allow some current to flow even though the MEMS switches may be open. However, the transient voltage absorbers, voltage triggered current limiters, and spark gaps MEMS devices may only briefly activate or may provide relatively high impedance, thereby limiting the current that may flow through even though the MEMS switches are open.

In some examples, where switches S7-S13 comprise a plurality of MEMS switches, the MEMS switches may be coupled in a series-parallel configuration to allow higher currents to pass through the MEMS switches when the MEMS switches are closed. Furthermore, as described, switches S7-S13 may comprise MEMS switches in series or in a series-parallel configuration. In some examples, as alternatives, switches S7-S13 may comprise reed relays, field-effect transistors, bipolar junction transistors, or other switching devices. In some examples, each one of switches S7-S13 may comprise a plurality of reed relays, FETs, or other switching devices. In such examples, resistors, transient voltage absorbers, voltage triggered current limiters, capacitors, or spark gaps MEMS devices as described above with respect to MEMS switches may also be coupled across the reed relays, FETs, or other switching devices.

In some examples, switches S7-S13 may be electronic relays. The relays may receive power via an isolation circuit. For example, relays may receive their power from lines 182A and 182B. As described in more detail below, lines 182A and 182B generate an output voltage that is independent of the power source and the ground provided by housing 70. Capacitor circuit 180 may comprise a single capacitor or a plurality of capacitors as described in more detail with reference to FIG. 17.

Switches S7-S13 may be selectively opened and closed in accordance with this disclosure to reduce or eliminate commonality between a first therapy and/or sensing module (e.g., cardiac module 82, 114) of IMD 16 and a second therapy and/or sensing module (e.g., neuro module 84, 116) of IMD 16. Switches S7-S13 may be opened and closed (e.g., toggled) based on a control commands from a processor, such as one of processor 86A, 86B (FIG. 5) or 122 (FIG. 6) in order to reduce or eliminate the commonality. In the example illustrated in FIG. 16, isolation circuit 184 is located between a common power source and one of the first and second sensing/therapy modules. For ease of illustration, isolation circuit 184 will be described in FIG. 16 as being placed between the common power source and the cardiac module. However, isolation circuit 184 may be placed between the common power source and the cardiac module or other therapy and/or sensing module. Moreover, isolation circuit 184 may be placed between different shared or common components of IMD 16 and the first and second modules.

Isolation circuit 184 may receive a supply voltage from the common power source of IMD 16, e.g., power source 96 or power source 108. For example, power line 182A may couple switch S7 of isolation circuit 178 to the common power source and ground line 182B may couple switch S8 of isolation circuit 178 to the common ground, e.g., provided by housing 70. Initially, switches S7, S8, and S13 are closed and switches S9-S12 are opened (e.g., via a control signal from processor 122) for a first state. Closing switches S7 and S8 causes capacitor circuit 174 to charge up and store the charge provided by the common power source. Closing switch S13 squelches any potential noise on floating power line 188A and floating ground line 188B.

In one aspect, after waiting a predetermined amount of time, the processor, e.g., processor 122 or the processor within the therapy module, opens switches S7 and S8, and closes switches S9 and S10. For purposes of illustration, as described below, processor 122 is referenced. However, the processor within the therapy module may be utilized instead of or in addition to processor 122. In another aspect, processor 122 may measure the voltage across capacitor circuit 180 and open switches S7 and S8, and close switches S9 and S10 after the voltage across capacitor circuit 180 reaches a preset (threshold) level for a second state. In either aspect, after switches S7 and S8 are opened, and switches S9 and S10 are closed, capacitor C3 receives the charge stored on capacitor circuit 180.

When switches S9 and S10 are closed, charge transfers from capacitor circuit 180 to capacitor C3 until the voltage across capacitor circuit 180 is the same as the voltage across capacitor C3. Stated another way, the voltage on capacitor circuit 180 decreases and the voltage on capacitor C3 increases until the voltage on capacitor C3 is the same as the voltage on capacitor circuit 180. During this charge transfer or after the transfer is complete, processor 122 may measure the voltage across capacitor C3 to determine whether the voltage has reached a desired level. If the voltage across capacitor C3 is not at the desired level, processor 122 opens switches S9 and S10, closes switches S7 and S8, and keeps switches S11 and S12 open. Capacitor circuit 180 receives charge from the common power source and the voltage on capacitor circuit 180 increases. After either a predetermined amount of time, or after processor 122 determines that the voltage across capacitor circuit 180 has reached a threshold or desired level, processor 122 opens switches S7 and S8 and closes switches S9 and S10. Capacitor C3 receives the voltage from capacitor circuit 180. The voltage on capacitor circuit 180 then decreases and the voltage on capacitor C3, increases and once again, processor 122 determines whether the voltage across capacitor C3 has reached the desired level. If the voltage across capacitor C3 has not reached the desired level, the steps just described are repeated until the voltage across capacitor C3 reaches the desired level.

As one non-limiting example that illustrates how capacitor C3 may be charged, assume switches S7 and S8 are closed and switches S9 and S10 are opened. Capacitor circuit 180 may receive charge from the power source and the voltage on capacitor circuit 180 may increase to 8 V. Next, switches S7 and S8 may be opened and switches S9 and S10 may be closed. Capacitor circuit 180 may discharge to capacitor C3 until the voltage on capacitor circuit 180 and capacitor C3 is the same. Assume that after capacitor circuit 180 discharges to capacitor C3, the voltage on capacitor circuit 180 is 4 V and the voltage on capacitor C3 is 4V. Next, processor 122 may determine that the voltage of 4 V on capacitor C3 is insufficient. Processor 122 may then open switches S9 and S10, and close switches S7 and S8.

Capacitor circuit 180 may currently be at 4 V, but after switches S7 and S8 close, capacitor circuit 180 may be charged back up to 8 V because switches S7 and S8 couple capacitor circuit 180 to the power source. Next, processor 122 may open switches S7 and S8, and close switches S9 and S10. Since capacitor circuit 180 is at 8 V and capacitor C3 is at 4 V, capacitor circuit 180 may discharge to capacitor C3 until the voltage on capacitor circuit 180 is the same as the voltage on capacitor C3. In this example, the voltage on capacitor circuit 180 may decrease to 6 V, and the voltage on capacitor C3 may increase to 6 V. Processor 122 may then determine that 6 V on capacitor C3 is sufficient.

After capacitor C3 has reached the desired level, processor 122 opens switches S9, S10, and S13, and closes switches S11 and S12 for a third state. Capacitor C3 then discharges its charge to floating power line 188A and floating ground line 188B. In this manner, capacitor C3 functions as the power source and ground for the therapy and/or sensing module coupled to isolation circuit 184 via floating power line 188A and floating ground 188B. Since the voltage across capacitor C3 is no longer referenced to the common power source and the common ground provided by housing 70, e.g., due to switches S9 and S10 being open, the charge that is discharged from capacitor C3 is referred to as "floating." In other words, the signal ground of capacitor C3 is not connected to the can ground (housing 70 in the example described above). As such, floating power line 188A and floating ground line 188B are not referenced to the common power source and the common ground provided by housing 70. In this manner, isolation circuit 184 reduces or eliminates the commonality between the cardiac module and the neuro module of IMD 16. It should be noted that in some examples, a dedicated circuit may be used to control the switches rather than a processor, e.g., processor 122.

Floating power line 188A and floating ground line 188B may be substantially equivalent to floating power line 130A and floating ground line 130B (FIG. 7), floating power line 134A and floating ground line 134B (FIG. 7), floating power line 142A and floating ground line 142B (FIG. 8), floating power line 146A and floating ground line 146B (FIG. 8), floating power line 154A and floating ground line 154B (FIG. 11), and floating power line 158A and floating ground line 158B (FIG. 12).

After processor 122 opens switches S9, S10, and S13, and closes switches S11 and S12, processor 122 may close switches S7 and S8 to recharge capacitor circuit 180. Processor 122 may continually measure the voltage across capacitor C3. The voltage across capacitor C3 may slowly be reduced as capacitor C3 discharges its charge. After the voltage across capacitor C3 drops below a preset level, processor 122 may open switches S7 and S8, close switches S9 and S10, and keep switches S11 and S12 closed. Capacitor circuit 180 will then recharge capacitor C3 while also providing voltage across floating power line 188A and floating ground line 188B. After capacitor C3 is recharged to a preset level, processor 122 may open switches S9 and S10 and close switches S7 and S8. These steps may be repeated every time the voltage across capacitor C3 drops below a preset level.

In this manner, isolation circuit 184 receives voltage from the common power source, and is capable of providing constant direct current (DC) voltage across floating power line 188A and floating ground line 188B. To reiterate, the voltage across floating power line 188A and floating ground line 188B is not referenced to the common power source and the common ground provided by housing 70. Accordingly, with reference to FIG. 7, where isolation circuit 128 is equivalent to isolation circuit 184, the voltage received by stimulation generator 120B shares no commonality with the voltage received by stimulation generator 120A, and sensing module 118A shares no commonality with the neuro module 116. As described above, by reducing or eliminating the commonality, the common-mode interference and the shunt current may be reduced or eliminated.

In some aspects, the signal provided by the processor may also require an isolation circuit so as to reduce or eliminate commonality. For example, in aspects where the cardiac module and the neuro module share a common processor, the common processor may provide control signals to isolation circuit 184 via another isolation circuit 186. However, in aspects where the cardiac module and the neuro module do not share a processor, no isolation circuit is necessary if the processor needs to provide a control signal to isolation circuit 184.

Isolation circuit 186 may be substantially similar to isolation circuit 172A through isolation circuit 172F (FIGS. 15A-15F). However, isolation circuit 186 is providing signals from the processor to isolation circuit 184 and not from the processor to a therapy module as described in FIGS. 15A-15F.

Figure 17:
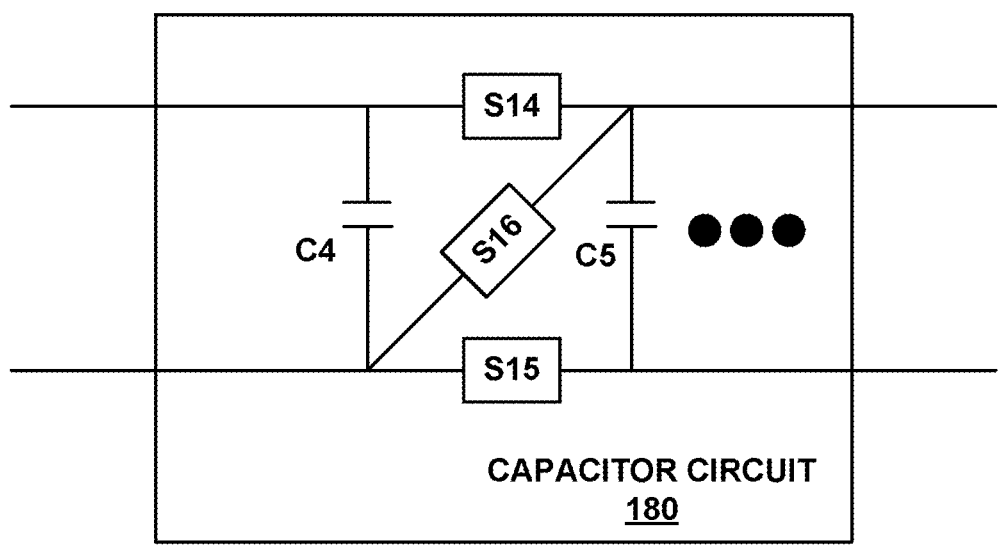
FIG. 17 is an example circuit diagram of a capacitor circuit.

FIG. 17 is an example circuit diagram of capacitor circuit 180. As shown in FIG. 17, capacitor circuit 180 includes capacitors C4 and C5, and switches S14-S16. Although illustrated in FIG. 17 as including two capacitors, capacitor circuit 180 may include more than two capacitors, which may boost the voltage provided by the common power source. Alternatively, in some instances, capacitor circuit 180 may comprise a single capacitor.

Initially, e.g., when switches S7 and S8 of isolation circuit 184 are closed, and switches S9-S10 are open (FIG. 16), processor 122 may provide a signal to close switches S14 and S15, and open switch S16. Accordingly, the common voltage source charges capacitors C4 and C5 in parallel.

After processor 122 opens switches S7 and S8 of isolation circuit 184 and closes switches S9 and S10 of isolation circuit 184, processor 122 may open switches S14 and S15, and close switch S16. It should be noted that the switches on the isolated side cannot be connected directly to processor 122 because processor 122 is referenced to ground. Accordingly, capacitors C4 and C5 are discharged in series providing a boost to the voltage stored on capacitors C4 and C5. Discharging capacitors C4 and C5 in series provides a higher voltage stored on capacitor C3 (FIG. 16). In some aspects, capacitor circuit 180 may comprise additional capacitors and switches configured in the same manner as shown in FIG. 17 coupled together in series. This may allow capacitor circuit 180 to provide additional voltage to capacitor C3.

FIG. 18A is a circuit diagram of another example isolation circuit 200. Isolation circuit 200 comprises a transformer circuit that includes an oscillator 194, transformer 196, rectifier 198, and capacitor C6. Transformer 196 may be any type of transformer such as but not limited to a piezoelectric transformer. Isolation circuit 200 may, for example, serve as one or more of isolation circuit 148 (FIG. 9), 150 (FIG. 10), 164 (FIG. 12).

Like isolation circuit 184 of FIG. 16, isolation circuit 200 operates as described below to reduce or eliminate the commonality caused by a first therapy and/or sensing module (e.g., cardiac module 82, 114) and a second therapy and/or sensing module (e.g., neuro module 84, 116) sharing a common power source. Isolation circuit 200 may be located between the common power source and one of the first and second sensing/therapy modules. Although described in the context of a shared power source, isolation circuit 200 may be placed between a different shared or common component of IMD 16 and the first and second modules to reduce or eliminate the commonality.

Isolation circuit 200 receives voltage from the common power source of IMD 16, e.g., power source 96 or power source 108. For example, power line 192A may couple a power input (or positive input) of oscillator 194 to a positive voltage of the common power source and ground line 192B may couple a ground (or negative) input of oscillator 194 to the ground provided by housing 70. Oscillator 194 receives the voltage provide by the common power source and generates an oscillating output based on a control signal provided by a processor, such as one of processors 86A (FIG. 5), 86B (FIG. 5), or 122 (FIG. 6).

Transformer 196 receives the oscillating output of oscillator 194. The output of oscillator 194 is referenced to the common power source and ground provided by housing 70. Transformer 196 transfers electrical energy from received from oscillator 194 between a first circuit to a second circuit through inductively coupled electrical conductors. In particular, the AC current from oscillator 194 is fed to the first circuit (the transformer primary) and creates a changing magnetic field. In turn, this magnetic field induces a changing voltage in the second circuit (the transformer secondary). Transformer 196 may be a transformer with a 1:1 ratio, e.g., such that the input and output voltage of the transformer are the same. However, in some aspects, transformer 196 may provide step up or step down in the input voltage e.g. transformer 196 may have 1:2 or 1:3 ratio. In a 1:2 ratio transformer, for example, the voltage may be stepped up by a factor of two. One example of transformer 196 may include, for example, an isolation transformer. Transformer 196 may provide any ratio between the input and output of transformer 196. For example, transformer 196 may provide a 1:1 ratio, or a 1:2 ratio, etc. Transformer 196 may have a dielectric isolation between input and output of, for example, 20 volts to 9000 volts AC. The output of transformer 196 is no longer referenced to power source 96 or 108. Consequently, there is no commonality between the output of transformer 196 and the input of transformer 196.

Rectifier 198 receives and rectifies the output of transformer 196. Rectifier 198 may be a full-wave rectifier or a half-wave rectifier. Capacitor C6 receives the output of rectifier 198. Capacitor C6 smoothes the output of rectifier 198 to provide a constant DC voltage output. As described above, transformer 196 decouples the input of the transformer from the output of the transformer. As such, the output of rectifier 198 is also not referenced to the common power source or the ground provided by housing 70. In this manner, isolation circuit 200 receives voltage from a common power source and is capable of providing an uncoupled, constant direct current (DC) voltage across floating power line 202A and floating ground line 202B. To reiterate, the voltage across floating power line 202A and floating ground line 202B is not referenced to common power supply or the ground provided by housing 70. Therefore, there is no commonality between the cardiac module and the neuro module through the common power supply or ground, thus reducing or eliminating the common-mode interference or the shunt current.

In some examples, the oscillator signal utilized for power transfer may also serve as a data line. In addition, an oscillator on the isolated side can drive a transformer, either transformer 196 or another transformer, which conveys data across to the grounded side. Examples where the oscillator signal may also serve as a data line is shown in more detail with respect to FIG. 18B.

Similar to FIG. 16, in some aspects, the signal provided by processor 122 to isolation circuit 200 and, in particular, oscillator 194, may require an isolation circuit. Accordingly, in aspects that require isolation, the control signal is isolated via isolation circuit 190, which may be substantially similar to isolation circuit 186 (FIG. 16). The control signal may be provided to control the oscillation frequency and/or other aspects of the signal produced by oscillator 194.

FIG. 18B is a circuit diagram of another example isolation circuit 200. FIG. 18B may be substantially similar to FIG. 18A but may include data demodulator 199. In some examples, transformer 196 of FIG. 18A may also be used to send data from the processor, e.g., processor 122, to a therapy module, e.g., neuro module 116 or cardiac module 114 (FIG. 7). For example, in examples where isolation circuit 128 comprises a transformer (as shown in FIG. 15C), isolation circuit 128 and isolation circuit 126 (FIG. 7) may be merged into a single isolation circuit with data input 192C and power inputs 192A, 192B and data output 202C from data demodulator 199 and power outputs 202A, 202B, as shown in FIG. 18B.

As shown in FIG. 18B, oscillator 194 may be controlled by data input signal 192C which is provided by processor 122, in one example. Oscillator 194 is connected to the power source through input line 192A and ground through input line 192B. The control signal on data input 192C may modulate amplitude, frequency, phase, or pulse width of oscillator 194 to enable transmission of amplitude modulated, frequency modulated, phase modulate, or pulse width modulated data signals from processor 122 through transformer 196.

Similar to FIG. 18A, rectifier 198 receives and rectifies the output of transformer 196. Rectifier 198 may be a full-wave rectifier or a half-wave rectifier. Capacitor C6 receives the output of rectifier 198. Capacitor C6 smoothes the output of rectifier 198 to provide a constant DC voltage output. As described above, transformer 196 decouples the input of the transformer from the output of the transformer. As such, the output of rectifier 198 is also not referenced to the common power source or the ground provided by housing 70. In this manner, isolation circuit 200 receives voltage from a common power source and is capable of providing an uncoupled, constant direct current (DC) voltage across floating power line 202A and floating ground line 202B.

Data demodulator 199 recovers amplitude modulate, frequency modulated, phase modulated, or pulse width modulated data signals from the output of transformer 196. The output of demodulator 199 is provided on data output line 202C. Data output line 202C may be coupled to one of neuro module 114 or cardiac module 116. In this manner, one way data transmission is provided through a transformer that also provides power that is floating relative to the voltage source and common ground.

One way data transmission should be considered as non-limiting. There may be other schemes to enable transmission of power and bi-directional (two way) data through a single transformer. One such technique is disclosed in U.S. Pat. No. 7,139,613 by James Reinke and Robert Ecker and assigned to Medtronic, Inc. Medtronic, Inc. is also the assignee of this application. The entire content of U.S. Pat. No. 7,139,613 is incorporated herein by reference. U.S. Pat. No. 7,139,613 discloses at least one example of how power and bi-directional data pulses can be transmitted between two modules across a pair of wires. The techniques of the U.S. Pat. No. 7,139,613 may be used in conjunction with a transformer to provide isolated power transfer and data communications between modules.

FIG. 19 is a circuit diagram of another example of isolation circuit 212. Isolation circuit 212 is a barrier circuit that includes an oscillator 206, resistors R3 and R4, capacitors C7, C8, and C9, and rectifier 210. In one aspect, isolation circuit 212 may serve as one or more of isolation circuit 124 (FIG. 7), 126 (FIG. 7), 136 (FIG. 8), 138 (FIG. 8), 152 (FIG. 11), and 156 (FIG. 12)

Like isolation circuits 184 and 200 of FIGS. 16 and 18, respectively, isolation circuit 212 operates as described below to reduce or eliminate the commonality caused by a first therapy and/or sensing module (e.g., cardiac module 82, 114) and a second therapy and/or sensing module (e.g., neuro module 84, 116) sharing a common power source. Isolation circuit 212 may be located between the common power source and one of the first and second sensing/therapy modules. Although described in the context of a shared power source, isolation circuit 212 may be placed between a different shared or common component of IMD 16 and the first and second modules to reduce or eliminate the commonality.

Isolation circuit 212 receives voltage from the common power source of IMD 16, e.g., power source 96 or power source 108. For example, power line 204A may couple a power input (or positive input) of oscillator 206 to a positive voltage of the common power supply and ground line 204B may couple a ground (or negative) input of oscillator 206 to the ground provided by housing 70. Oscillator 206 receives the voltage provided by the common power source and generates an oscillating output based on a control signal provided by a processor, such as one of processors 86A (FIG. 5), 86B (FIG. 5), or 122 (FIG. 6). The control signal may be provided to oscillator 206 via an isolation circuit, such as isolation circuit 213 shown in FIG. 19. The control signal may be provided to control the oscillation frequency and/or other aspects of the signal produced by oscillator 206.

The oscillating output generated by oscillator 206 may be one of any number of different shapes, for example, a pulse, a sine wave, or other types of waveforms. The oscillating output may also be continuous, duty cycled, or provided on an as-needed basis to conserve battery power, including an on-demand approach.

In some examples, the output of oscillator 206 may be filtered. For example, capacitors C7 and C8 may be used to couple the energy from oscillator 206 to rectifier 210. In other examples, resistors R3 and R4 may be included to provide additional filtering. The output of oscillator 206 is referenced to power source 96 or 108 and the ground provided by housing 70. Capacitors C7 and C8 are coupling capacitors that remove the DC component of the output of oscillator 206. At low frequencies, coupling capacitors C7 and C8 behave as open circuit connections, not allowing significant DC current to flow through them. With AC coupling, the outputs of capacitor C7 and C8 are no longer referenced to power source 96 or 108 and the ground provided by housing 70.

It should be noted that oscillator 206 may have a unipolar output, which has a DC component, or oscillator 206 may have an AC output with no appreciable DC component. Even if oscillator 206 has no DC component, the capacitors may provide isolation of circuits.

In addition, output parameters such as frequency, modulation, duty cycle, voltage, for example, of oscillator 206 may be controlled such that the output conveys data as well as power. The data may be measured on the isolated side. In some examples, the data may be measured prior to rectifier 210, or may be measured subsequent to rectifier 210. Measuring the data prior to rectifier 210 may be preferred to measuring the data after rectifier 210.

Rectifier 210 receives and rectifies the output of capacitors C7 and C8. Capacitor C9 receives the output of rectifier 210. Capacitor C9 smoothes the output of rectifier 210 to provide a constant DC voltage output. As described above, resistors R3 and R4 and capacitors C7 and C8 decouple the output of oscillator 206 from the input to rectifier 210. As such, the output of rectifier 210 is also not referenced to common power source or the ground provided by housing 70. In this manner, isolation circuit 212 receives voltage from common power source and is capable of providing an uncoupled, constant direct current (DC) voltage across floating power line 214A and floating ground line 216B. To reiterate, the voltage across floating power line 214A and floating ground line 216B is not referenced to common power supply or the ground provided by housing 70. Therefore, there is no commonality between the cardiac module and the neuro module through the common power supply or ground, thus reducing or eliminating the common-mode interference or the shunt current.

In some examples, isolation circuit 212 may further include a voltage multiplier (not shown). The voltage multiplier may provide voltage gain to generate a higher voltage across floating power line 214A and floating ground line 214B. In one example, the voltage multiplier may be coupled to the output of oscillator 206, but before resistor R3. In another example, the voltage multiplier may be coupled to the output of rectifier 210. Also, in some aspects, the control signal provided by processor 122 may require an isolation circuit. Accordingly, in aspects that require isolation, the control signal is isolated via isolation circuit 213, which may be substantially similar to isolation circuit 186 (FIG. 16) and isolation circuit 190 (FIG. 18A and FIG. 18B).

FIG. 20 is a circuit diagram of another example of an isolation circuit 216. Isolation circuit 216 comprises LED 218 and a photo-voltaic cell 220. In one aspect, isolation circuit 216 may be used as one or more of isolation circuit 124 (FIG. 7), 126 (FIG. 7), 136 (FIG. 8), 138 (FIG. 8), 152 (FIG. 11), and 156 (FIG. 12)

Like isolation circuits 184, 200, 212 of FIGS. 16, 18, and 19 respectively, isolation circuit 216 operates as described below to reduce or eliminate the commonality caused by a first therapy and/or sensing module (e.g., cardiac module 82, 114) and a second therapy and/or sensing module (e.g., neuro module 84, 116) sharing a common power source. Isolation circuit 216 may be located between the common power source and one of the first and second sensing/therapy modules. Although described in the context of a shared power source, isolation circuit 216 may be placed between a different shared or common component of IMD 16 and the first and second modules to reduce or eliminate the commonality.

LED 218 receives voltage from the common power source of IMD 16, e.g., power source 96 or power source 108. For example, power line 222A may couple a positive input of LED 218 to a positive voltage of the common power supply and ground line 222B may couple a ground (or negative) of LED 218 to the ground provided by housing 70. The connection to the power source and ground may cause LED 218 to illuminate. Photo-voltaic cell 220 may sense the illumination of LED 218 and in response generate a voltage and current. There may not be any direct connection between the common power source, e.g., voltage source 98 or 108 and the output of photo-voltaic cell 220. The voltage generated by photo-voltaic cell 220 may not share any commonality with the common power source, e.g., power source 96 or 108 and the ground provided by housing 70.

In this manner, isolation circuit 216 receives voltage from common power source and is capable of providing an uncoupled, constant direct current (DC) voltage across floating power line 224A and floating ground line 224B. To reiterate, the voltage across floating power line 224A and floating ground line 224B is not referenced to common power supply or the ground provided by housing 70, i.e., is not referenced to power line 222A and ground line 222B. Therefore, there is substantially no commonality between the cardiac module and the neuro module through the common power supply or ground, thus reducing or eliminating the common-mode interference or the shunt current.

In some examples, LED output parameters such as frequency, modulation, duty cycle, and brilliance, for example, may be controlled such that the output conveys data as well as power. The data may be measured on the isolated side.

FIG. 21 is a circuit diagram of another example of an isolation circuit 216. Isolation circuit 236 comprises a flying capacitor circuit. Isolation circuit 236 may, for example, be used as one or more of isolation circuit 148 (FIG. 9), 150 (FIG. 10), 164 (FIG. 13), and 170 (FIG. 14).

Isolation circuit 236 may comprise a plurality of sub-isolation circuits. For example, as shown in FIG. 21, isolation circuit 236 comprises sub-isolation circuit 234A and 234B, collectively referred to as sub-isolation circuits 234. Although only two sub-isolation circuits are shown in FIG. 21, in different aspects, there may be more or fewer sub-isolation circuits 234. The number of sub-isolation circuits that may be needed may be based on the number of electrode pairs coupled to cardiac module 114 or cardiac module 82 and neuro module 116 or neuro module 84. For example, as shown in FIG. 9, isolation circuit 148 provides stimulation to two electrode pairs, e.g., one electrode pair comprising electrodes 104A and 104B and another electrode pair comprising electrodes 106A and 106B. In particular, sub-isolation circuits 234A and 234B may provide stimulation to electrode pairs 104 and 106, respectively. However, if there are more electrode pairs in addition to electrode pairs 104 and 106, isolation circuit 236 may comprise additional sub-isolation circuits 234 to provide stimulation to the additional electrode pairs. In other words, each of the sub-isolation circuits 234 illustrated in FIG. 21 is capable of providing stimulation to a single electrode pair.

As shown in FIG. 21, sub-isolation circuit 234A comprises input lines 226A and 226B. Input lines 226A and 226B may be coupled to various components. For example, with respect to FIG. 9, isolation circuit 148 of FIG. 9 may be used to form isolation circuit 236 as shown in FIG. 21. In this example, input lines 226A and 226B may be coupled to power source 108 and the ground provided by housing 70, respectively. As another example, with respect to FIG. 13, isolation circuit 164 of FIG. 13 may be used to form isolation circuit 236 as shown in FIG. 21. In this example, input lines 226A and 226B may be coupled to the first two outputs of neuro module 162.

Sub-isolation circuit 234B is coupled to input lines 230A and 230B. Similar to input lines 226A and 226B, input lines 230A and 230B may be coupled to various components. For example, with respect to FIG. 9, isolation circuit 148 of FIG. 9 may serve as isolation circuit 236 as shown in FIG. 21. In this example, input lines 230A and 230B may be coupled to power source 108 and the ground provided by housing 70. As another example, with respect to FIG. 13, isolation circuit 162 of FIG. 13 may be isolation circuit 236 as shown in FIG. 21. In this example, input lines 230A and 230B may be coupled to a second set of outputs of neuro module 162, where input lines 226A and 226B of sub-isolation circuit 234A are coupled to the first two outputs of neuro module 162. Output lines 228A and 228B may be coupled to electrodes, e.g., electrodes 104A and 104B of FIG. 9 or electrodes 104A and 104B of FIG. 13. Output lines 232A and 232B may be coupled to electrodes, e.g., electrodes 106A and 106B of FIG. 9 or electrodes 106A and 106B of FIG. 13.

Isolation circuit 236 may receive control commands from a processor, such as one of processor 86A, 86B (FIG. 5) or processor 122 (FIG. 6) to provide the stimulation signal to one or more electrodes. For purposes of illustration, processor 122 is referenced below. In some aspects, the control signal provided by processor 122 may require an isolation circuit, e.g., with processor 122 provides commonality between two therapy or sensing modules. Accordingly, in aspects that require isolation, the control signal may be isolated via isolation circuit 237, which may be substantially similar to isolation circuit 186 (FIG. 16), isolation circuit 190 (FIG. 18A and FIG. 18B), and isolation circuit 213 (FIG. 19).

Sub-isolation circuits 234 comprise a plurality of switches. For example, sub-isolation circuit 234A comprises switches S17-S23 and isolation circuit 234B comprises switches S24-S30. Switches S17-S30 may be MEMS switches, opto-isolators (e.g., opto-relays, opto-transistors, opto-FETs, and opto-SCRs) or any other type of switch. Sub-isolation circuit 234A and 234B may further comprise capacitors C10 and C11, respectively.

As described above, processor 122 executes a therapy program that provides a stimulation signal on electrodes. The therapy program may specify the pulse width, frequency, and amplitude of the stimulation signal. When the therapy program specifies that the stimulation therapy is a single electrical pulse, processor 122 may provide a control signal to close switches S17, S18, and S21, and open switches S19, S20, S22, and S23. In this switch configuration, capacitor C10 receives charge from the power source and stores the charge. Toggling close switch S21 may squelch any output noise. After a predetermined amount of time or when the voltage across capacitor C10 reaches a desired level, which may correspond to a desired stimulation signal amplitude, processor 122 opens switches S17, S18, and S21, closes switches S19 and S20, and keeps switches S22 and S23 open. In this switch configuration, the voltage stored on capacitor C10 discharges to provide the stimulation signal to electrodes coupled to output lines 228A and 228B.

As another example, to provide a stimulation signal to electrodes via output lines 228A and 228B, processor 122 may provide a control signal to close switches S17, S18, and S21, and open switches S19, S20, S22, and S23. As described above, such a switch configuration causes capacitor C10 to receive charge from the power source and stores the charge. Toggling switch S21 to a closed state squelches any output noise. After a predetermined amount of time or when the voltage across capacitor C10 reaches a desired level, processor 122 opens switches S17, S18, and S21. After capacitor C10 is charged by the power source for the predetermined amount of time or to the desired voltage level, processor 122 may open and close switches S19 and S20 at the frequency and pulse width specified by the therapy program to deliver a plurality of electrical pulses. For example, if the therapy program specified a pulse width of 1 milliseconds and a frequency of 120 Hz, switches S19 and S20 may be opened and closed for 1 milliseconds every 8 milliseconds (1/120). In this manner, the stimulation signal provided to the electrodes coupled to output lines 228A and 228B matches the therapy parameters set by the therapy program.

In some examples, it may be desirable to change (reverse) the polarity of the electrodes coupled to output lines 228A and 228B. To reverse the polarity of the electrodes, processor 122 may close switches S22 and S23, instead of toggling closed switches S19 and S20. In this manner, the electrode that was the positive electrode is now the negative electrode and the electrode that was the negative electrode is now the positive electrode.

Sub-isolation circuit 234B may provide the stimulation signal to electrodes coupled to output lines 232A and 232B in a similar way as described above with respect to sub-isolation circuit 234A. In particular, processor 122 may close switches S24, S25, and S26, and open switches S26 and S27 to charge capacitor C11. After capacitor C11 reaches a desired level or after a predetermined amount of time, processor 122 opens switches S24, S25, and S28, and closes switches S26 and S27 to deliver the electrical stimulation via output lines 232A and 232B. To provide stimulation signals in accordance with the therapy program parameters, processor 122 may, in some instances, open and close switches S26 and S27 at the frequency and pulse width defined by the therapy program.

The voltage across input lines 226A and 226B is referenced to power source 108 and the ground provided by housing 70. Similarly, the voltage across input lines 230A and 230B is referenced to power source 108 and the ground provided by housing 70. The voltage across output lines 228A and 228B is not referenced to power source 108 and the ground provided by housing 70. Instead, the voltage across output lines 228A and 228B is referenced to one another. Similarly, the voltage across output lines 232A and 232B is not referenced to power source 108 and the ground provided by housing 70.

In this manner, isolation circuit 236 receives voltage from power source 108, and is capable of providing stimulation signals that are not referenced to power source 108. To reiterate, the voltage across output lines 228A, 228B, 232A, and 232B is not referenced to power source 108 and the ground provided by housing 70. Accordingly, as one example, assume isolation circuit 148 (FIG. 9) is substantially equivalent to isolation circuit 236, e.g., replace isolation circuit 148 with isolation circuit 216. The stimulation signal provided to electrodes 104A, 104B, 106A, and 106B shares no commonality with the signals sensed by sensing module 118A. As described above, by reducing or eliminating the commonality, the common-mode interference and the shunt current may be reduced or eliminated.

Because the voltage across output lines 228A, 228B, 232A, and 232B is not referenced to power source 108 or the ground provided by housing 70 a stimulation generated by output lines 228A, 228B, 232A, and 232B may not impose a common voltage as common-mode interference. For example, with respect to FIGS. 9 and 13, where isolation circuit 148 and 164 are equivalent to isolation circuit 236. Stimulation generated by neuro module 116 or 162, respectively, may not impose a common voltage as common-mode interference because isolation circuit 148 and 164 reduce or eliminate the commonality between the stimulation generated by neuro module 116 and 162 and the ground provided by housing 70. Similarly, with respect to FIGS. 10 and 14, where isolation circuit 150 and 170 are equivalent to isolation circuit 236. A stimulation generated by cardiac module 114 and 160 may not impose a common voltage as common-mode interference because isolation circuit 150 and 170 reduce or eliminate the commonality between the stimulation generated by cardiac module 114 and 160 and the ground provided by housing 70.

The shunt current may be reduced or eliminated because at least some of the switches with isolation circuit 236 will be open at all times. For example, with respect to FIG. 13, during normal operation, switches S17, S18, S24, and S25 may be open at all times except when neuro module 162 needs to sense the signals on electrodes 104A, 104B, 106A, and 106B to, for example, perform impedance measurements or provide stimulation. Since switches S17, S18, S24, and S25 may be open most of time, the stimulation generated by cardiac module 160 cannot feed into neuro module 162 because there is no path for the shunt current to flow. Stated another way, when switches S17, S17, S24, and S25 are open, they create a high impedance path for the shunt current.

Furthermore in some examples, cardiac module 160 may provide a signal to neuro module 162 every time cardiac module 160 is about to provide a stimulation signal. For example, in instances where neuro module 162 and cardiac module 160 do not share a common processor, e.g., neuro module 84 and cardiac module 82 (FIG. 5), cardiac module 160 may transmit a signal via its telemetry interface to neuro module 162 indicating that cardiac module 160 is about to provide a stimulation signal. In response, neuro module 162 may insure that switches S17, S18, S24, and S25 are opened so that no shunt current may feed into neuro module 162. As another example, in instances where neuro module 162 and cardiac module 160 share a common processor, e.g., neuro module 116 and cardiac module 114 (FIG. 6), cardiac module 160 may transmit a signal via the shared processor to neuro module 162 indicating that cardiac module 160 is about to provide a stimulation signal. In response, neuro module 162 may ensure that switches S17, S18, S24, and S25 are opened so that no shunt current may feed into neuro module 162.

Also, to reiterate, with respect to FIG. 10, FIG. 13, and FIG. 14, isolation circuit 150, 164, and 170 may be substantially equivalent to isolation circuit 236. For example, with respect to FIG. 13, input lines 226A and 226B may be coupled to the first two outputs of neuro module 162. Input lines 230A and 230B may be coupled to the second two outputs of neuro module 162. Output lines 228A and 228B may be coupled to electrodes 104A and 104B, respectively, and output lines 232A and 232B may be coupled to electrodes 106A and 106B, respectively.

With respect to FIG. 13, neuro module 116 may sense a signal, e.g., an impedance measurement, in a substantially similar manner as neuro module 116 may generate stimulation via isolation circuit 216. For example, with respect to FIG. 13, lines 228A and 228B may be coupled to electrodes 104A and 104B, respectively. Lines 232A and 232B may be coupled to electrodes 106A and 106B, respectively. In such instances, the processor, which may be processor 96 or 122, and referred to as just the processor, may close switches S19, S20, S26, and S27, and open switches S17, S18, S21, S22, S23, S24, S25, S28, S29, and S30. The signal sensed by electrodes 104A and 104B may be stored as a charge across capacitor C10. The signal sensed by electrodes 106A and 106B may be stored as a charge across capacitor C11. Subsequently, the processor may open switches S19, S20, S26, and S27, and close switches S17, S18, S24, and S25. The signal sensed by electrodes 104A, 104B, 106A, and 106B and stored across capacitor C10 and C11 may then be discharged to the sensing module within neuro module 162.

FIG. 22 is a circuit diagram of another example of an isolation circuit 252. Isolation circuit 252 comprises a transformer circuit. In one aspect, one or more of isolation circuit 148 (FIG. 9) and 150 (FIG. 10) may be substantially similar to isolation circuit 252. For example, in the example IMD 16 of FIGS. 9 and 10, isolation circuit 148 and 150 may be substantially similar to isolation circuit 252.

Isolation circuit 252 comprises a plurality of sub-isolation circuits. For example, as shown in FIG. 22, isolation circuit 252 comprises sub-isolation circuit 246A and 246B, collectively referred to as sub-isolation circuits 246. Although only two sub-isolation circuits are shown in FIG. 22, in different aspects, there may be more or fewer sub-isolation circuits 246. The number of sub-isolation circuits that may be needed is based on the number of electrode pairs coupled to cardiac module 114 or cardiac module 82 and neuro module 116 or neuro module 84. For example, as shown in FIG. 9, isolation circuit 148 provides stimulation to two electrode pairs, e.g. one electrode pair is 104A and 104B, another electrode pair is 106A and 106B. In examples where isolation circuit 148 is equivalent to isolation circuit 252, isolation circuit 252 may comprise two sub-isolation circuits to provide stimulation to electrodes 104A, 104B, 106A, and 106B. However, if there are more electrodes pairs other than 104A, 104B, 106A, and 106B, isolation circuit 252 may comprise additional sub-isolation circuits 246 to provide stimulation to the additional electrode pairs.

As shown in FIG. 22, sub-isolation circuit 246A comprises input lines 242A and 242B. Input lines 242A and 242B may be coupled to various components. For example, with respect to FIG. 9, input lines 242A and 242B may be coupled to power source 108 and the ground provided by housing 70.

Sub-isolation circuit 246B comprises input lines 248A and 248B. Similar to input lines 242A and 242B, input lines 248A and 248B may be coupled to various components. For example, with respect to FIG. 9, input lines 248A and 248B may be coupled to power source 108 and the ground provided by housing 70.

Isolation circuit 252 receives control commands from one of processor 86A, 86B (FIG. 5) or processor 122 (FIG. 6) referred to as just the processor for the description of FIG. 22. Similar to FIGS. 16-20, in some aspects, the control signal provided by the processor may require an isolation circuit. Accordingly, in aspects that require isolation, the control signal is isolated via isolation circuit 253 which is equivalent to isolation circuit 186 of FIG. 16, isolation circuit 190 of FIG. 18A and FIG. 18B, isolation circuit 213 of FIG. 19, and isolation circuit 237 of FIG. 21.

Each one of sub-isolation circuits 246 comprises a plurality of switches, a transformer, and an oscillator. For example, sub-isolation circuit 246A comprises oscillator 238A, and sub-isolation circuit 246B comprises oscillator 238B. As shown in FIG. 22, sub-isolation circuit 246A comprises switches S31 and S32, and isolation circuit 246B comprises switches S33 and S34. Switches S31-S34 may be MEMS switches or opto-isolators such as opto-relays, opto-transistors, opto-FETs, opto-SCRs, field-effect transistors, bipolar junction transistors, as well as other suitable semiconductors.

Sub-isolation circuit 246A further comprises transformer 240A, and sub-isolation circuit 246B further comprises transformer 240B. Transformer 240A and 240B may each be a 1:1 transformer. In some aspects transformer 240A and 240B may comprise any possible ratio. Examples of transformer 240A and transformer 240B include, for example, an isolation transformer or an auto-transformer where the transformer primary and transformer secondary do not share a common connection. Transformers 240 may provide any ratio between the input and output of transformers 240. For example, transformer 240A may provide a 1:1 ratio, or a 1:2 ratio, etc. Transformers 240 may have a dielectric isolation between input and output of, for example, 20 volts to 9000 volts AC. Furthermore, in some examples, the wiring to transformers 240 may be reversed to provide an opposite polarity stimulation signal. In some examples, transformer 240A and 240B may be 3-tap transformers. The center tap of the 3-tap transformers may be coupled to the ground provided by housing 70. Transformers 240 may also reduce shunt currents because transformers 240 may reduce the amount of stimulation that is intercepted by the electrodes. For example, transformers 240 may make neuro module 116 act like an independent stimulator source away from cardiac module 114. Transformers 240 may also provide a low impedance to drive the electrodes coupled to 244A, 244B, 250A, and 250B. Transformers 240 may provide impedance conversion from the primary to the secondary whereby the secondary has a lower impedance which is coupled to electrodes 244A, 244B, 250A, and 250B. In this manner, transformers 240 may enable more effective driving of electrodes 244A, 244B, 250A, and 250B.

With respect to FIG. 9 where isolation circuit 148 is equivalent to isolation circuit 252, input lines 242A and 248A may be coupled to power source 108, and input lines 242B and 242B may be coupled to the ground provided by housing 70. Input lines 242A and 242B may provide power to oscillator 238A, and input lines 248A and 248B may provide power to oscillator 238B. Output lines 244A and 244B may be coupled to electrodes 104A and 104B, respectively. Output lines 250A and 250B may be coupled to electrodes 106A and 106B, respectively.

As described above, processor 122 executes a therapy program that provides a stimulation signal on electrodes. The therapy program may specify the pulse width, frequency, and amplitude of the stimulation signal. With respect to FIGS. 9 and 10, to provide the stimulation signal in accordance with the therapy program, processor 122 may cause oscillator 238A and 238B to generate a pulse comprising an amplitude set by the therapy program. Oscillators 238A and 238B may be powered by the common power source and referenced to the ground provided by housing 70. Switches S31-S35 may be open in most instances except for when the therapy module, e.g., neuro module 116 (FIG. 9) or cardiac module 114 (FIG. 10), desires to provide a stimulation signal. Prior to when the therapy module desires provides a stimulation signal, processor 122 may close switches S31-S35.

The pulse generated by oscillators 238A and 238B may then be provided to transformers 240A and 240B. Transformers 240A and 240B receive the pulse output of oscillators 238A and 238B. The output of oscillators 238A and 238B is referenced to the common power source and ground provided by housing 70. Transformers 240A and 240B inductively transfer electrical energy received from oscillators 238A and 238B to output lines 244A, 244B and 250A, 250B. Transformers 240A and 240B may remove any direct connection between oscillators 238A and 238B and output lines 244A, 244B and 250A, 250B. The output of transformers 240A and 240B is no longer referenced to power source 96 or 108. Stated another way, there is no commonality between the output of transformers 240A and 240B and the input of transformers 240A and 240B. As described above, by reducing or eliminating the commonality, the common-mode interference and/or the shunt current may be reduced or eliminated.

In some examples, to reduce power consumption by oscillators 238A and 238B, oscillators 238A and 238B may be powered down at all times except for prior to and while the therapy module transmits a stimulation. Processor 122 may provide a signal that turns on oscillators 238A and 238B when processor 122 closes switches S31-S35. In other words, processor 122 toggles on oscillators 238A and 238B when processor 122 closes switches S31-S35. Processor 122 toggles off oscillators 238A and 238B when processor 122 opens switches S31-S35.

FIG. 23 is a circuit diagram of another example of an isolation circuit 266. Isolation circuit 266 comprises a transformer circuit. In one aspect, one or more of isolation circuit 164 (FIG. 13) and 170 (FIG. 14) may be substantially similar to isolation circuit 266. For example, in the example IMD 16 of FIGS. 13 and 14, isolation circuit 164 and 170 may be substantially similar to isolation circuit 266.

Isolation circuit 266 comprises a plurality of sub-isolation circuits. For example, as shown in FIG. 23, isolation circuit 266 comprises sub-isolation circuit 262A and 262B, collectively referred to as sub-isolation circuits 262. Though only two sub-isolation circuits are shown in FIG. 23, in different aspects there may be more or fewer sub-isolation circuits 262. The number of sub-isolation circuits that may be needed is based on the number of electrode pairs coupled to cardiac module 114 or cardiac module 82 and neuro module 116 or neuro module 84. For example, as shown in FIG. 13, isolation circuit 164 provides stimulation to two electrode pairs, e.g. one electrode pair is 104A and 104B, another electrode pair is 106A and 106B. In examples where isolation circuit 164 is equivalent to isolation circuit 266, isolation circuit 266 may comprise two sub-isolation circuits 262 to provide stimulation to electrodes 104A, 104B, 106A, and 106B. However, if there are more electrodes pairs other than 104A, 104B, 106A, and 106B, isolation circuit 266 may comprise additional sub-isolation circuits 262 to provide stimulation to the additional electrode pairs.

As shown in FIG. 23, sub-isolation circuit 262A comprises input lines 256A and 256B. Input lines 256A and 256B may be coupled to various components. For example, with respect to FIG. 13, input lines 256A and 256B may be coupled to the first two outputs of neuro module 162. Sub-isolation circuit 262B comprises input lines 260A and 260B. Similar to input lines 256A and 256B, input lines 260A and 260B may be coupled to various components. For example, with respect to FIG. 13, input lines 260A and 260B may be coupled to the last two outputs of neuro module 162, where input lines 256A and 256B of sub-isolation circuit 262A are coupled to the first two outputs of neuro module 162.

Isolation circuit 266 receives control commands from one of processor 86A, 86B (FIG. 5) or processor 122 (FIG. 6) referred to as just the processor for the description of FIG. 23. Similar to FIGS. 16-20, in some aspects, the control signal provided by the processor may require an isolation circuit. Accordingly, in aspects that require isolation, the control signal is isolated via isolation circuit 267 which is equivalent to isolation circuit 186 of FIG. 16, isolation circuit 190 of FIG. 18A and FIG. 18B, isolation circuit 213 of FIG. 19, isolation circuit 237 of FIG. 21, and isolation circuit 253 (FIG. 22).

Each one of sub-isolation circuits 262 comprises a plurality of switches and a transformer. For example, sub-isolation circuit 262A comprises switches S35 and S36, and isolation circuit 262B comprises switches S37 and S38. Switches S35-S38 may be MEMS switches or opto-isolators such as opto-relays, opto-transistors, opto-FETs, and opto-SCRs.

Sub-isolation circuit 262A further comprises transformer 254A, and sub-isolation circuit 262B further comprises transformer 254B. Transformers 254A and 254B may be substantially similar to transformers 240A and 240B (FIG. 22).

As described above, processor 122 executes a therapy program that provides a stimulation signal on electrodes. The therapy program may specify the pulse width, frequency, and amplitude of the stimulation signal. With respect to FIGS. 13 and 14, sub-isolation circuits 262 may receive the amplitude for the stimulation from cardiac module 160 and neuro module 162. For example, with respect to FIG. 13, input lines 256A and 256B may be coupled to the first two outputs of neuro module 162 and input lines 260A and 260B may be coupled to the last two outputs of neuro module 162. In some examples, the voltage and/or current levels on lines 256A, 256B or lines 260A, 260B may be used to control the respective amplitudes of the stimulation signals applied via transformers 254A, 254B.

Processor 122 may toggle switches S35-S38 in accordance with the frequency and pulse width parameters. For example, assume the therapy program specifies that the frequency is 100 Hz and the pulse width is 1 milliseconds for the stimulation provided by electrodes 104A and 104B. The therapy program specifies that the frequency is 50 Hz and the pulse width is 3 milliseconds for the stimulation provided by electrodes 106A and 106B. Accordingly, processor 122 may close switches S35 and S36 for 1 milliseconds every 10 milliseconds (1/100). Processor 122 may open switches S35 and S36 the remainder of the time. Similarly, processor 122 may close switches S37 and S38 for 3 milliseconds every 20 milliseconds (1/50). Processor 122 may open switches S37 and S38 the remainder of the time.

The voltages received by transformers 254 are referenced to power source 108 and the ground provided by housing 70. However, the outputs of transformers 254 are not referenced to power source and the ground provided by housing 70. Instead, the outputs of transformers 254 are referenced to one another. Accordingly, the stimulation signal provided to electrodes 104A, 104B, 106A, and 106B shares no commonality with the signals sensed by cardiac module 160 (FIG. 13). As described above, by reducing or eliminating the commonality, the common-mode interference and the shunt current may be reduced or eliminated. Furthermore, transformers 254 provide an additional benefit of allowing, for example, cardiac module 160 to output a stimulation signal with a polarity that is different than the polarity of the stimulation generated by, for example, neuro module 162.

With respect to FIG. 13, neuro module 162 may sense a signal, e.g. an impedance measurement, in a substantially similar manner as neuro module 162 may generate stimulation via isolation circuit 266. For example, with respect to FIG. 13, lines 258A and 258B may be coupled to electrodes 104A and 104B, respectively. Lines 260A and 260B may be coupled to electrodes 106A and 106B, respectively. In such instances, the processor, which may be processor 96 or 122, and referred to as just the processor, may close switches S35-S38. The signal sensed by electrodes 104A and 104B may be transferred across transformer 254A. The signal sensed by electrodes 106A and 106B may be transferred across transformer 254B. Subsequently, the processor may open switches S35-S38.

With respect to FIG. 13, during normal operation, switches S35-S38 may be open at all times except when neuro module 162 needs to sense the signals on electrodes 104A, 104B, 106A, and 106B to, for example, perform impedance measurements. Since switches S35-S38 may be open most of time, the stimulation generated by cardiac module 160 cannot feed into neuro module 162 because there is no path for the shunt current to flow. Hence, when switches S35-S38 are open, they create a high impedance path for the shunt current.

Furthermore in some examples, cardiac module 160 may provide a signal to neuro module 162 every time cardiac module 160 is about to provide a stimulation signal. For example, in instances where neuro module 162 and cardiac module 160 do not share a common processor, e.g., neuro module 84 and cardiac module 82 (FIG. 5), cardiac module 160 may transmit a signal via its telemetry interface to neuro module 162 indicating that cardiac module 160 is about to provide a stimulation signal. In response, neuro module 162 may insure that switches S35-S38 are open so that no shunt current may feed into neuro module 162. As another example, in instances where neuro module 162 and cardiac module 160 share a common processor, e.g., neuro module 116 and cardiac module 114 (FIG. 6), cardiac module 160 may transmit a signal via the shared processor to neuro module 162 indicating that cardiac module 160 is about to provide a stimulation signal. In response, neuro module 162 may insure that switches S35-S38 are open so that no shunt current may feed into neuro module 162.

Figure 24:
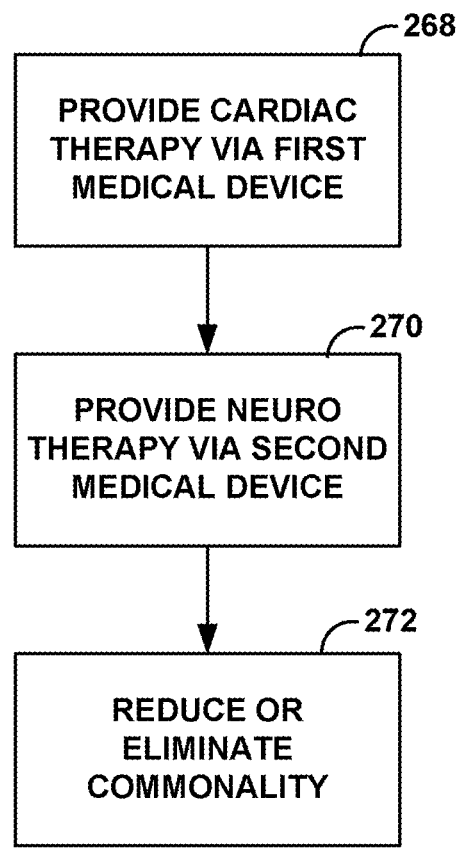
FIG. 24 is a flow diagram illustrating an example technique of reducing or eliminating commonality.

FIG. 24 is a flow diagram illustrating an example technique of reducing or eliminating commonality. A first medical device provides cardiac therapy to patient 12 (268). Examples of the first medical device include cardiac module 82 (FIGS. 5, 11, and 12), cardiac module 114 (FIGS. 6-10), and cardiac module 160 (FIGS. 13 and 14). A second medical device provides cardiac therapy to patient 12 (270). Examples of the second medical device include neuro module 84 (FIGS. 5, 11, and 12), neuro module (FIGS. 6-10), and neuro module 162 (FIGS. 13 and 14). At least one or more isolation circuits are provided that reduce or eliminate the commonality between the first medical device and the second medical device (272). The isolation circuits may be coupled to at least one of a power input to the first medical device, a power input to the second medical device, a stimulation output of the first medical device, a stimulation output of the second medical device, a sensing input of the first medical device, and a sensing input of the second medical device. Examples of the isolation circuits are described with respect to FIGS. 16 and 18-23. The various locations of the isolation circuits are described with respect to FIGS. 7-14.

Figure 25:
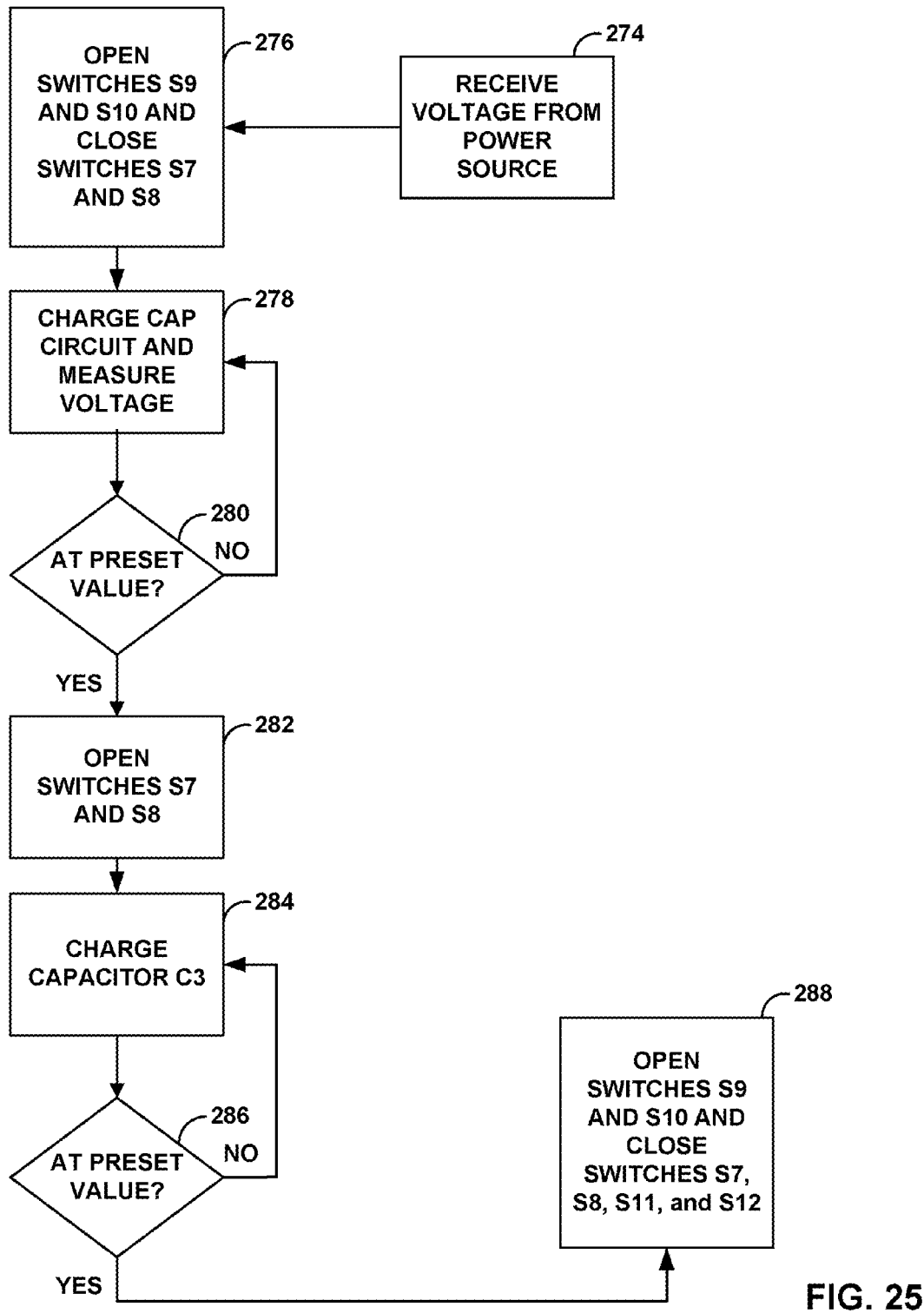
FIG. 25 is a flow diagram illustrating an example technique of reducing or eliminating commonality at the power input of a medical device.

FIG. 25 is a flow diagram illustrating a first example technique of reducing or eliminating commonality at the power input of a medical device. The flow diagram of FIG. 25 may be applicable for isolation circuit 124 (FIGS. 7 and 9), isolation circuit 126 (FIG. 7), isolation circuit 136 (FIGS. 8 and 10), isolation circuit 140 (FIG. 8), isolation circuit 152 (FIG. 11), and isolation circuit (FIG. 12). For purposes of clarity, reference will be made to FIG. 16. Also, processor 122 will be referenced solely for purposes of illustration. A flying-capacitor circuit receives voltage from a power source (274). The processor opens switches S9 and S10 and closes switches S7 and S8 for a first state (276). The closing of switches S7 and S8 causes capacitor circuit 180 to charge and store the voltage received from the power source (278). Processor 122 measures the voltage across capacitor circuit 180. Processor 122 next determines whether the voltage across capacitor circuit 180 is at a preset value (280). If the voltage across capacitor circuit 180 is not at the preset value (NO of 280), capacitor circuit 180 keeps charging and storing the voltage received from the power source (278). If the voltage across capacitor circuit 180 is at the preset value (YES of 280), processor 122 opens switches S7, and S8 for a second state (282), which cause capacitor C3 to be charged (284). Next, processor 122 determines whether the voltage across capacitor C3 is at the preset value (286). If the voltage across capacitor C3 is not at the preset value (NO of 286), capacitor C3 keeps charging and storing the voltage received from capacitor circuit 180 (284). If the voltage across capacitor C3 is at the preset value (YES of 286), processor 122 opens switches S9 and S10, and closes switches S7, S8, S11, and S12 for a third state (288). Capacitor C3 provides a constant DC voltage to either a cardiac module or a neuro module.

Figure 26:
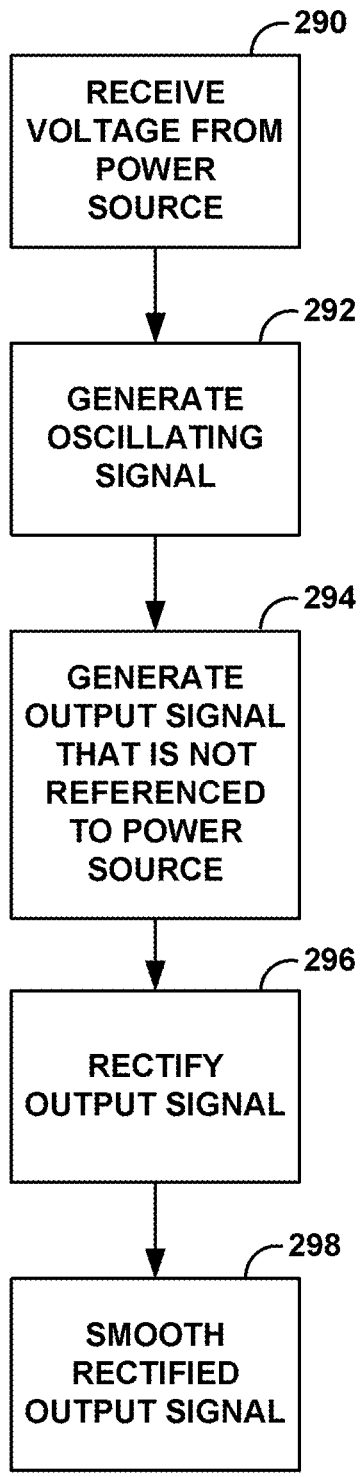
FIG. 26 is a flow diagram illustrating another example technique of reducing or eliminating commonality at the power input of a medical device.

FIG. 26 is a flow diagram illustrating another example technique of reducing or eliminating commonality at the power input of a medical device. The flow chart of FIG. 26 may be applicable for isolation circuit 124 (FIGS. 7 and 9), isolation circuit 126 (FIG. 7), isolation circuit 136 (FIGS. 8 and 10), isolation circuit 140 (FIG. 8), isolation circuit 152 (FIG. 11), and isolation circuit (FIG. 12). For purposes of clarity, reference will be made to FIGS. 18A and 19. A transformer circuit (FIG. 18A) or a barrier circuit (FIG. 19) receives voltage from a power source (290). Oscillator 194 or oscillator 206 generates an oscillating output based on control signal provided by processor 122 (292). With respect to FIG. 18A, transformer 196 generates an output that is not referenced to the power source (294). With respect to FIG. 19, coupling capacitors C7 and C8 generate an output that is not referenced to the power source (294). Rectifier 198 or rectifier 210 rectifies the output that is not referenced to the power source (296). Capacitor C5 or C9 smoothes the output of the rectifier to generate a constant DC voltage (298).

Figure 27:
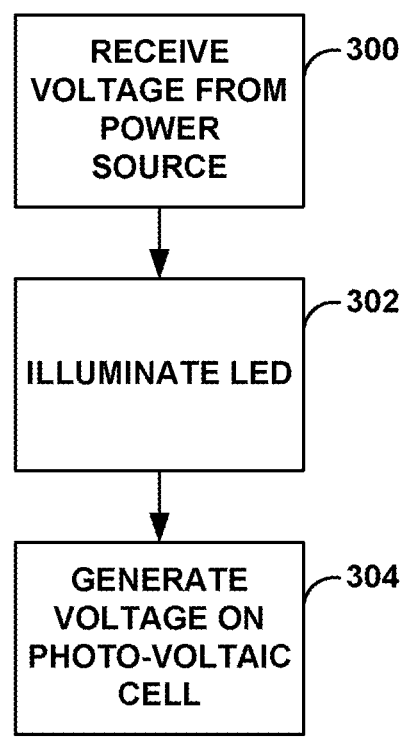
FIG. 27 is a flow diagram illustrating another example technique of reducing or eliminating commonality at the power input of a medical device.

FIG. 27 is a flow diagram illustrating another example technique of reducing or eliminating commonality at the power input of a medical device. The flow chart of FIG. 27 may be applicable for isolation circuit 124 (FIGS. 7 and 9), isolation circuit 126 (FIG. 7), isolation circuit 136 (FIGS. 8 and 10), isolation circuit 140 (FIG. 8), isolation circuit 152 (FIG. 11), and isolation circuit (FIG. 12). For purposes of clarity, reference will be made to FIG. 20. LED 218 receives voltage from power source (300). LED 218 illuminates in response to the voltage (302). The illumination of LED 218 causes a voltage to be generated by photo-voltaic cell 220 (304). The voltage generated by photo-voltaic cell 220 provides a constant DC voltage to either a cardiac module or a neuro module.

Figure 28:
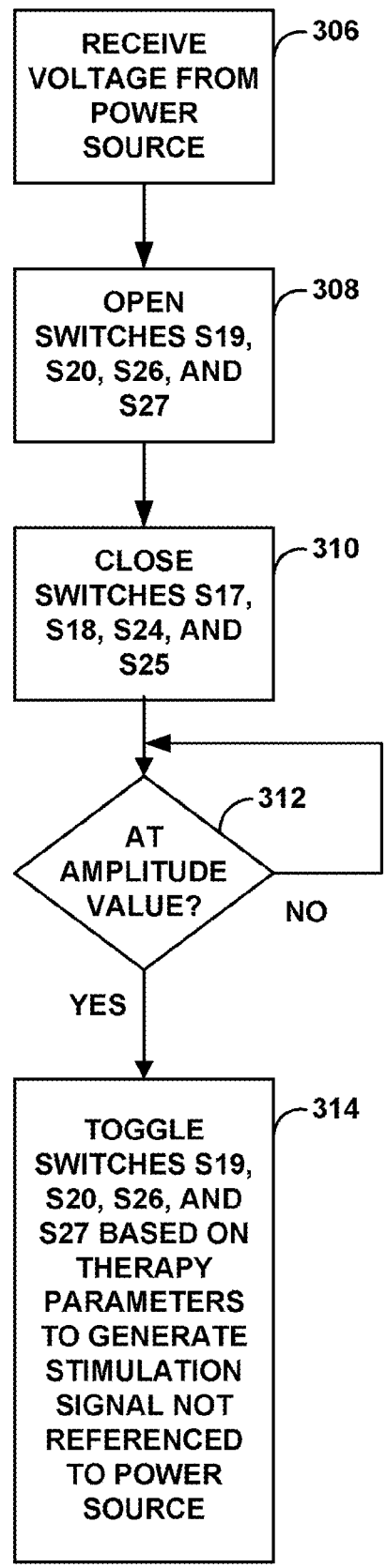
FIG. 28 is a flow diagram illustrating an example technique of reducing or eliminating commonality at the stimulation output of a medical device.

FIG. 28 is a flow diagram illustrating a first example technique of reducing or eliminating commonality at the stimulation output of a medical device. The flow chart of FIG. 28 may be applicable for isolation circuit 148 (FIG. 9), isolation circuit 150 (FIG. 10), isolation circuit 164 (FIG. 13), and isolation circuit 170 (FIG. 14). For purposes of clarity, reference will be made to FIG. 21. Input lines 226A, 226B, 230A, and 230B receive a voltage or signal (306). For example, isolation circuit 148 and isolation circuit 150 receive a voltage from power source 108, while isolation circuit 164 and isolation circuit 170 receive a signal from neuro module 162 or cardiac module 160. Processor 122 opens switches S19, S20, S26, and S27 (308). Processor 122 closes switches S17, S18, S24, and S25 (310). Processor 122 determines whether the voltage across capacitors C10 and C11 are equal to the amplitude level set by the therapy program (312). If the voltage level across capacitors C10 and C11 is less than the amplitude level set by the therapy program (NO of 312), capacitors C10 and C11 keep being charged by the voltage across input lines 226A, 226B, 230A, and 230B. If the voltage level across capacitors C10 and C11 is equal to the amplitude level set by the therapy program (YES of 312), processor 122 closes switches S19, S20, S26, and S27 and opens S17, S18, S24, and S25 based on the frequency and pulse width parameters set by the therapy program (314).

Figure 29:
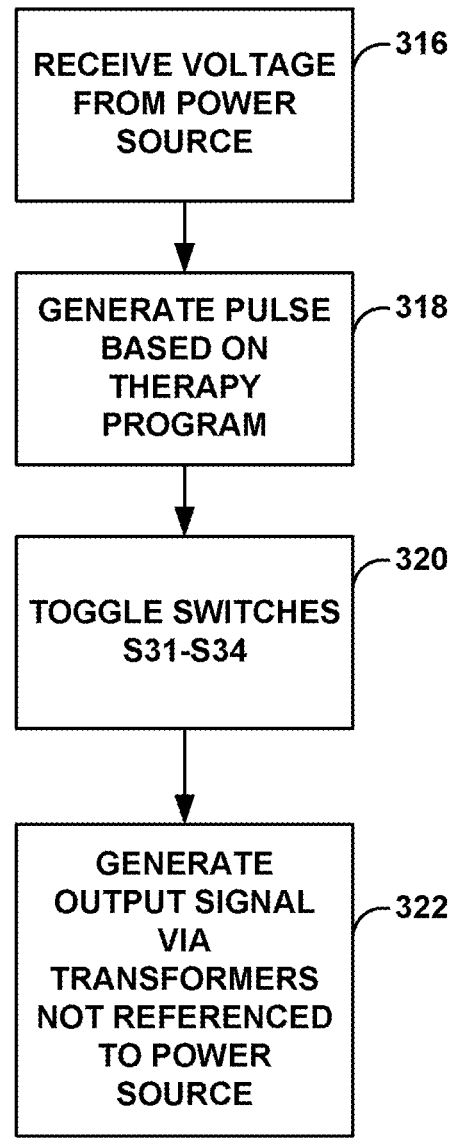
FIG. 29 is a flow diagram illustrating another example technique of reducing or eliminating commonality at the stimulation output of a medical device.

FIG. 29 is a flow diagram illustrating another example technique of reducing or eliminating commonality at the stimulation output of a medical device. The flow chart of FIG. 29 may be applicable for isolation circuit 148 (FIG. 9) and isolation circuit 150 (FIG. 10). For purposes of clarity, reference will be made to FIG. 22. Oscillator 238A and oscillator 238B receive power from power source 108 via input lines 242A, 242B, 248A, and 248B (316). Oscillators 238A and 238B generate a pulse based on the therapy parameter of the therapy program (318). Prior to when the therapy module, e.g., cardiac module 114 or neuro module 116, outputs a stimulation signal, processor 122 toggles switches S31-S34 (320). Transformer 240A and 240B receive the signal from oscillators 238A and 238B and generate a stimulation signal that is not referenced the power source by inductively coupling to a conductor (322). In some examples to reduce power consumption, processor 122 may toggle off oscillators 238A and 238B when processor 122 closes switches S31-S35. Processor 122 may toggle on oscillators 238A and 238B when processor 122 opens switches S31-S35.

Figure 30:
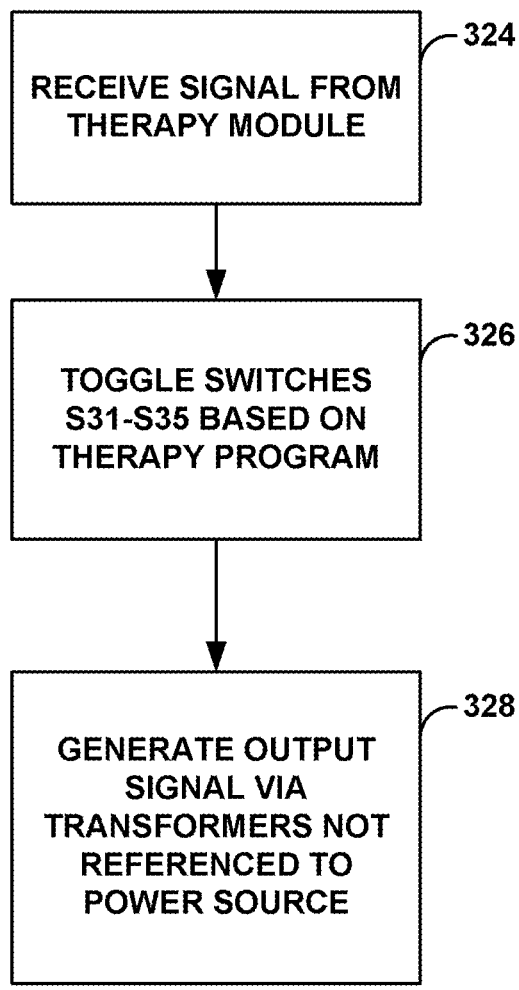
FIG. 30 is a flow diagram illustrating another example technique of reducing or eliminating commonality at the stimulation output of a medical device.

FIG. 30 is a flow diagram illustrating another example technique of reducing or eliminating commonality at the stimulation output of a medical device. The flow chart of FIG. 30 may be applicable for isolation circuit 164 (FIG. 13) and isolation circuit 170 (FIG. 13). For purposes of clarity, reference will be made to FIG. 23. Sub-isolation circuits 262A and 262B within isolation circuit 266 may receive a signal from a therapy module via input lines 256A, 256B, 260A, and 260B (324). The signal may be generated by neuro module 162 (FIG. 13) or cardiac module 160 (FIG. 14). Processor 122 may toggle switches S35-S38 based on the therapy parameters of the therapy program to generate the stimulation signal in accordance with the therapy program (326). Transformer 254A and 254B receive the signal via switches S35-S38 and generate a stimulation signal that is not referenced the power source by inductively coupling to a conductor (328).

Figure 31:
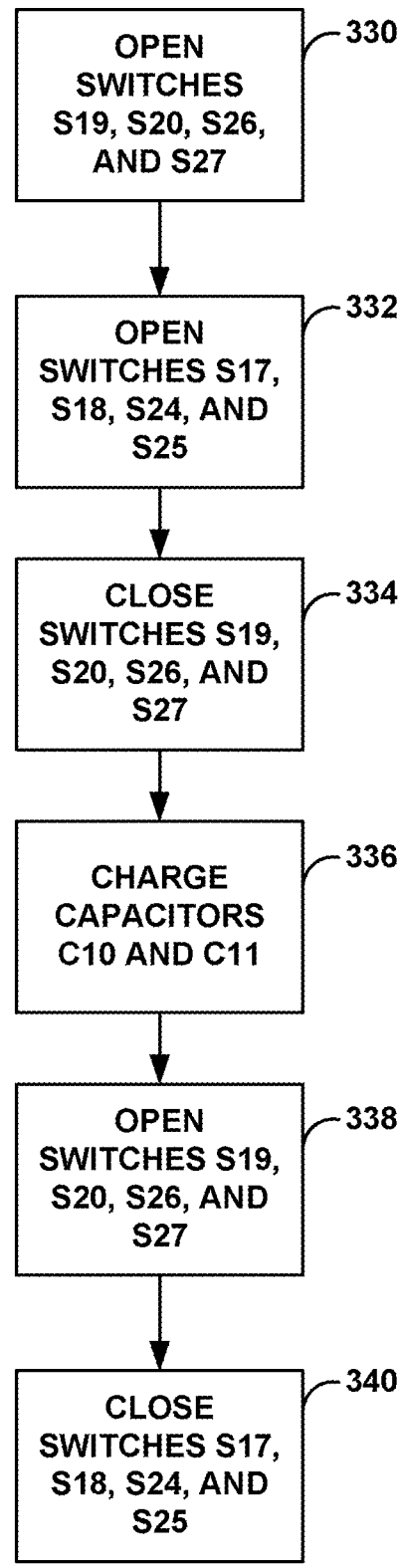
FIG. 31 is a flow diagram illustrating an example technique of reducing or eliminating commonality at the sensing input of a medical device.

FIG. 31 is a flow diagram illustrating a first example technique of reducing or eliminating commonality at the sensing input of a medical device. For purposes of clarity, reference will be made to FIG. 21. Lines 228A, 228B, 232A, and 232B couple to sensing electrodes. Lines 226A, 226B, 230A, and 230B couple to the sensing module within the therapy module. Processor 122 opens switches S19, S20, S26, and S27 (330). When processor 122, for example, measures the impedance, processor 122 opens switches S17, S18, S24, and S25 (332). Processor 122 then closes switches S19, S20, S26, and S27 (334). Capacitors C10 and C11 are charged by the signal that is being sensed, e.g., the signal on electrodes 104A, 104B, 106A, and 106B (336). Processor 122 then opens switches S19, S20, S26, and S27 (338). Processor 122 then closes switches S17, S18, S24, and S25 to discharge the sensed signal to sensing module within the therapy module (340).

Figure 32:
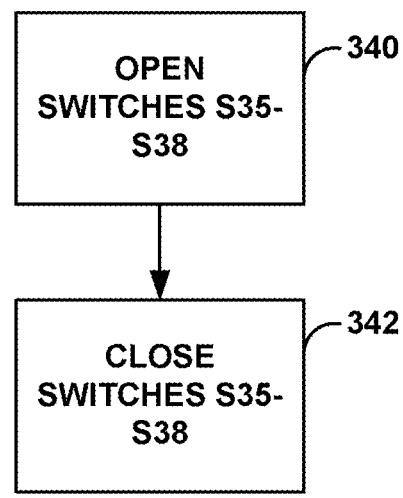
FIG. 32 is a flow diagram illustrating another example technique of reducing or eliminating commonality at the sensing input of a medical device.

FIG. 32 is a flow diagram illustrating another example technique of reducing or eliminating commonality at the sensing input of a medical device. For purposes of clarity, reference will be made to FIG. 23. Processor 122 opens switches S35-S38 (342). When processor 122 for example, measures the impedance, processor 122 closes switches S35-S38 (344).

FIG. 33 is a functional block diagram of another example configuration of IMD 16. IMD 16 shown in FIG. 33 may be substantially similar to IMD 16 shown in FIG. 6. In addition to the components shown in FIG. 6, IMD 16 shown in FIG. 33 includes isolation circuit 408, switch S54, and power device 406. As shown in FIG. 33, neuro module 116 includes processor 404.

Switch S54 may also be considered an isolation circuit. Switch S54 may be any type of switches, including microelectromechanical system (MEMS) switches or opto-isolators such as opto-relays, opto-transistors, opto-FETs, and opto-SCRs.

Also, though power device 406 is shown external to neuro module 116, in some examples, neuro module 116 may include power device 406. Power device 406 may be any component or device that can store and provide power to neuro module 116. Examples of power device 406 include a capacitor, e.g., a ceramic or electrolytic capacitor having a value of about 0.1 microfarads to about 100 microfarads, a super capacitor, an ultra capacitor, or a rechargeable battery or cell. Power device 406 may be charged by power source 108.

Processor 404 may include any one or more of a microprocessor, a controller, a digital signal processor (DSP), an application specific integrated circuit (ASIC), a field-programmable gate array (FPGA), or equivalent discrete or integrated logic circuitry. In some examples, processor 404 may include multiple components, such as any combination of one or more microprocessors, one or more controllers, one or more DSPs, one or more ASICs, or one or more FPGAs, as well as other discrete or integrated logic circuitry. The functions attributed to processor 404 herein may be embodied as software, firmware, hardware or any combination thereof.

As shown in FIG. 33, isolation circuit 408 includes switches S52 and S53. Switches S52 and S54 may be any type of switches, including microelectromechanical system (MEMS) switches or opto-isolators such as opto-relays, opto-transistors, opto-FETs, and opto-SCRs. Processor 404 may control switches S52 and S53. Switches S52 and S53 may generally be closed. Similarly, processor 404 may control switch S54 which may generally be closed. When switches S52, S52, and S53 are closed, there is commonality between neuro module 116 and cardiac module 114.

In operation, when cardiac module 114 is about to transmit a stimulation signal, cardiac module 114 may convey a signal to processor 404 via processor 122 that cardiac module 114 is about to transmit a stimulation signal. In response, processor 404 may open switches S52, S53, and S54. After switches S52 and S53 are open, neuro module 116 may be powered by power device 406. Notably, after switches S52, S53, and S54 are open, there is no commonality between neuro module 116 and cardiac module 114.

In the example of FIG. 33, isolation circuit 408 may provide intermittent isolation between cardiac module 114 and neuro module 116. In other words, there may be commonality between cardiac module 114 and neuro module 116 during some modes of operation. However, during some other modes of operation, particularly when cardiac module is about to transmit a stimulation signal, the commonality between cardiac module 114 and neuro module 116 is reduced or eliminated.

In the example of FIG. 33, little to no shunt current may flow from cardiac module 114 into neuro module 116 because there is no complete current path for the shunt current to flow from cardiac module 114 into neuro module 116 and back into cardiac module 114. Again, when cardiac module 114 transmits a stimulation signal, switches S52 and S53 of isolation circuit 408 are open, and similarly, switch S54, which may be considered an isolation circuit, is also open.

Notably, during times when cardiac module 114 is transmitting a stimulation signal, neuro module 116 may not need to measure signals such as impedance or other signals. Accordingly, the common mode interference that may be caused by the simulation signal of cardiac module 114 may not impact neuro module 116. Nevertheless, electrodes 104, 106 may experience little to no common mode interference due to the stimulation generated via cardiac module 114 because the stimulation generated by cardiac module 114 is not referenced to the same voltage and ground as electrodes 104, 106. As described above, when cardiac module 114 transmits a stimulation signal, neuro module 116 may be powered by power device 406. In this mode of operation, electrodes 104, 106 are referenced to the voltage and ground provided by power device 406. When switches S52 and S53 of isolation circuit 408 are open, the output of power device 406 is not referenced to power source 108 and ground provided by housing 70.

After opening switches S52, S53, and S54, processor 404 may close switches S52, S53, and S54 after a predetermined amount of time. In some examples, the predetermined amount of time may be between about 0.1 seconds to about 20 seconds. After switches S53 and S54 of isolation circuit 408 are closed, power source 108 recharges power device 406.

In some examples, cardiac module 114 may not transmit a signal to neuro module 116 indicating the cardiac module 114 is about to transmit a stimulation signal. In these examples, processor 404 may monitor the voltage across electrodes 104, 106 and/or monitor the current through electrodes 104, 106. If the voltage across electrodes 104, 106 and/or current through electrodes 104, 106 is greater than a threshold value, processor 404 may open switches S52, S53, and S54 thereby reducing or eliminating the commonality between cardiac module 116 and neuro module 114.

In the example shown in FIG. 33, prior to and while neuro module 116 outputs a stimulation signal or sense a signal, processor 404 may open switches S52, S53, and S54 before transmitting the stimulation signal or before sensing a signal. Accordingly, when neuro module 116 transmits its stimulation signal, there is no commonality between the neuro module 116 and cardiac module 114. In this example, the shunt current that may flow into cardiac module 114 may be reduced or eliminated because there is no complete circuit for the shunt current to flow from neuro module 116 into cardiac module 114 and back into neuro module 116. Also, the common mode interference experienced by cardiac module 114 may be reduced or eliminated because there is no commonality between cardiac module 114 and neuro module 116. Also, because there is no commonality between cardiac module 114 and neuro module 116 when switches S52, S53, and S54 are open, neuro module 116 may not experience common mode interference while neuro module 116 senses signals.

In some alternate examples, processor 404 may not open switches in response to a signal from cardiac module 116 and may not monitor the voltages on or currents through electrodes 104, 106. Instead, processor 404 may periodically or pseudo-randomly open and close switches S52 and the switches of isolation circuit 408, e.g., S53, and S54. In these examples, switches S52, S53, and S54 may generally be open. In some examples, when processor 404 may monitor the voltage on power device 406. If the voltage on power device 406 falls below a predetermined threshold voltage, processor 404 may close the switches in isolation circuit 408, e.g., switches S52 and S53, to recharge power device 406. Prior to when processor 404 receives data from or transmit data to processor 122, processor 404 may close switches S52, S53, and S54 to receive or transmit the data.

The duration of time that processor 404 closes switches S52, S53, and S54 may be relatively small. For example, the duration may be approximately 0.1 microseconds to 10 milliseconds. Such a duration may be sufficient to convey data from processor 122 to processor 404, and may be sufficient to convey a burst of power to power device 406.

In some examples, rather than processor 404 closing switches only when processor 404 receives or transmits data to processor 122 or when the voltage across power device 406 drops below a threshold level, processor 404 may periodically toggle switches S52, S53, and S54. For example, processor 404 may close switches S52, S53, and S54 for a duration between approximately 0.1 microseconds to 10 milliseconds and open switches S52, S53, and S54 for a duration between approximately 1 second and 10 seconds.

In examples where processor 404 toggles switches pseudo-randomly or periodically, the common-mode interference and shunt current may be reduced to a point where the common-mode interference and shunt current is inconsequential. Due to the brief times when there is commonality, e.g., for 0.1 microsecond to 10 milliseconds, the possibility that there may be common-mode interference and/or shunt current is drastically reduced. In other words, it is unlikely that cardiac module 114 may generate a stimulation signal during the brief times that there is commonality between cardiac module 114 and neuro module 116. Furthermore, even if there happens to be a stimulation signal generated by cardiac module 114 when there is commonality between cardiac module 114 and neuro module 116, the duration of the shunt current may be brief and inconsequential because the duration where there is commonality between cardiac module 114 and neuro module 116 is brief.

Moreover, the common-mode interference may be inconsequential if, in some examples, the duration when there is commonality between neuro module 116 and cardiac module 114 is asynchronous to times when cardiac module 114 may measure a signal. Also, the common-mode interference may be inconsequential if, in some examples, where the duration of the commonality is periodic, processor 404 may toggle switches S52, S53, and S54 at a rate that may be substantially slower than the rate at which cardiac module 114 may measure signals. In these examples, cardiac module 114 may convey to neuro module 116 the rate at which cardiac module 114 may measure signals. The common-mode interference may be inconsequential if, in some examples, where the duration of the commonality is periodic, processor 404 closes switches S52, S53, and S54 during a "blanking" period of cardiac module 114. The blanking period of cardiac module 114 may be times when cardiac module 114 is not measuring signals.

FIG. 34 is a functional block diagram of another example configuration of IMD 16. FIG. 34 may be substantially similar to FIG. 33. However, as shown in FIG. 34, neuro module 116 is powered directly by power source 108. In FIG. 34, cardiac module 114 is powered by isolation circuit 414. In the example of FIG. 34, switch 57 may be considered as an isolation circuit that isolates processor 122 from cardiac module 114.

In FIG. 34, power device 412 may be substantially similar to power device 406 of FIG. 33. Isolation circuit 414 may be substantially similar to isolation circuit 408 of FIG. 33. Processor 410 may be substantially similar to processor 404 of FIG. 33. Switches S55, S56, and S57 may be substantially similar to switches S52, S53, and S54 of FIG. 33.

Similar to FIG. 33, the effects of common-mode interference and shunt current generated by neuro module 116 on cardiac module 114 may be reduced or eliminated. Switches S55, S56, and S57 may be open prior to and while neuro module 116 transmits a stimulation signal. In this manner the commonality between cardiac module 114 and neuro module 116 may be reduced or eliminated. As described above, the reduction of commonality between cardiac module 114 and neuro module 116 may sufficiently reduce or eliminate common-mode interference and shunt current.

In general, the example IMD 16 shown in FIG. 34 may function essentially the same as the example IMD 16 shown in FIG. 33. However, as shown in FIG. 34, is some examples, isolation circuit 414 may isolate the power to cardiac module 114 from power source 108. Also, as shown in FIG. 34, in some examples, switch 57 may isolate processor 122 from the processor within cardiac module 114, e.g., processor 410.

The examples shown in FIGS. 33 and 34 are for illustration purposes and should not be considered as limiting. In some examples, IMD 16 may include components shown in both FIGS. 33 and 34.

The techniques described in this disclosure, including those attributed to cardiac module 82, 114, and 160 and neuro module 84, 116, and 162, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" or "control circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described in this disclosure are primarily described as being performed by processor 86A, 86B, and 122, any one or more parts of the techniques described in this disclosure may be implemented by a processor of one of the cardiac or neuro modules or another computing device, alone or in combination with the cardiac or neuro modules.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various aspects of the disclosure have been described. These and other aspects are within the scope of the following claims.

The invention claimed is:

1. An implantable medical device (IMD) comprising:
a housing;
a cardiac module, in the housing, configured to deliver electrical stimulation therapy to a patient;
a power source that couples to the cardiac module and is configured to provide power to the cardiac module;
at least one isolation circuit that couples to the power source; and
a neurostimulation module, in the housing, that couples to the power source via the at least one isolation circuit and is configured to deliver electrical stimulation therapy to the patient or sense a physiological condition of the patient,
wherein the at least one isolation circuit is configured to electrically isolate the power source from the neurostimulation module to reduce common-mode interference on the neurostimulation module, and
wherein the common-mode interference is caused by the cardiac module delivering electrical stimulation therapy to the patient.

2. An implantable medical device (IMD) comprising:
a housing;
a first module, in the housing, configured to deliver electrical stimulation therapy to a patient;
a power source that couples to the first module and is configured to provide power to the first module;
at least one isolation circuit that couples to the power source; and
a second module, in the housing, that couples to the power source via the at least one isolation circuit and is configured to deliver electrical stimulation therapy to the patient or sense a physiological condition of the patient,
wherein the at least one isolation circuit is configured to electrically isolate the power source from the second module to reduce at least one of common-mode interference and shunt current on the second module, and
wherein the at least one of common-mode interference and shunt current is caused by the first module delivering electrical stimulation therapy to the patient.

3. The IMD of claim 2, wherein a voltage at a power input of the second module is floating with respect to a voltage of the power source due to the at least one isolation circuit.

4. The IMD of claim 2, wherein the first module comprises a cardiac module and the second module comprises a neurostimulation module.

5. The IMD of claim 2, wherein the at least one isolation circuit comprises:
a first and a second switch coupled to a first and a second input line, respectively, wherein the first input line and the second input line are coupled to the power source and a ground of the power source, respectively;
a capacitor circuit that is coupled to the first and second switch;
a third and fourth switch, wherein the capacitor circuit is coupled to the third and fourth switch, and wherein the third switch is further coupled to the first switch and the fourth switch is further coupled to the second switch;
a capacitor, wherein the capacitor is coupled to the third and fourth switch; and
a fifth and sixth switch coupled to a first and second output line, respectively, wherein the capacitor is coupled to the fifth and sixth switch, and wherein the first output line is coupled to a power input of the second module and the second output line is coupled to a ground terminal of the second module,
wherein, in a first state, the first and second switches are closed and the third, fourth, fifth, and sixth switches are opened to charge the capacitor circuit, in a second state, the first, second, fifth and sixth switches are opened and the third and fourth switches are closed to discharge the capacitor circuit and charge the capacitor, and, in a third state, the third and fourth switches are opened and the first, second, fifth, and sixth switches are closed to provide isolated power to the second module coupled to the isolation circuit,
wherein after the capacitor discharges, the first and second switches are opened and the third and fourth switches are closed to charge the capacitor and provide isolated power, and
wherein after the capacitor charges, the third and fourth switches are opened and the first and second switches are closed to provide power on the first and second output line.

6. The IMD of claim 5, wherein the capacitor circuit comprises:
at least two capacitors; and
at least three switches,
wherein a first switch and a second switch of the at least three switches are closed and a third switch of the at least three switches is opened to charge the at least two capacitors in parallel, and wherein the first and second switch of the at least three switches are opened and the third switch of the at least three switches is closed to discharge the at least two capacitors in series.

7. The IMD of claim 2, wherein the at least one isolation circuit comprises:
an oscillator coupled to a first and a second input line and configured to generate a first oscillating pulse, wherein the first and the second input line are coupled to the power source and a ground of the power source;
a transformer coupled to the oscillator and configured to transform the first oscillating pulse to a second oscillating pulse;
a rectifier coupled to the transformer and configured to rectify the second oscillating pulse; and
a capacitor coupled to the rectifier and configured to generate an isolated direct current (DC) voltage across a first and second output line,
wherein the first and second output line are coupled to a power input of the second module and a ground terminal of the second module, respectively.

8. The IMD of claim 2, wherein the at least one isolation circuit comprises:
an oscillator coupled to a first and a second input line and configured to generate a first oscillating pulse, wherein the first and the second input line are coupled to a power source and a ground of the power source, respectively;
a barrier circuit coupled to the oscillator that is configured to receive the first oscillating pulse and generate a second oscillating pulse that is isolated from the first oscillating pulse;
a rectifier coupled to the barrier circuit configured to rectify the second oscillating pulse; and
a capacitor coupled to the rectifier configured to generate an isolated direct current (DC) voltage across a first and second output line,
wherein the first output line is coupled to a power input of the second module and the second output line is coupled to a ground terminal of the second module.

9. The IMD of claim 8, wherein the barrier circuit comprises:
a first resistor coupled between a first and second output of the oscillator;
a first capacitor coupled to a first end of the first resistor;
a second capacitor coupled to a second end of the first resistor; and
a second resistor coupled between a first and second input to the rectifier, wherein a first end of the second resistor is coupled to the first capacitor and a second end of the second resistor is coupled to the second capacitor.

10. The IMD of claim 2, wherein the at least one isolation circuit comprises:
a light emitting diode (LED) that is coupled to the power source and a ground of the power source; and
a photo-voltaic cell that is configured to generate a voltage in response to illumination of the LED,
wherein the photo-voltaic cell is coupled to the second module.

11. The IMD of claim 2, wherein the at least one isolation circuit comprises:
a first switch coupled between the power source and a power input of the second module; and
a second switch coupled between a ground of the power source and a ground terminal of the second module,
wherein a first terminal of a power device is coupled to the power input of the second module and a second terminal of the power device is coupled to the ground terminal of the second module,
wherein the power device is charged to a sufficient voltage to power the second module when the first and second switches are closed, wherein, prior to transmitting a stimulation signal, the first module transmits an indication signal to the second module, and wherein the second module, in response to the indication signal, opens the first and second switch.

12. The IMD of claim 2, wherein the at least one isolation circuit comprises a first isolation circuit, the IMD further comprising:
a second isolation circuit that couples the second module to a common component shared with the first module, wherein the common component is configured to transfer data between the first and second modules.

13. The IMD of claim 12, wherein the common component comprises at least one of a processor, a telemetry module, and a memory device.

14. The IMD of claim 12, wherein the second isolation circuit comprises at least one of:
a first resistor that couples the second module to the common component and a second resistor that couples a ground terminal of the second module to a ground of the power device,
a first capacitor that couples the second module to the common component and a second capacitor that couples the ground terminal of the second module to the ground of the power source,
a transformer, wherein a primary side of the transformer is coupled to the common component and the ground of the power source and a secondary side of the transformer is coupled to the second module and the ground terminal of the second module,
a first opto-isolator that couples the second module to the common component and a second opto-isolator that couples the ground terminal of the second module to the ground of the power source, and
a first photo-voltaic cell that couples the second module to the common component and a second photo-voltaic cell that couples the ground terminal of the second module to the ground of the power source.

15. The IMD of claim 12, wherein the second isolation circuit comprises:
a processor;
a first capacitor and a second capacitor; and
a first group of switches and a second group of switches,
wherein the processor closes the first group of switches and opens a second group of switches to charge the first capacitor to transfer data to the processor from the second module, and
wherein the processor opens the first group of switches and closes the second group of switches to discharge the first capacitor and charge the second capacitor to transfer data to the second module from the processor.

16. The IMD of claim 12, wherein the second isolation circuit comprises:
a memory device that includes at least a power terminal, a ground terminal, a serial read/write terminal, and a control terminal;
a first switch coupled between the power source and the power terminal;
a second switch coupled between a floating power line and the power terminal, wherein the floating power line is a first output of the first isolation circuit;
a third switch coupled between a ground of the power source and the ground terminal;
a fourth switch coupled between a floating ground line and the ground terminal, wherein the floating ground line is a second output of the first isolation circuit;
a fifth switch coupled between the second module and the serial read/write terminal;
a sixth switch coupled between the common component and the serial read/write terminal;
a seventh switch coupled between the second module and the control terminal; and
an eighth switch coupled between the common component and the control terminal,
wherein, when the common component writes data to or reads data from the memory device, the common component opens the first, third, fifth, and seventh switches and closes the first, third, fifth, and seventh switches,
wherein, when the second module writes data to or reads data from the memory device, second module opens the second, fourth, sixth, and eighth switches and closes the second, fourth, sixth, and eight switches,
wherein when the first, third, fifth, and seventh switches are closed, the second, fourth, sixth, and eighth switches are open, and
wherein when the second, fourth, sixth, and eighth switches are closed, the first, third, fifth, and seventh switches are open.

17. The IMD of claim 2, wherein the at least one isolation circuit enables data transmission between the first therapy module and the second therapy module.

18. A method comprising:
delivering, via a first module within a housing of an implantable medical device (IMD), electrical stimulation therapy to a patient, wherein the first module is powered via a power source;
delivering, via a second module within the housing of the IMD, electrical stimulation therapy to the patient or sensing, via the second module within the housing of the IMD, a physiological condition of the patient, wherein the second module is powered via at least one isolation circuit that couples to the power source; and
isolating the power source from the second module via the at least one isolation circuit to reduce at least one of common-mode interference and shunt current on the second module,
wherein delivering electrical stimulation via the first module causes the at least one of common-mode interference and shunt current.

19. The method of claim 18, wherein a voltage at a power input of the second module is floating with respect to a voltage of the power source due to the at least one isolation circuit.

20. The method of claim 18, wherein the first module comprises a cardiac module and the second module comprises a neurostimulation module.

21. The method of claim 18, wherein the at least one isolation circuit comprises:
a first and second switch coupled to a first and second input line, respectively, wherein the first and second input line are coupled to the power source and a ground of the power source; and
a capacitor circuit that is coupled to the first and second switch, a third and fourth switch, wherein the capacitor circuit is coupled to the third and fourth switch,
wherein the third switch is further coupled to the first switch and the fourth switch is further coupled to the second switch, a capacitor,
wherein the capacitor is coupled to the third and fourth switch, and a fifth and sixth switch coupled to a first and second output line, respectively,
wherein the capacitor is coupled to the fifth and sixth switch, wherein the first and second output line is coupled to a power input of the second module and a ground terminal of the second module, respectively, and wherein isolating the power source from the second module via the at least one isolation circuit to reduce at least one of common-mode interference and shut current on the second module comprises:

closing the first and second switches and opening the third, fourth, fifth, and sixth switches to charge the capacitor circuit;

opening the first and second switches and closing the third and fourth switches to discharge the capacitor circuit and charge the capacitor;

opening the third and fourth switches and closing the first, second, fifth, and sixth switches to provide isolated power to the first or second module coupled to the first and second output lines;

after the capacitor discharges, opening the first and second switches and closing the third and fourth switches to charge the capacitor and provide isolated power; and after the capacitor charges, opening the third and fourth switches and closing the first and second switches to generate an isolated direct current (DC) voltage across the first and second output line.

22. The method of claim 21, wherein the capacitor circuit comprises:

at least two capacitors; and at least three switches, wherein isolating the power source from the second module via the at least one isolation circuit to reduce at least one of common-mode interference and shut current on the second module comprises:

closing a first switch and a second switch of the at least three switches;

opening a third switch of the at least three switches to charge the at least two capacitors in parallel;

opening the first and second switch of the at least three switches; and closing the third switch of the at least three switches to discharge the at least two capacitors in series.

23. The method of claim 18, wherein isolating the power source from the second module via the at least one isolation circuit to reduce at least one of common-mode interference and shut current on the second module comprises:

generating a first oscillating pulse via an oscillator coupled to a first and second input line, wherein the first and second input line is coupled to the power source and a ground of the power source, wherein the power source provides power to the oscillator, and wherein the at least one isolation circuit includes the oscillator;

generating a second oscillating pulse via a transformer, wherein the at least one isolation circuit includes the transformer, and wherein the transformer receives the first oscillating pulse to generate the second oscillating pulse;

rectifying the second oscillating pulse; and smoothing the rectified second oscillating pulse to generate an isolated direct current (DC) voltage across a first and second output line via a capacitor, wherein the at least one isolation circuit includes the capacitor, and wherein the first and second output line is connected to a power input of the second module and a ground terminal of the second module.

24. The method of claim 18, wherein isolating the power source from the second module via the at least one isolation circuit to reduce at least one of common-mode interference and shut current on the second module comprises:

generating a first oscillating pulse via an oscillator coupled to a first and second input line, wherein the first and second input line is coupled to the power source and a ground of the power source, wherein the power source provides power to the oscillator, wherein the at least one isolation circuit includes the oscillator;

generating a second oscillating pulse via a barrier circuit, wherein the at least one isolation circuit includes the barrier circuit, and wherein the barrier circuit receives the first oscillating pulse to generate the second oscillating pulse;

rectifying the second oscillating pulse; and smoothing the rectified second oscillating pulse to generate an isolated direct current (DC) voltage across a first and second output line via a capacitor, wherein the at least one isolation circuit includes the capacitor, and wherein the first output line is connected to a power input of the second module and the second output line is connected to a ground terminal of the second module.

25. The method of claim 24, wherein the barrier circuit comprises:

a first resistor coupled between a first and second output of the oscillator;

a first capacitor coupled to a first end of the first resistor;

a second capacitor coupled to a second end of the first resistor; and a second resistor coupled between a first and second input to the rectifier, wherein a first end of the second resistor is coupled to the first capacitor and a second end of the second resistor is coupled to the second capacitor.

26. The method of claim 18, wherein isolating the power source from the second module via the at least one isolation circuit to reduce at least one of common-mode interference and shunt current on the second module comprises:

illuminating a light emitting diode (LED) that is coupled to the power source and a ground of the power source, wherein the at least one isolation circuit includes the LED; and generating a voltage on a photo-voltaic cell in response to the illumination, wherein the at least one isolation circuit includes the photo-voltaic cell, and wherein the photo-voltaic cell couples to a power input and a ground terminal of the second module.

27. The method of claim 18, wherein the at least one isolation circuit comprises:

a first switch coupled between the power source and a power input of the second module; and a second switch coupled between a ground of the power source and a ground terminal of the second module, wherein a first terminal of a power device is coupled to the power input of the second module and a second terminal of the power device is coupled to the ground terminal of the second module, and wherein isolating the power source from the second module via the at least one isolation circuit to reduce at least one of common-mode interference and shunt current on the second module comprises:

transmitting an indication signal from the first module to the second module, prior to the first module transmitting the stimulation signal, indicating that the first module is about to delivery the stimulation signal;

opening, via the second module, the first and second switch in response to the indication signal.

28. The method of claim 18, wherein the at least one isolation circuit comprises a first isolation circuit, the method further comprising:

isolating a common component shared by both the first and second modules via a second isolation circuit that couples the second module to the common component, wherein the common component transfers data between the first and second modules.

29. The method of claim 28, wherein the common component comprises at least one of a processor, a telemetry module, and a memory device.

30. The method of claim 28, wherein the second isolation circuit comprises at least one of:
- a first resistor that couples the second module to the common component and a second resistor that couples a ground terminal of the second module to a ground of the power source,
- a first capacitor that couples the second module to the common component and a second capacitor that couples the ground terminal of the second module to the ground of the power device,
- a transformer, wherein a first side of the transformer is coupled to the common component and the ground of the power device and a second side of the transformer is coupled to the second module and the ground terminal of the second module,
- a first opto-isolator that couples the second module to the common component and a second opto-isolator that couples the ground terminal of the second module to the ground of the power device, and
- a first photo-voltaic cell that couples the second module to the common component and a second photo-voltaic cell that couples the ground terminal of the second module to the ground of the power device.

31. The method of claim 28, wherein the second isolation circuit comprises a processor, a first capacitor and a second capacitor, and a first group of switches and a second group of switches, and wherein isolating a common component shared by both the first and second modules comprises:
- closing the first group of switches and opening a second group of switches to charge the first capacitor to transfer data to the processor from the second module, and
- opening the first group of switches and closing the second group of switches to discharge the first capacitor and charge the second capacitor to transfer data to the second module from the processor.

32. The method of claim 28, wherein the second isolation circuit comprises:
- a memory device that includes at least a power terminal, a ground terminal, a serial read/write terminal, and a control terminal;
- a first switch coupled between the power source and the power terminal;
- a second switch coupled between a floating power line and the power terminal, wherein the floating power line is a first output of the first isolation circuit;
- a third switch coupled between a ground of the power source and the ground terminal;
- a fourth switch coupled between a floating ground line and the ground terminal, wherein the floating ground line is a second output of the first isolation circuit;
- a fifth switch coupled between the second module and the serial read/write terminal;
- a sixth switch coupled between the common component and the serial read/write terminal;
- a seventh switch coupled between the second module and the control terminal; and
- an eighth switch coupled between the common component and the control terminal, and wherein isolating a common component shared by both the first and second modules comprises:
- closing the first, third, fifth, and seventh switches when the common component writes data to or reads data from the solid state memory device; and
- closing the second, fourth, sixth, and eight switches when the second module writes data to or reads data from the solid state memory device,
- wherein when the first, third, fifth, and seventh switches are closed, the second, fourth, sixth, and eighth switches are open, and
- wherein when the second, fourth, sixth, and eighth switches are closed, the first, third, fifth, and seventh switches are open.

33. The method of claim 18, wherein the at least one isolation circuit enables data transmission between the first therapy module and the second therapy module.

34. An implantable medical device (IMD) comprising:
a housing;
a first means, in the housing, for delivering electrical stimulation therapy to a patient, wherein the first means is powered via a power source; and
a second means, in the housing, for delivering a electrical stimulation therapy to the patient or sensing a physiological condition of the patient, wherein the second means is powered via at least one means for isolating that couples to the power source,
wherein the means for isolating isolates the power source from the second means to reduce at least one of common-mode interference and shut shunt current on the second means,
wherein delivering electrical stimulation via the first means causes the at least one of common-mode interference and shunt current.

35. An implantable medical device (IMD) comprising:
a housing;
a cardiac module, in the housing, configured to deliver electrical stimulation therapy to a patient;
a power source that couples to the cardiac module and is configured to provide power to the cardiac module;
at least one isolation circuit that couples to the power source, wherein the at least one isolation circuit comprises:
- a first and a second switch coupled to a first and a second input line, respectively, wherein the first input line and the second input line are coupled to the power source and a ground of the power source, respectively;
- a capacitor circuit that is coupled to the first and second switch;
- a third and fourth switch, wherein the capacitor circuit is coupled to the third and fourth switch, and wherein the third switch is further coupled to the first switch and the fourth switch is further coupled to the second switch;
- a capacitor, wherein the capacitor is coupled to the third and fourth switch; and
- a fifth and sixth switch coupled to a first and second output line, respectively, wherein the capacitor is coupled to the fifth and sixth switch,
wherein, in a first state, the first and second switches are closed and the third, fourth, fifth, and sixth switches are opened to charge the capacitor circuit, in a second state, the first, second, fifth and sixth switches are opened and the third and fourth switches are closed to discharge the capacitor circuit and charge the capacitor, and, in a third state, the third and fourth switches are opened and the first, second, fifth, and sixth switches are closed to provide isolated power to the neurostimulation module coupled to the isolation circuit, wherein after the capacitor discharges, the first and second switches are opened and the third and fourth switches are closed to charge the capacitor and provide isolated power, and wherein after the capacitor charges, the third and fourth switches are opened and the first and second switches are closed to provide power on the first and second output line; and a neurostimulation module, in the housing, that couples to the first output line and the second output line of the at least one isolation circuit to receive power and is configured to deliver electrical stimulation therapy to the patient or sense a physiological condition of the patient, wherein the at least one isolation circuit is configured to electrically isolate the power source from the neurostimulation module to reduce at least one of common-mode interference and shunt current on the neurostimulation module, and wherein the at least one of common-mode interference and shunt current is caused by the cardiac module delivering electrical stimulation therapy to the patient.

36. An implantable medical device (IMD) comprising:

a housing;

a processor;

a cardiac module, in the housing, configured to deliver electrical stimulation therapy to a patient;

a power source that couples to the cardiac module and is configured to provide power to the cardiac module;

at least one isolation circuit that couples to the power source, wherein the at least one isolation circuit comprises:

an oscillator coupled to a first and a second input line and further coupled to the processor, and configured to generate a first oscillating pulse that comprises data provided by the processor, wherein the first and the second input line are coupled to the power source and a ground of the power source;

a transformer coupled to the oscillator and configured to transform the first oscillating pulse to a second oscillating pulse;

a data demodulator coupled to the transformer and configured to provide data between the cardiac and neurostimulation modules;

a rectifier coupled to the transformer and configured to rectify the second oscillating pulse; and a capacitor coupled to the rectifier and configured to generate an isolated direct current (DC) voltage across a first and second output line;

a neurostimulation module, in the housing, that couples to the first and second output line of the at least one isolation circuit and is configured to deliver electrical stimulation therapy to the patient or sense a physiological condition of the patient, wherein the at least one isolation circuit is configured to electrically isolate the power source from the neurostimulation module to reduce at least one of common-mode interference and shunt current on the neurostimulation module, and wherein the at least one of common-mode interference and shunt current is caused by the cardiac module delivering electrical stimulation therapy to the patient.

* * * * *

UNITED STATES PATENT AND TRADEMARK OFFICE
CERTIFICATE OF CORRECTION

Page 1 of 1

PATENT NO.        : 8,498,698 B2
APPLICATION NO.   : 12/551409
DATED             : July 30, 2013
INVENTOR(S)       : William T. Donofrio et al.

It is certified that error appears in the above-identified patent and that said Letters Patent is hereby corrected as shown below:

In the Claims

Col. 87, line 6, delete "interference and shut current" and insert in place thereof -- interference and shunt current --;

Col. 90, line 23, delete "delivering a electrical" and insert in place thereof -- delivering an electrical --;

Col. 90, line 30, delete "interference and shut shunt current" and insert in place thereof -- interference and shunt current --.

Signed and Sealed this
Fourth Day of November, 2014

Michelle K. Lee
*Deputy Director of the United States Patent and Trademark Office*